(12) United States Patent
Kunimoto et al.

(10) Patent No.: US 9,631,048 B2
(45) Date of Patent: Apr. 25, 2017

(54) SULFONIUM COMPOUNDS, THEIR PREPARATION AND USE

(71) Applicant: BASF SE, Ludwigshafen (DE)

(72) Inventors: Kazuhiko Kunimoto, Kawanishi (JP); Hisatoshi Kura, Takarazuka (JP)

(73) Assignee: BASF SE, Ludwigshafen (DE)

(*) Notice: Subject to any disclaimer, the term of this patent is extended or adjusted under 35 U.S.C. 154(b) by 0 days.

(21) Appl. No.: 14/389,831

(22) PCT Filed: Apr. 17, 2013

(86) PCT No.: PCT/EP2013/057968
§ 371 (c)(1),
(2) Date: Oct. 1, 2014

(87) PCT Pub. No.: WO2013/156509
PCT Pub. Date: Oct. 24, 2013

(65) Prior Publication Data
US 2015/0044509 A1    Feb. 12, 2015

Related U.S. Application Data

(60) Provisional application No. 61/635,317, filed on Apr. 19, 2012.

(30) Foreign Application Priority Data

Apr. 19, 2012 (EP) .................................. 12164769

(51) Int. Cl.
  B05D 3/00     (2006.01)
  C07C 309/08   (2006.01)
  (Continued)

(52) U.S. Cl.
  CPC .............. *C08G 59/62* (2013.01); *B05D 3/007* (2013.01); *C07C 309/08* (2013.01);
  (Continued)

(58) Field of Classification Search
  CPC ..... B05D 3/007; C07C 309/08; C07C 309/10; C07C 2101/08; C07C 2101/14;
  (Continued)

(56) References Cited

U.S. PATENT DOCUMENTS 4,997,717 A  3/1991 Rembold et al.
5,650,263 A  7/1997 Wakata et al.
(Continued)

FOREIGN PATENT DOCUMENTS

DE  36 36 183 A1  3/1988
EP  0 008 127 A1  2/1980
(Continued)

OTHER PUBLICATIONS

International Search Report issued Dec. 10, 2013 in PCT/EP2013/057968.
(Continued)

*Primary Examiner* — Paul A Zucker
*Assistant Examiner* — Mark Luderer
(74) *Attorney, Agent, or Firm* — Oblon, McClelland, Maier & Neustadt, L.L.P.

(57) ABSTRACT

Compounds of the formula (I), (Ia) or (Ib) wherein $A_1$, and $A^-$ is for example (II) is 1 or 2; X is $C_1$-$C_4$ alkylene or CO; Y is for example O, O(CO), O(CO)O, $R_1$ is for example hydrogen, d-dsalkyl, $C_3$-$C_{30}$cycloalkyl, phenyl, naphthyl, anthracyl, phenanthryl, biphenylyl, fluorenyl or $C_3$-$C_{20}$heteroaryl, all of which optionally are substituted; $R_2$ and $R_3$ for example are $C_1$-$C_{10}$haloalkylene which is optionally substituted, or $R_2$ and $R_3$ are phenylene, which optionally is substituted; $R_4$ is a group (A) or a group (B); $R_5$ and $R_6$ for example are $C_1$-$C_{20}$alkyl; or $R_4$ and $R_5$ or $R_4$ and $R_6$ together form a straight-chain $C_2$-$C_6$alkylene, $R_5$ and $R_6$ together form a straight-chain $C_2$-$C_6$alkylene; $R_7$, $R_8$, $R_9$ and $R_{10}$ ifor example are $C_1$-$C_{20}$alkyl; M for example is $C_1$-$C_{20}$alkylene, $C_2$-$C_{20}$alkenylene, $C_2$-$C_{20}$alkynylene; $R_{25}$ and $R_{26}$ are for example hydrogen, $C_1$-$C_{20}$alkyl; $R_{27}$, $R_{28}$, $R_{29}$, $R_{30}$ and $R_{31}$ are for example hydrogen, $C_1$-$C_{20}$alkyl, $C_2$-$C_{20}$alkenyl, $C_3$-$C_{20}$cycloalkyl, or two radicals $R_{27}$ and $R_{28}$, $R_{28}$ and $R_{29}$, $R_{29}$ and $R_{30}$ and/or $R_{30}$ and $R_{31}$ together form a straight-chain $C_2$-$C_6$alkylene, or $R_{25}$ and $R_{27}$ together form 1,2-phenylene, $R_{33}$ and $R_{34}$ for example are hydrogen, $C_1$-$C_{20}$alkyl; $R_{35}$, $R_{36}$ and $R_{37}$ for example are hydrogen, $C_1$-$C_{20}$alkyl; are suitable as thermo-acid generators.

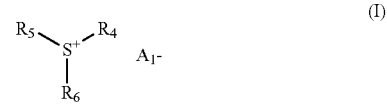

(I)

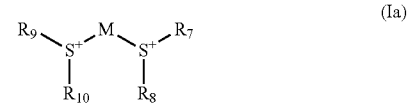

(Ia)

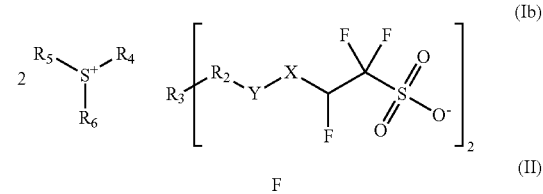

(Ib)

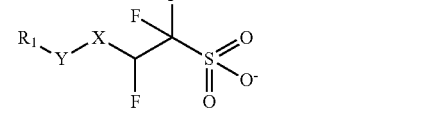

(II)

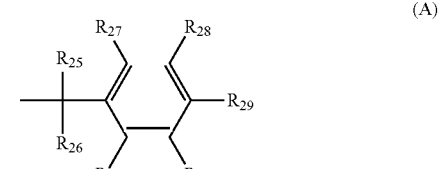

(A)

(Continued)

-continued

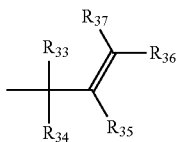
(B)

20 Claims, No Drawings

(51) Int. Cl.
| | |
|---|---|
| C07C 309/10 | (2006.01) |
| C07D 307/10 | (2006.01) |
| C07D 309/08 | (2006.01) |
| C07D 333/46 | (2006.01) |
| C08G 59/40 | (2006.01) |
| C08G 59/62 | (2006.01) |
| C08L 63/00 | (2006.01) |
| C09D 11/02 | (2014.01) |
| C09D 163/00 | (2006.01) |
| C09J 163/00 | (2006.01) |
| G03F 7/00 | (2006.01) |
| G03F 7/004 | (2006.01) |

(52) U.S. Cl.
CPC .......... *C07C 309/10* (2013.01); *C07D 307/10* (2013.01); *C07D 309/08* (2013.01); *C07D 333/46* (2013.01); *C08G 59/4064* (2013.01); *C08L 63/00* (2013.01); *C09D 11/02* (2013.01); *C09D 163/00* (2013.01); *C09J 163/00* (2013.01); *C07C 2101/08* (2013.01); *C07C 2101/14* (2013.01); *G03F 7/0045* (2013.01)

(58) Field of Classification Search
CPC .. C07D 307/10; C07D 309/08; C07D 333/46; C08G 59/4064; C08G 59/62; C08L 63/00; C09D 11/02; C09D 163/00; C09J 163/00; G03F 7/0045
See application file for complete search history.

(56) References Cited

U.S. PATENT DOCUMENTS

| 6,313,188 | B1 | 11/2001 | Takahashi |
| 6,593,388 | B2 | 7/2003 | Crivello |
| 6,908,722 | B2 | 6/2005 | Ebata et al. |
| 2003/0113658 | A1 | 6/2003 | Ebata et al. |
| 2006/0276670 | A1 | 12/2006 | Junk et al. |
| 2007/0184382 | A1 | 8/2007 | Yamaguchi et al. |
| 2008/0076063 | A1 | 3/2008 | Yoshida et al. |
| 2008/0081293 | A1 | 4/2008 | Harada et al. |
| 2010/0273105 | A1 | 10/2010 | Utsumi et al. |
| 2011/0076615 | A1* | 3/2011 | Kawabata ............ G03F 7/0045 430/270.1 |
| 2011/0217654 | A1* | 9/2011 | Yamato ............... C07C 271/24 430/270.1 |
| 2011/0287362 | A1 | 11/2011 | Seshimo et al. |

FOREIGN PATENT DOCUMENTS

| EP | 0 249 201 A2 | 12/1987 |
| EP | 0 276 501 A2 | 8/1988 |
| EP | 0 927 726 A1 | 7/1997 |
| EP | 1 270 553 A2 | 1/2003 |
| EP | 1 710 230 A1 | 10/2006 |
| GB | 2 441 032 | 2/2008 |
| GB | 2 444 823 | 6/2008 |
| GB | 2 446 273 | 8/2008 |
| JP | 57-42009 A | 3/1982 |
| JP | 1-130103 A | 5/1989 |
| JP | 1-134306 A | 5/1989 |
| JP | 7-261015 A | 10/1995 |
| JP | 7-281440 A | 10/1995 |
| JP | 8-334893 A | 12/1996 |
| JP | 9-197660 A | 7/1997 |
| JP | 9-325483 A | 12/1997 |
| JP | 11-174459 A | 7/1999 |
| JP | 11-174464 A | 7/1999 |
| JP | 2000-81701 A | 3/2000 |
| JP | 2004-4561 A | 1/2004 |
| JP | 2005148291 | 6/2005 |
| JP | 2005258124 | 9/2005 |
| JP | 2010-134445 | 6/2010 |
| JP | 2010-215600 | 9/2010 |
| JP | 2011-076084 | 4/2011 |
| JP | 2011-219460 | 11/2011 |
| JP | 2012073401 | 4/2012 |
| WO | WO 94/18274 A1 | 8/1994 |
| WO | WO 94/22968 A1 | 10/1994 |
| WO | WO 97/12945 A1 | 4/1997 |
| WO | WO 03/076491 A1 | 9/2003 |
| WO | WO 2006/034445 A1 | 3/2006 |
| WO | WO 2006/073021 A1 | 7/2006 |
| WO | WO 2008/132966 A1 | 11/2008 |
| WO | WO 2009/037980 A1 | 3/2009 |
| WO | WO 2011/104127 A1 | 9/2011 |

OTHER PUBLICATIONS

Office Action as received in the corresponding Japanese Patent Application No. 2015-506223 dated Dec. 7, 2015 (English translation only).

* cited by examiner

SULFONIUM COMPOUNDS, THEIR PREPARATION AND USE

The present invention relates to heat-curable compositions comprising at least one sulfonium compound, to novel sulfonium compounds, to a process for curing cationically polymerizable material and to the cured material obtained by said process.

Cationic polymerization is initiated by a cation generated from a cationic polymerization initiator. The catalysts known for cationic polymerization include sulfonium salts. Compounds showing the highest activity among the sulfonium salts are antimony salts such as $SbF_6$, $SbCl_6$, and $SbF_5(OH)$. However, antimony is a highly toxic substance and is not desirable for practical use. Commercially available untoxic sulfonium salts such as sulfonium phosphates have the drawback that their curing performance is insufficient.

Several sulfonium salts with fluorinatedmethane sulfonated anions are disclosed as photoacid generators; triphenylsulfonium (adamantan-1-ylmethyl)oxycarbonyldi-fluoromethanesulfonate described in JP2004-004561, triphenylsulfonium 1,1,2,2-tetrafluoro-2-(norboman-2-yl)ethanesulfonate described in U.S. Pat. No. 6,908,722, triphenylsulfonium 1,1,3,3,3-pentafluoro-2-benzoyloxypropane-1-sulfonate described in EP1710230, triphenylsulfonium 2-naphtylmethyloxytetrafluoroethanesulfonate described in WO2008/132966, triphenylsulfonium 2-(1'-adamantan)carbonyloxy-1,1-difluoroethanesulfonate described in WO2009/37980, triphenylsulfonium 2-pentafluoroethoxy-1,1,2-trifluoroethanesulfonate described in US2006/276670 and triphenylsulfonium 4-acetyloxy-1,1,2-trifluorobutanesulfonate described in Macromolecules (2007), 40(23), 8220-8224.

There is a great need for non-toxic thermal acid generators (TAG) with good application properties such as a high curing activity. Surprisingly, it has been found that this object is solved by specific sulfonium sulfonates as described below.

The present invention is based on the object, therefore, of providing a non-toxic thermalacid generator having a good curing performance.

One subject of the invention therefore is a compound of the formula I, Ia or Ib

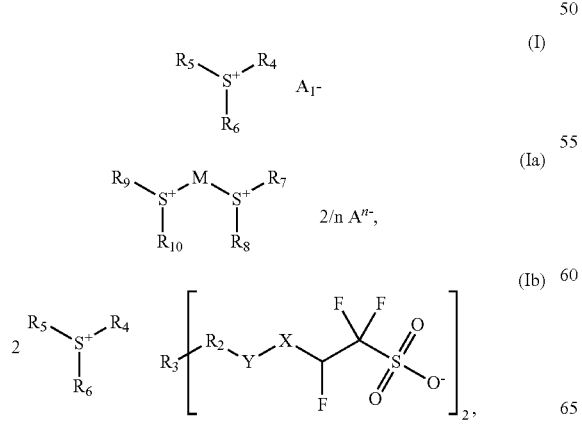

wherein
$A_1^-$ is an anion selected from the group consisting of

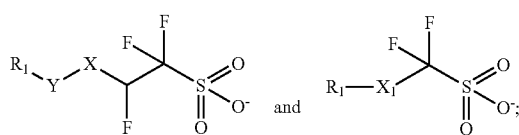

$A^-$ is an anion selected from the group consisting of

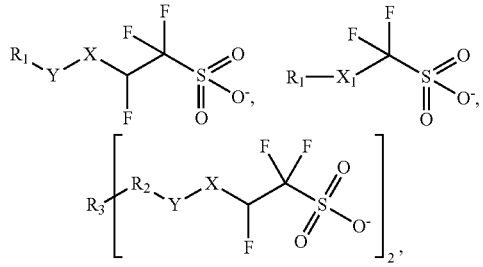

tetrakis(pentafluorophenyl)borate, fluoroalkylphosphate, pentafluorobenzenesulfonate, nitrobenzenesulfonate, di(alkoxycarbonyl)benzenesulfonate, perfluoroalkanesulfonate, difluoromethanedisulfonate, alkylsulfonate, tris(trifluoromethanesulfonyl)methide, bis(perfluoroalkanesulfonyl)imide or 1,1,2,2,3,3-hexafluoropropane-1,3-disulfonimide; provided that at least one anion $A^-$ is

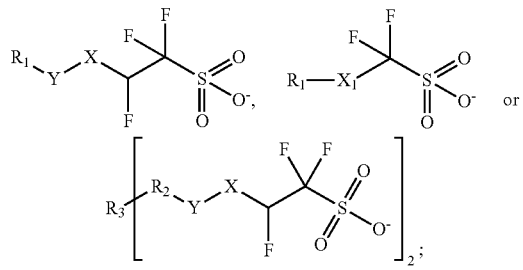

and provided that the anions $A_1^-$ and $A^-$ are not

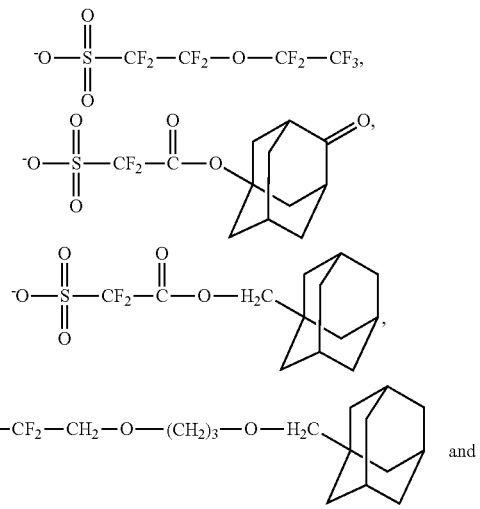

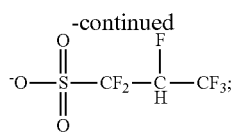

n is 1 or 2;

X is $C_1$-$C_4$alkylene or CO;

$X_1$ is $CH_2$, CO, O, S, $CF_2O$, $SO_2$, $SO_2O$, $SO_2N$ or (CO)O;

Y is O, O(CO), O(CO)O, O(CO)$NR_{11}$, O(CO)$NR_{11}$(CO), $OSO_2$, O(CS), or O(CS)$NR_{11}$, in which for each of these the oxygen atom is directly bound to X;

or is $NR_{11}$, S, $NR_{11}$(CO)O, $NR_{11}$(CS)O, in which the N- or S-atom is directly bound to X; $R_1$ is hydrogen, $C_1$-$C_{18}$alkyl, $C_2$-$C_{18}$alkyl which is interrupted by one or more of O, S, $NR_{14}$, CO, O(CO) or $NR_{14}$(CO), or is phenyl-$C_1$-$C_3$-alkyl or $C_1$-$C_{10}$haloalkyl, wherein said $C_1$-$C_{18}$alkyl, interrupted $C_2$-$C_{18}$alkyl, phenyl-$C_1$-$C_3$-alkyl or $C_1$-$C_{10}$haloalkyl are unsubstituted or are substituted by one or more identical or different $Z_1$;

or $R_1$ is $C_2$-$C_{12}$alkenyl or $C_2$-$C_{18}$alkenyl which is interrupted by one or more of O, S, $NR_{14}$, CO, O(CO), $NR_{14}$(CO) or $Z_3$, wherein said uninterrupted or interrupted $C_2$-$C_{12}$alkenyl is unsubstituted or substituted by one or more identical or different $Z_1$;

or $R_1$ is $C_3$-$C_{30}$cycloalkyl, $C_3$-$C_{30}$cycloalkyl-$C_1$-$C_{18}$alkyl or $C_4$-$C_{30}$cycloalkenyl, wherein said $C_3$-$C_{30}$cycloalkyl, $C_3$-$C_{30}$cycloalkyl-$C_1$-$C_{18}$alkyl or $C_4$-$C_{30}$cycloalkenyl is unsubstituted or substituted by one or more identical or different $Z_1$ and wherein said unsubstituted or substituted $C_3$-$C_{30}$cycloalkyl, $C_3$-$C_{30}$cycloalkyl-$C_1$-$C_{18}$alkyl or $C_4$-$C_{30}$cycloalkenyl optionally is interrupted by one or more identical or different O, S, $NR_{14}$, CO, O(CO) or $NR_{14}$(CO);

or $R_1$ is phenyl, naphthyl, anthracyl, phenanthryl, biphenylyl, fluorenyl or $C_3$-$C_{20}$heteroaryl wherein said phenyl, naphthyl, anthracyl, phenanthryl, biphenylyl, fluorenyl or $C_3$-$C_{20}$heteroaryl are unsubstituted or are substituted by one or more identical or different $Z_2$;

or $R_1$ is $NR_{12}R_{13}$ or a monovalent $C_{17}$-$C_{50}$ hydrocarbon group of steroid structure which may contain one or more heteroatoms;

$Z_3$ is phenylene, naphthylene, anthracylene, phenanthrylene, biphenylene or $C_3$-$C_{20}$heteroarylene, wherein said phenylene, naphthylene, anthracylene, phenanthrylene, biphenylene or $C_3$-$C_{20}$heteroarylene are unsubstituted or substituted by one or more identical or different $Z_1$;

$R_2$ and $R_3$ independently of each other are $C_1$-$C_{10}$haloalkylene, $C_1$-$C_{10}$haloalkylene substituted by one or more identical or different $Z_1$;

or $R_2$ and $R_3$ are $C_1$-$C_{18}$alkylene, $C_3$-$C_{30}$cycloalkylene, $C_3$-$C_{30}$cycloalkyl-$C_1$-$C_{18}$alkylene, $C_2$-$C_{12}$alkenylene or $C_4$-$C_{30}$cycloalkenylene wherein said $C_1$-$C_{18}$alkylene, $C_3$-$C_{30}$cycloalkylene, $C_3$-$C_{30}$cycloalkyl-$C_1$-$C_{18}$alkylene, $C_2$-$C_{12}$alkenylene or $C_4$-$C_{30}$cycloalkenylene is uninterrupted or interrupted by one or more identical or different O, S, $NR_{14}$, CO, O(CO) or $NR_{14}$(CO) and wherein said uninterrupted or interrupted $C_1$-$C_{18}$alkylene, $C_3$-$C_{30}$cycloalkylene, $C_3$-$C_{30}$cycloalkyl-$C_1$-$C_{18}$alkylene, $C_2$-$C_{12}$alkenylene or $C_4$-$C_{30}$cycloalkenylene is unsubstituted or substituted by one or more identical or different $Z_1$;

or $R_2$ and $R_3$ are phenylene, naphthylene, anthracylene, phenanthrylene, biphenylene or $C_3$-$C_{20}$heteroarylene, wherein said phenylene, naphthylene, anthracylene, phenanthrylene, biphenylene or $C_3$-$C_{20}$heteroarylene is unsubstituted or substituted by one or more identical or different $Z_2$;

or $R_2$ and $R_3$ independently of each other are a direct bond, provided that $R_2$ and $R_3$ are not both simultaneously a direct bond;

$R_4$ is a group

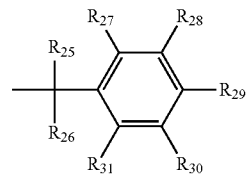

(A)

or a group

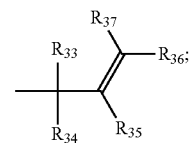

(B)

$R_5$ and $R_6$ independently of one another are unsubstituted $C_1$-$C_{20}$alkyl, $C_1$-$C_{20}$alkyl substituted by one or more identical or different $R_{2a}$, $C_2$-$C_{20}$alkyl interrupted by one or more non-adjacent O, S, C(O) or N($R_N$), wherein said interrupted $C_2$-$C_{20}$alkyl optionally is substituted by one or more identical or different $R_{2a}$, $C_2$-$C_{20}$alkenyl, $C_2$-$C_{20}$alkenyl substituted by one or more identical or different $R_{2a}$, wherein said unsubstituted or substituted $C_2$-$C_{20}$alkenyl optionally is interrupted by one or more non-adjacent O, S, C(O) or N($R_N$), or $R_5$ and $R_6$ are $C_2$-$C_{20}$alkynyl, $C_2$-$C_{20}$alkynyl substituted by one or more identical or different $R_{2a}$, wherein said unsubstituted or substituted $C_2$-$C_{20}$-alkynyl optionally is interrupted by one or more non-adjacent O, S, C(O) or N($R_N$), or $R_5$ and $R_6$ are $C_3$-$C_{20}$cycloalkyl, $C_3$-$C_{20}$cycloalkyl interrupted by one or more CO, and optionally substituted by one or more identical or different radicals $R_{2b}$, or $R_5$ and $R_6$ are $C_3$-$C_{20}$heterocycloalkyl, $C_3$-$C_{20}$heterocycloalkyl interrupted by one or more CO and optionally substituted by one or more identical or different radicals $R_{2b}$, or $R_5$ and $R_6$ are $C_6$-$C_{20}$aryl, $C_6$-$C_{20}$aryl substituted by one or more identical or different $R_{2c}$, or $R_5$ and $R_6$ are $C_3$-$C_{20}$heteroaryl, $C_3$-$C_{20}$heteroaryl substituted by one or more identical or different $R_{2c}$;

or $R_4$ and $R_5$ or $R_4$ and $R_6$ together form a straight-chain $C_2$-$C_6$alkylene, straight-chain $C_2$-$C_6$-alkenylene or a $(CH_2)_a$—$C_6H_4$—$(CH_2)_b$, wherein said $C_2$-$C_6$alkylene, $C_2$-$C_6$-alkenylene and the alkylene moiety of $(CH_2)_a$—$C_6H_4$—$(CH_2)_b$ optionally are substituted by one or more identical or different radicals $R_{32}$ and wherein said unsubstituted or substituted $C_2$-$C_6$alkylene, $C_2$-$C_6$-alkenylene and the alkylene moiety of $(CH_2)_a$—$C_6H_4$—$(CH_2)_b$ optionally are interrupted by one or more non-adjacent O, S, C(O) or N($R_N$);

or $R_5$ and $R_6$ together form a straight-chain $C_2$-$C_6$alkylene, a straight-chain $C_2$-$C_6$alkenylene, or a straight-chain $(CH_2)_c$—$C_6H_4$—$(CH_2)_d$, wherein said $C_2$-$C_6$alkylene, $C_2$-$C_6$alkenylene and the alkylene moiety of $(CH_2)_c$—$C_6H_4$—$(CH_2)_d$ optionally is substituted by one or more identical or different radicals $R_{32}$ and wherein said $C_2$-$C_6$alkylene, $C_2$-$C_6$alkenylene and the alkylene moiety of $(CH_2)_c$—$C_6H_4$—$(CH_2)_d$ optionally is fused to 1 or 2 phenyl rings; and wherein said $C_2$-$C_6$alkylene, $C_2$-$C_6$alkenylene and the alkylene moiety of $(CH_2)_c$—$C_6H_4$—$(CH_2)_d$ optionally is interrupted by one or more non-adjacent O, S, C(O) or $N(R_N)$;

a and b are an integer from 0 to 10 and the sum of a and b is 1 to 10;

c and d are an integer from 0 to 10 and the sum of c and d is 1 to 10;

$R_{2a}$ is F, Cl, Br, I, CN, $SR_{19}$, $OR_{20}$, $COR_{21}$, $COOR_{22}$, $CONR_{23}R_{24}$, $C_3$-$C_{20}$cycloalkyl, $C_3$-$C_{20}$cycloalkyl substituted by one or more identical or different $R_{2a}$, wherein the unsubstituted or substituted $C_3$-$C_{20}$cycloalkyl optionally is interrupted by one or more CO, or $R_{2a}$ is $C_3$-$C_{20}$heterocycloalkyl, $C_3$-$C_{20}$heterocycloalkyl substituted by one or more identical or different $R_{2ab}$, wherein the unsubstituted or substituted $C_3$-$C_{20}$heterocycloalkyl optionally is interrupted by one or more CO, or $R_{2a}$ is $C_3$-$C_{20}$heteroaryl or $C_6$-$C_{10}$aryl, where said $C_3$-$C_{20}$heteroaryl or $C_6$-$C_{10}$aryl optionally are substituted by one or more identical or different $R_{2ac}$;

$R_{2ab}$ is F, Cl, Br, I, $C_1$-$C_{12}$-alkyl, $C_1$-$C_{12}$-haloalkyl, CN, $SR_{19}$, $OR_{20}$, $COR_{21}$, $COOR_{22}$ or $CONR_{23}R_{24}$;

$R_{2ac}$ is F, Cl, Br, I, $C_1$-$C_{12}$alkyl, $C_1$-$C_{12}$haloalkyl, CN, $NO_2$, $SR_{19}$, $OR_{20}$, $COR_{21}$, $COOR_{22}$, $CONR_{23}R_{24}$;

$R_{2b}$ is F, Cl, Br, I, $C_1$-$C_{12}$alkyl, $C_1$-$C_{12}$haloalkyl, CN, $SR_{19}$, $OR_{20}$, $COR_{21}$, $COOR_{22}$, $CONR_{23}R_{24}$, $C_6$-$C_{10}$aryl or $C_3$-$C_{20}$heteroaryl where said $C_6$-$C_{10}$aryl or $C_3$-$C_{20}$heteroaryl optionally is substituted by one or more identical or different $R_{2ac}$;

$R_{2c}$ is F, Cl, Br, I, $C_1$-$C_{12}$alkyl, $C_1$-$C_{12}$haloalkyl, CN, $NO_2$, $SR_{19}$, $OR_{20}$, $COR_{21}$, $COOR_{22}$, $CONR_{23}R_{24}$, phenyl, $C_3$-$C_{20}$cycloalkyl or $C_3$-$C_{20}$heterocycloalkyl, wherein said $C_3$-$C_{10}$cycloalkyl or $C_3$-$C_{20}$heterocycloalkyl optionally are interrupted by one or more CO;

$R_7$, $R_8$, $R_9$ and $R_{10}$ independently of one another are $C_1$-$C_{20}$alkyl, $C_2$-$C_{20}$alkyl interrupted by one or more non-adjacent O, S, C(O) or $N(R_N)$, substituted by one or more identical or different $R_{2a}$, wherein said $C_1$-$C_{20}$alkyl or interrupted $C_2$-$C_{20}$alkyl optionally is substituted by one or more identical or different $R_{2a}$;

or $R_7$, $R_8$, $R_9$ and $R_{10}$ are $C_2$-$C_{20}$alkenyl, $C_2$-$C_{20}$alkenyl interrupted by one or more non-adjacent O, S, C(O) or $N(R_N)$, wherein said $C_2$-$C_{20}$alkenyl or interrupted $C_2$-$C_{20}$alkenyl optionally is substituted by one or more identical or different $R_{2a}$;

or $R_7$, $R_8$, $R_9$ and $R_{10}$ are $C_2$-$C_{20}$alkynyl, $C_2$-$C_{20}$alkynyl interrupted by one or more non-adjacent O, S, C(O) or $N(R_N)$, wherein said $C_2$-$C_{20}$alkynyl or interrupted $C_2$-$C_{20}$alkynyl optionally is substituted by one or more identical or different $R_{2a}$;

or $R_7$, $R_8$, $R_9$ and $R_{10}$ are $C_3$-$C_{20}$cycloalkyl, $C_3$-$C_{20}$cycloalkyl interrupted by one or more CO, wherein said $C_3$-$C_{20}$cycloalkyl or interrupted $C_3$-$C_{20}$cycloalkyl optionally is substituted by one or more identical or different $R_{2b}$;

or $R_7$, $R_8$, $R_9$ and $R_{10}$ are $C_3$-$C_{20}$heterocycloalkyl, $C_3$-$C_{20}$heterocycloalkyl interrupted by one or more CO, wherein said $C_3$-$C_{20}$heterocycloalkyl or interrupted $C_3$-$C_{20}$heterocycloalkyl optionally is substituted by one or more identical or different $R_{2b}$;

or $R_7$, $R_8$, $R_9$ and $R_{10}$ are $C_6$-$C_{20}$-aryl or $C_3$-$C_{20}$heteroaryl, wherein said $C_6$-$C_{20}$aryl and $C_3$-$C_{20}$heteroaryl optionally is substituted by one or more identical or different $R_{2c}$;

or $R_7$ and $R_8$ and/or $R_9$ and $R_{10}$ together form a straight-chain $C_2$-$C_6$alkylene, a straight-chain $C_2$-$C_6$alkenylene or a straight-chain $(CH_2)_c$—$C_6H_4$—$(CH_2)_d$, wherein said $C_2$-$C_6$alkylene, $C_2$-$C_6$alkenylene and the alkylene moiety of —$(CH_2)_c$—$C_6H_4$—$(CH_2)_d$ optionally is substituted by one or more identical or different $R_{32}$ and wherein said $C_2$-$C_6$alkylene, $C_2$-$C_6$alkenylene and the alkylene moiety of $(CH_2)_c$—$C_6H_4$—$(CH_2)_d$ optionally is fused to 1 or 2 phenyl rings, and wherein said $C_2$-$C_6$alkylene, $C_2$-$C_6$alkenylene and the alkylene moiety of $(CH_2)_c$—$C_6H_4$—$(CH_2)_d$ optionally is interrupted by one or more non-adjacent O, S, C(O) or $N(R_N)$;

M is $C_1$-$C_{20}$alkylene, $C_2$-$C_{20}$alkenylene, $C_2$-$C_{20}$alkynylene, wherein said $C_1$-$C_{20}$alkylene, $C_2$-$C_{20}$alkenylene or $C_2$-$C_{20}$alkynylene optionally is substituted by one or more identical or different $R_{Ma}$, and wherein said unsubstituted or substituted $C_1$-$C_{20}$alkylene, $C_2$-$C_{20}$alkenylene or $C_2$-$C_{20}$alkynylene optionally is interrupted by one or more identical or different non-adjacent $R_{Mi}$;

or M is $C_3$-$C_{20}$cycloalkylene or $C_3$-$C_{20}$heterocycloalkylene, wherein said $C_3$-$C_{20}$cycloalkylene or $C_3$-$C_{20}$heterocycloalkylene optionally is interrupted by one or more CO, and wherein said uninterrupted or interrupted $C_3$-$C_{20}$cycloalkylene or $C_3$-$C_{20}$heterocycloalkylene optionally is substituted by one or more identical or different $R_{Mb}$;

or M is $C_6$-$C_{20}$arylene or $C_3$-$C_{20}$heteroarylene, wherein said $C_6$-$C_{20}$arylene or $C_3$-$C_{20}$heteroarylene optionally is substituted by one or more identical or different $R_{Mc}$;

$R_{Mi}$ is O, S, C(O), OC(O) or $N(R_N)$, or $R_{Mi}$ is $C_3$-$C_{20}$cycloalkylene, O—$C_3$-$C_{20}$cycloalkylene, O—$C_3$-$C_{20}$cycloalkylene-O or $C_3$-$C_{20}$heterocycloalkylene, wherein said $C_3$-$C_{20}$cycloalkylene, O—$C_3$-$C_{20}$cycloalkylene, O—$C_3$-$C_{20}$cycloalkylene-O or $C_3$-$C_{20}$heterocycloalkylene optionally is interrupted by one or more CO groups and wherein said uninterrupted or interrupted $C_3$-$C_{20}$cycloalkylene, O—$C_3$-$C_{20}$cycloalkylene, O—$C_3$-$C_{20}$cycloalkylene-O or $C_3$-$C_{20}$heterocycloalkylene optionally is substituted by one or more identical or different $R_{Mib}$;

or $R_{Mi}$ is $C_6$-$C_{20}$arylene, O—$C_6$-$C_{20}$arylene, O—$C_6$-$C_{20}$arylene-O, S—$C_6$-$C_{20}$arylene, S—$C_6$-$C_{20}$arylene-S or $C_3$-$C_{20}$heteroarylene, wherein said is $C_6$-$C_{20}$arylene, O—$C_6$-$C_{20}$arylene, O—$C_6$-$C_{20}$arylene-O, S—$C_6$-$C_{20}$arylene, S—$C_6$-$C_{20}$arylene-S or $C_3$-$C_{20}$heteroarylene optionally is substituted by one or more $R_{Mib}$;

$R_{Ma}$ is F, Cl, Br, I, CN, $SR_{19}$, $OR_{20}$, $COR_{21}$, $COOR_{22}$ or $CONR_{23}R_{24}$, $C_6$-$C_{10}$aryl or $C_3$-$C_{20}$heteroaryl wherein said $C_6$-$C_{10}$aryl or $C_3$-$C_{20}$heteroaryl optionally is substituted by one or more identical or different radicals selected from $C_1$-$C_{12}$alkyl, $C_1$-$C_{12}$haloalkyl, F, Cl, Br, I, CN, $NO_2$, $SR_{19}$, $OR_{20}$, $COR_{21}$, $COOR_{22}$ or $CONR_{23}R_{24}$;

$R_{Mib}$ is F, Cl, Br, I, $C_1$-$C_{12}$alkyl, $C_1$-$C_{12}$haloalkyl, CN, $NO_2$, $SR_{19}$, $OR_{20}$, $COR_{21}$, $COOR_{22}$ or $CONR_{23}R_{24}$ or phenyl;

$R_{Mb}$ is F, Cl, Br, I, $C_1$-$C_{12}$alkyl, $C_1$-$C_{12}$haloalkyl, CN, $SR_{19}$, $OR_{20}$, $COR_{21}$, $COOR_{22}$ or $CONR_{23}R_{24}$, $C_6$-$C_{10}$aryl or $C_3$-$C_{20}$heteroaryl wherein said $C_6$-$C_{10}$aryl or $C_3$-$C_{20}$heteroaryl optionally is substituted by one or more identical or different radicals selected from $C_1$-$C_{12}$alkyl, $C_1$-$C_{12}$haloalkyl, F, Cl, Br, I, CN, $NO_2$, $SR_{19}$, $OR_{20}$, $COR_{21}$, $COOR_{22}$ and $CONR_{23}R_{24}$;

$R_{Mc}$ is F, Cl, Br, I, $C_1$-$C_{12}$alkyl, $C_1$-$C_{12}$haloalkyl, CN, $NO_2$, $SR_{19}$, $OR_{20}$, $COR_{21}$, $COOR_{22}$ or $CONR_{23}R_{24}$, phenyl, $C_3$-$C_{10}$cycloalkyl or $C_3$-$C_{20}$heterocycloalkyl, wherein said $C_3$-$C_{10}$cycloalkyl or $C_3$-$C_{20}$heterocycloalkyl optionally is interrupted by one or more CO; $R_{11}$ is hydrogen, $C_1$-$C_{18}$alkyl, $C_1$-$C_{10}$haloalkyl, $C_2$-$C_{12}$alkenyl, phenyl-$C_1$-$C_3$-alkyl; or $R_{11}$ is $C_2$-$C_{18}$alkyl which is interrupted by one or more of O, S, $NR_{11a}$, CO, O(CO) or $NR_{11a}$(CO);

or $R_{11}$ is $C_3$-$C_{30}$cycloalkyl, $C_3$-$C_{30}$cycloalkyl-$C_1$-$C_{18}$alkyl or $C_4$-$C_{30}$cycloalkenyl, wherein said $C_3$-$C_{30}$cycloalkyl, $C_3$-$C_{30}$cycloalkyl-$C_1$-$C_{18}$alkyl or $C_4$-$C_{30}$cycloalkenyl optionally is interrupted by one or more identical or different O, S, $NR_{11a}$, CO, O(CO) or $NR_{11a}$(CO); or $R_{11}$ is phenyl, naphthyl, anthracyl, phenanthryl, biphenyl, heteroaryl, $C_1$-$C_{18}$alkanoyl, benzoyl, $C_2$-$C_{18}$alkoxycarbonyl, phenoxycarbonyl, $C_1$-$C_{18}$alkylsulfonyl or phenylsulfonyl; wherein the $C_3$-$C_{30}$cycloalkyl, $C_3$-$C_{30}$cycloalkyl-$C_1$-$C_{18}$alkyl, $C_1$-$C_{18}$alkyl, $C_1$-$C_{10}$haloalkyl, $C_2$-$C_{12}$alkenyl, $C_4$-$C_{30}$cycloalkenyl, phenyl-$C_1$-$C_3$-alkyl, interrupted $C_2$-$C_{18}$alkyl, interrupted $C_3$-$C_{30}$cycloalkyl, interrupted $C_3$-$C_{30}$cycloalkyl-$C_1$-$C_{18}$alkyl, interrupted $C_4$-$C_{30}$cycloalkenyl, phenyl, naphthyl, anthracyl, phenanthryl, biphenyl, heteroaryl, $C_1$-$C_{18}$alkanoyl, benzoyl, $C_2$-$C_{18}$alkoxycarbonyl, phenoxycarbonyl, $C_1$-$C_{18}$alkylsulfonyl or phenylsulfonyl are unsubstituted or substituted one or more identical or different $Z_1$;

or $R_1$ and $R_{11}$, together with the nitrogen atom to which $R_{11}$ is attached, form a 5-, 6- or 7-membered ring which optionally is interrupted by one or more O, $NR_{11a}$ or CO;

$R_{12}$ and $R_{13}$ independently of each other are hydrogen, $C_1$-$C_{10}$haloalkyl, $C_2$-$C_{12}$alkenyl, phenyl-$C_1$-$C_3$-alkyl, $C_1$-$C_{18}$alkyl or $C_2$-$C_{18}$alkyl which is interrupted by one or more identical or different O, S, $NR_{11a}$ CO, O(CO) or $NR_{11a}$(CO) and wherein said $C_1$-$C_{10}$haloalkyl, $C_2$-$C_{12}$alkenyl, phenyl-$C_1$-$C_3$-alkyl, $C_1$-$C_{18}$alkyl or interrupted $C_2$-$C_{18}$alkyl is unsubstituted or substituted by one or more identical or different $Z_1$;

or $R_{12}$ and $R_{13}$ are $C_3$-$C_{30}$cycloalkyl, $C_3$-$C_{30}$cycloalkyl-$C_1$-$C_{18}$alkyl or $C_4$-$C_{30}$cycloalkenyl, wherein said $C_3$-$C_{30}$cycloalkyl, $C_3$-$C_{30}$cycloalkyl-$C_1$-$C_{18}$alkyl or $C_4$-$C_{30}$cycloalkenyl optionally is interrupted by one or more identical or different O, S, $NR_{11a}$, CO, O(CO) or $NR_{11a}$(CO) and wherein said uninterrupted or interrupted $C_3$-$C_{30}$cycloalkyl, $C_3$-$C_{30}$cycloalkyl-$C_1$-$C_{18}$alkyl or $C_4$-$C_{30}$cycloalkenyl are unsubstituted or substituted by one or more identical or different $Z_1$;

or $R_{12}$ and $R_{13}$ independently of each other are $(CO)R_{21}$, $(CO)OR_{21}$ or Ar which is unsubstituted or substituted by one or more identical or different $Z_1$;

or $R_{12}$ and $R_{13}$, together with the nitrogen atom to which they are attached, form a 5-, 6- or 7-membered ring which optionally is interrupted by one or more O, $NR_{11a}$ or CO;

$R_{11a}$ is hydrogen, $C_1$-$C_{10}$haloalkyl, $C_2$-$C_{12}$alkenyl, phenyl-$C_1$-$C_3$-alkyl, $C_1$-$C_{18}$alkyl or $C_2$-$C_{18}$alkyl which is interrupted by one or more of O, S, CO or O(CO), wherein said $C_2$-$C_{12}$alkenyl, phenyl-$C_1$-$C_3$-alkyl, $C_1$-$C_{18}$alkyl or interrupted $C_2$-$C_{18}$alkyl is unsubstituted or substituted by one or more identical or different $Z_1$;

or $R_{11a}$ is $C_3$-$C_{30}$cycloalkyl, $C_3$-$C_{30}$cycloalkyl-$C_1$-$C_{18}$alkyl or $C_4$-$C_{30}$cycloalkenyl wherein said $C_3$-$C_{30}$cycloalkyl, $C_3$-$C_{30}$cycloalkyl-$C_1$-$C_{18}$alkyl or $C_4$-$C_{30}$cycloalkenyl optionally is interrupted by one or more identical or different O, S, CO or O(CO) and wherein said uninterrupted or interrupted $C_3$-$C_{30}$cycloalkyl, $C_3$-$C_{30}$cycloalkyl-$C_1$-$C_{18}$alkyl or $C_4$-$C_{30}$cycloalkenyl is unsubstituted or substituted by one or more identical or different $Z_1$;

or $R_{11a}$ is phenyl, naphthyl, anthracyl, phenanthryl, biphenylyl, $C_3$-$C_{20}$heteroaryl, $C_1$-$C_{18}$alkanoyl, benzoyl, $C_2$-$C_{18}$alkoxycarbonyl, phenoxycarbonyl, $C_1$-$C_{18}$alkylsulfonyl or phenylsulfonyl, wherein said phenyl, naphthyl, anthracyl, phenanthryl, biphenylyl, $C_3$-$C_{20}$heteroaryl, $C_1$-$C_{18}$alkanoyl, benzoyl, $C_2$-$C_{18}$alkoxycarbonyl, phenoxycarbonyl, $C_1$-$C_{18}$alkylsulfonyl or phenylsulfonyl is unsubstituted or substituted one or more identical or different $Z_2$;

$R_{14}$ is hydrogen, Ar, $C_1$-$C_{10}$haloalkyl, $C_2$-$C_{12}$alkenyl, phenyl-$C_1$-$C_3$-alkyl, $C_1$-$C_{18}$alkyl or $C_2$-$C_{18}$alkyl which is interrupted by one or more identical or different O, S, $NR_{11a}$, CO, O(CO) or $NR_{11a}$(CO), wherein said Ar, $C_1$-$C_{10}$haloalkyl, $C_2$-$C_{12}$alkenyl, phenyl-$C_1$-$C_3$-alkyl, $C_1$-$C_{18}$alkyl or interrupted $C_2$-$C_{18}$alkyl is unsubstituted or substituted by one or more identical or different $Z_1$;

or $R_{14}$ is $C_3$-$C_{30}$cycloalkyl, $C_3$-$C_{30}$cycloalkyl-$C_1$-$C_{18}$alkyl or $C_4$-$C_{30}$cycloalkenyl wherein said $C_3$-$C_{30}$cycloalkyl, $C_3$-$C_{30}$cycloalkyl-$C_1$-$C_{18}$alkyl or $C_4$-$C_{30}$cycloalkenyl optionally is interrupted by one or more identical or different O, S, $NR_{11a}$, CO, O(CO) or $NR_{11a}$(CO) and wherein said uninterrupted or interrupted $C_3$-$C_{30}$cycloalkyl, $C_3$-$C_{30}$cycloalkyl-$C_1$-$C_{18}$alkyl or $C_4$-$C_{30}$cycloalkenyl is unsubstituted or substituted by one or more identical or different $Z_1$;

Ar is phenyl, biphenylyl, fluorenyl, naphthyl, anthracyl, phenanthryl or heteroaryl, wherein said phenyl, biphenylyl, fluorenyl, naphthyl, anthracyl, phenanthryl or heteroaryl are unsubstituted or substituted one or more identical or different $Z_2$;

$Z_1$ is Ar, OH, $C_1$-$C_{18}$alkyl, $C_1$-$C_{10}$haloalkyl, phenyl-$C_1$-$C_3$-alkyl, $C_3$-$C_{30}$cycloalkyl, halogen, $NO_2$, CN, $C_1$-$C_{18}$alkoxy, phenoxy, phenoxycarbonyl, phenylthio, phenylthiocarbonyl, $NR_{12}R_{13}$, $C_1$-$C_{12}$alkylthio, $C_2$-$C_{18}$alkoxycarbonyl, $C_2$-$C_{10}$haloalkanoyl, halobenzoyl, $C_1$-$C_{18}$alkylsulfonyl, phenylsulfonyl, (4-methylphenyl)sulfonyl, $C_1$-$C_{18}$alkylsulfonyloxy, phenylsulfonyloxy, (4-methylphenyl)sulfonyloxy, $C_1$-$C_{18}$alkanoyl, $C_1$-$C_{18}$alkanoyloxy, benzoyl and/or by benzoyloxy;

$Z_2$ is $C_1$-$C_{18}$alkyl, $C_2$-$C_{18}$alkyl which is interrupted by one or more of O, S, $NR_{11a}$, CO, O(CO) or $NR_{11a}$(CO);

or $Z_2$ is $C_3$-$C_{30}$cycloalkyl, $C_3$-$C_{30}$cycloalkyl-$C_1$-$C_{18}$alkyl or $C_4$-$C_{30}$cycloalkenyl, wherein said $C_3$-$C_{30}$cycloalkyl, $C_3$-$C_{30}$cycloalkyl-$C_1$-$C_{18}$alkyl or $C_4$-$C_{30}$cycloalkenyl optionally is interrupted by one or more identical or different O, S, $NR_{11a}$, CO, O(CO) or $NR_{11a}$(CO); or $Z_2$ is $C_1$-$C_{10}$haloalkyl, $C_2$-$C_{12}$alkenyl, phenyl-$C_1$-$C_3$-alkyl, halogen, $NO_2$, CN, $(CO)R_{21}$, $(CO)OR_{22}$, $(CO)NR_{12}R_{13}$, $O(CO)R_{21}$, $O(CO)OR_{22}$, $O(CO)NR_{12}R_{13}$, $NR_{11a}(CO)R_{21}$, $NR_{11a}(CO)OR_{21}$, $NR_{11a}(CO)NR_{12}R_{13}$, $OR_{20}$, $NR_{12}R_{13}$, $SR_{11a}$, phenyl, biphenylyl, fluorenyl, naphthyl, anthracyl, phenanthryl and/or heteroaryl;

$R_{19}$ and $R_{20}$ independently of one another are hydrogen, $C_1$-$C_{20}$alkyl, $C_2$-$C_{12}$alkenyl, $C_3$-$C_{10}$cycloalkyl or $C_3$-$C_{20}$heterocycloalkyl, wherein said $C_3$-$C_{10}$cycloalkyl or $C_3$-$C_{20}$heterocycloalkyl optionally are interrupted by one or more CO;

or $R_{19}$ and $R_{20}$ are $C_2$-$C_{20}$alkyl which is interrupted by one or more non-adjacent O, S, C(O) or $N(R_N)$;

or $R_{19}$ and $R_{20}$ are $C_1$-$C_8$-alkyl substituted by one or more identical or different $R_{19a}$;

or $R_{19}$ and $R_{20}$ are $-(CH_2CH_2O)_mH$, $-(CH_2CH_2O)_m(CO)-(C_1$-$C_8$-alkyl), $C_2$-$C_8$-alkanoyl, $C_2$-$C_8$-haloalkanoyl, $C_3$-$C_6$-alkenoyl, benzoyl or benzoyl which is substituted by one or more identical or different F, Cl, Br, I, $C_1$-$C_6$-alkyl, OH or $C_1$-$C_4$-alkoxy;

or $R_{19}$ and $R_{20}$ are phenyl, naphthyl, both of which optionally are substituted by one or more identical or different $R_{19c}$;

or $R_{19}$ and $R_{20}$ are phenyl or naphthyl which forms a 5- or 6-membered ring via the phenyl ring to which $SR_{19}$ or $OR_{20}$, respectively, is attached via a single bond, $C_1$-$C_4$alkylene, O, S, CO or $NR_{23}$;

m is 1-20;

$R_{19a}$ is F, Cl, Br, I, OH, SH, CN, $C_3$-$C_{10}$cycloalkyl, $C_3$-$C_{20}$heterocycloalkyl, phenyl, $C_3$-$C_6$alkenoxy, —OCH$_2$CH$_2$CN, —OCH$_2$CH$_2$(CO)O($C_1$-$C_8$alkyl), —O(CO)—($C_1$-$C_8$alkyl), —O(CO)-phenyl, —(CO)OH or —(CO)O($C_1$-$C_8$alkyl);

$R_{19c}$ is F, Cl, Br, I, $C_1$-$C_{12}$alkyl, $C_1$-$C_{12}$haloalkyl, $C_1$-$C_{12}$alkoxy, phenyl-$C_1$-$C_3$alkyloxy, phenoxy, $C_1$-$C_{12}$alkylsulfanyl, phenylsulfanyl, —(CO)O($C_1$-$C_8$alkyl), (CO)N($C_1$-$C_8$alkyl)$_2$ or phenyl;

$R_{21}$ is hydrogen, $C_1$-$C_{20}$alkyl, $C_2$-$C_{12}$alkenyl, $C_1$-$C_{20}$-alkyl which is interrupted by one or more non-adjacent O, S, CO or N($R_N$);

or $R_{21}$ is $C_1$-$C_8$alkyl substituted by one or more identical or different $R_{21a}$, or $R_{21}$ is —(CH$_2$CH$_2$O)$_m$H, —(CH$_2$CH$_2$O)$_m$(CO)—($C_1$-$C_8$-alkyl), $C_3$-$C_{10}$cycloalkyl or $C_3$-$C_{20}$heterocycloalkyl, wherein said $C_3$-$C_{10}$cycloalkyl or $C_3$-$C_{20}$heterocycloalkyl optionally is interrupted by one or more CO;

or $R_{21}$ is $C_6$-$C_{20}$aryl or $C_3$-$C_{20}$heteroaryl, both of which optionally are substituted by one or more radicals identical or different $R_{19c}$;

$R_{21a}$ is F, Cl, Br, I, OH, SH, CN, phenyl, $C_3$-$C_6$alkenoxy, —OCH$_2$CH$_2$CN, —OCH$_2$CH$_2$(CO)O($C_1$-$C_8$alkyl), —O(CO)—($C_1$-$C_8$alkyl), —O(CO)-phenyl, —(CO)OH or —(CO)O($C_1$-$C_8$alkyl);

$R_{22}$ is hydrogen, $C_1$-$C_{20}$alkyl, $C_2$-$C_{12}$alkenyl, $C_2$-$C_{20}$alkyl which is interrupted by one or more non-adjacent O, S, C(O) or N($R_N$), or $R_{22}$ is $C_1$-$C_{18}$alkyl substituted by one or more identical or different $R_{22a}$, or $R_{22}$ is —(CH$_2$CH$_2$O)$_m$H, —(CH$_2$CH$_2$O)$_m$(CO)—($C_1$-$C_8$alkyl), $C_3$-$C_{10}$cycloalkyl, $C_3$-$C_{20}$heteroycloalkyl, wherein said $C_3$-$C_{10}$cycloalkyl, $C_3$-$C_{20}$heteroycloalkyl optionally are interrupted by one or more CO;

or $R_{22}$ is phenyl or naphthyl, both of which optionally are substituted by one or more identical or different $R_{19c}$;

$R_{22a}$ is F, Cl, Br, I, OH, SH, CN, $C_3$-$C_6$alkenoxy, —OCH$_2$CH$_2$CN, —OCH$_2$CH$_2$(CO)O($C_1$-$C_8$alkyl), —O(CO)—($C_1$-$C_8$alkyl), —O(CO)-phenyl, —(CO)OH, —(CO)O($C_1$-$C_8$-alkyl), phenyl or naphthyl, wherein said phenyl or naphthyl optionally are substituted by one or more identical or different $R_{19c}$;

$R_{23}$ and $R_{24}$ independently of one another are hydrogen, $OR_{20}$, $C_1$-$C_{20}$alkyl, $C_2$-$C_{12}$alkenyl, $C_2$-$C_{20}$alkyl which is interrupted by one or more non-adjacent O, S, C(O) or N($R_N$);

or $R_{23}$ and $R_{24}$ are $C_1$-$C_8$-alkyl substituted by one or more identical or different $R_{23a}$;

or $R_{23}$ and $R_{24}$ are —(CH$_2$CH$_2$O)$_m$H, —(CH$_2$CH$_2$O)$_m$(CO)—($C_1$-$C_8$alkyl), $C_2$-$C_8$alkanoyl, $C_2$-$C_8$-haloalkanoyl, $C_3$-$C_6$-alkenoyl, benzoyl, benzoyl which is substituted by one or more identical or different F, Cl, Br, I, $C_1$-$C_6$alkyl, OH or $C_1$-$C_4$alkoxy;

or $R_{23}$ and $R_{24}$ are $C_3$-$C_{10}$cycloalkyl or $C_3$-$C_{20}$heterocycloalkyl, wherein said $C_3$-$C_{10}$cycloalkyl or $C_3$-$C_{20}$heterocycloalkyl optionally are interrupted by one or more CO;

or $R_{23}$ and $R_{24}$ are phenyl or naphthyl both of which optionally are substituted by one or more identical or different $R_{19c}$;

$R_{23a}$ is F, Cl, Br, I, OH, SH, CN, phenyl, $C_3$-$C_6$alkenoxy, —OCH$_2$CH$_2$CN, —OCH$_2$CH$_2$(CO)O($C_1$-$C_8$alkyl), —O(CO)—($C_1$-$C_8$alkyl), —O(CO)-phenyl, —(CO)OH or —(CO)O($C_1$-$C_8$alkyl);

or $R_{23}$ and $R_{24}$ together form a $C_2$-$C_5$alkylene group, which optionally is interrupted by one or more non-adjacent O, S, C(O) or N($R_N$);

$R_{25}$ and $R_{26}$ independently of one another are hydrogen, F, Cl, Br, I, CN, NO$_2$, $SR_{19}$, $OR_{20}$, $COR_{21}$, $COOR_{22}$, $CONR_{23}R_{24}$, $C_1$-$C_{20}$alkyl, $C_2$-$C_{20}$alkyl which is interrupted by one or more non-adjacent O, S, C(O) or N($R_N$) and wherein said uninterrupted $C_1$-$C_{20}$alkyl or interrupted $C_2$-$C_{20}$alkyl optionally is substituted by one or more identical or different $R_{2a}$;

or $R_{25}$ and $R_{26}$ are $C_3$-$C_{20}$cycloalkyl or $C_3$-$C_{20}$heterocycloalkyl, wherein said $C_3$-$C_{20}$cycloalkyl or $C_3$-$C_{20}$heterocycloalkyl optionally is interrupted by one or more CO and wherein said uninterrupted or interrupted $C_3$-$C_{20}$cycloalkyl or $C_3$-$C_{20}$heterocycloalkyl optionally is substituted by one or more identical or different $R_{2b}$;

or $R_{25}$ and $R_{26}$ are $C_6$-$C_{20}$-aryl or $C_3$-$C_{20}$heteroaryl, wherein said $C_6$-$C_{20}$-aryl or $C_3$-$C_{20}$heteroaryl optionally is substituted by one or more identical or different $R_{2c}$;

$R_{27}$, $R_{28}$, $R_{29}$, $R_{30}$ and $R_{31}$ independently of one another are hydrogen, F, Cl, Br, I, CN, NO$_2$, $SR_{19}$, $OR_{20}$, $COR_{21}$, $COOR_{22}$, $CONR_{23}R_{24}$, $C_1$-$C_{20}$alkyl, $C_2$-$C_{20}$alkyl which is interrupted by one or more non-adjacent O, S, C(O) or N($R_N$), wherein said $C_1$-$C_{20}$alkyl or interrupted $C_2$-$C_{20}$alkyl optionally is substituted one or more identical or different $R_{2a}$;

or $R_{27}$, $R_{28}$, $R_{29}$, $R_{30}$ and $R_{31}$ are $C_2$-$C_{20}$alkenyl or $C_2$-$C_{20}$alkynyl, wherein said $C_2$-$C_{20}$alkenyl or $C_2$-$C_{20}$alkynyl optionally are substituted one or more identical or different $R_{2a}$ and wherein said unsubstituted or substituted $C_2$-$C_{20}$alkenyl or $C_2$-$C_{20}$alkynyl optionally is interrupted by one or more non-adjacent O, S, C(O) or N($R_N$);

or $R_{27}$, $R_{28}$, $R_{29}$, $R_{30}$ and $R_{31}$ are $C_3$-$C_{20}$cycloalkyl or $C_3$-$C_{20}$heterocycloalkyl, wherein said $C_3$-$C_{20}$cycloalkyl or $C_3$-$C_{20}$heterocycloalkyl optionally is interrupted by one or more CO and wherein said $C_3$-$C_{20}$cycloalkyl or $C_3$-$C_{20}$heterocycloalkyl optionally is substituted by one or more identical or different $R_{2b}$;

or $R_{27}$, $R_{28}$, $R_{29}$, $R_{30}$ and $R_{31}$ are $C_6$-$C_{20}$aryl or $C_3$-$C_{20}$heteroaryl, wherein said $C_6$-$C_{20}$aryl or $C_3$-$C_{20}$heteroaryl optionally is substituted by one or more identical or different $R_{2c}$; or two radicals $R_{27}$ and $R_{28}$, $R_{29}$ and $R_{29}$, $R_{29}$ and $R_{30}$ and/or $R_{30}$ and $R_{31}$ together form a straight-chain $C_2$-$C_6$alkylene or a straight-chain $C_2$-$C_6$alkenylene, wherein said $C_2$-$C_6$alkylene or $C_2$-$C_6$alkenylene optionally is substituted by one or more identical or different $R_{32}$ and wherein said unsubstituted or substituted $C_2$-$C_6$alkenylene optionally is fused to 1 or 2 $C_6$-$C_{10}$aryl rings and wherein said unsubstituted or substituted, unfused or fused $C_2$-$C_6$alkenylene optionally is interrupted by one or more non-adjacent O, S, C(O) or N($R_N$);

or $R_{25}$ and $R_{27}$ together form $C_2$-$C_6$alkylene, wherein said $C_2$-$C_6$alkylene optionally is substituted by one or more $R_{32}$ and wherein said unsubstituted or substituted $C_2$-$C_6$alkylene optionally is interrupted by one or more non-adjacent O, S, C(O) or N($R_N$), or $R_{25}$ and $R_{27}$ together form 1,2-phenylene, wherein said 1,2-phenylene optionally is substituted by one or more identical or different $R_{32}$;

$R_{32}$ is F, Cl, Br, I, CN, $NO_2$, $SR_{19}$, $OR_{20}$, $COR_{21}$, $COOR_{22}$, $CONR_{23}R_{24}$, $C_1$-$C_{20}$alkyl, $C_2$-$C_{20}$alkenyl or $C_2$-$C_{20}$alkynyl;

or $R_{32}$ is $C_2$-$C_{20}$alkyl, $C_2$-$C_{20}$alkenyl or $C_2$-$C_{20}$-alkynyl which is interrupted by one or more non-adjacent O, S, C(O) or N($R_N$), wherein said uninterrupted $C_1$-$C_{20}$alkyl, $C_2$-$C_{20}$alkenyl, $C_2$-$C_{20}$alkynyl or said interrupted $C_2$-$C_{20}$alkyl, $C_2$-$C_{20}$alkenyl or $C_2$-$C_{20}$-alkynyl optionally is substituted one or more identical or different $R_{32a}$, or $R_{32}$ is $C_3$-$C_{20}$cycloalkyl or $C_3$-$C_{20}$heterocycloalkyl, wherein said $C_3$-$C_{20}$cycloalkyl or $C_3$-$C_{20}$heterocycloalkyl optionally is interrupted by one or more CO and wherein said interrupted or uninterrupted $C_3$-$C_{20}$cycloalkyl or $C_3$-$C_{20}$heterocycloalkyl optionally is substituted by one or more identical or different $R_{32b}$;

or $R_{32}$ is $C_6$-$C_{20}$aryl or $C_3$-$C_{20}$heteroaryl, both of which optionally are substituted by one or more identical or different $R_{32c}$;

$R_{32a}$ is F, Cl, Br, I, CN, $SR_{19}$, $OR_{20}$, $COR_{21}$, $COOR_{22}$, $CONR_{23}R_{24}$, $C_3$-$C_{20}$cycloalkyl or $C_3$-$C_{20}$heterocycloalkyl wherein $C_3$-$C_{20}$cycloalkyl or $C_3$-$C_{20}$heterocycloalkyl optionally is interrupted by one or more CO and wherein said uninterrupted or interrupted $C_3$-$C_{20}$cycloalkyl or $C_3$-$C_{20}$heterocycloalkyl optionally is substituted by one or more identical or different $R_{2ab}$;

or $R_{32a}$ is phenyl or phenyl which is substituted by one or more identical or different $R_{2ac}$;

$R_{32b}$ is F, Cl, Br, I, $C_1$-$C_{12}$alkyl, $C_1$-$C_{12}$-haloalkyl, CN, $SR_{19}$, $OR_{20}$, $COR_{21}$, $COOR_{22}$, $CONR_{23}R_{24}$, phenyl or phenyl which is substituted by one or more identical or different $R_{2ac}$;

$R_{32c}$ is F, Cl, Br, I, $C_1$-$C_{12}$alkyl, $C_1$-$C_{12}$haloalkyl, CN, $NO_2$, $SR_{19}$, $OR_{20}$, $COR_{21}$, $COOR_{22}$, $CONR_{23}R_{24}$, phenyl, $C_3$-$C_{10}$cycloalkyl or $C_3$-$C_{20}$heterocycloalkyl, wherein said $C_3$-$C_{10}$cycloalkyl or $C_3$-$C_{20}$heterocycloalkyl optionally is interrupted by one or more CO;

$R_N$ is hydrogen, $C_1$-$C_{20}$alkyl, $C_1$-$C_{10}$alkanoyl, $C_6$-$C_{10}$aroyl, $C_1$-$C_{20}$alkylsulfonyl, $C_2$-$C_{20}$alkenylsulfonyl, $C_6$-$C_{10}$arylsulfonyl, $C_6$-$C_{10}$aryl, $C_3$-$C_{20}$heteroaryl, $C_3$-$C_{10}$cycloalkyl or $C_3$-$C_{20}$heterocycloalkyl wherein said $C_3$-$C_{10}$cycloalkyl or $C_3$-$C_{20}$heterocycloalkyl optionally are interrupted by one or more CO;

$R_{33}$ and $R_{34}$ independently of one another are hydrogen, F, Cl, Br, I, CN, $NO_2$, $SR_{19}$, $OR_{20}$, $COR_{21}$, $COOR_{22}$, $CONR_{23}R_{24}$, $C_1$-$C_{20}$alkyl, $C_2$-$C_{20}$alkyl which is interrupted by one or more non-adjacent O, S, C(O) or N($R_N$), wherein said $C_1$-$C_{20}$-alkyl or interrupted $C_2$-$C_{20}$alkyl optionally is substituted by one or more $R_{2a}$;

or $R_{33}$ and $R_{34}$ are $C_3$-$C_{20}$cycloalkyl or $C_3$-$C_{20}$heterocycloalkyl, where said $C_3$-$C_{20}$cycloalkyl or $C_3$-$C_{20}$heterocycloalkyl optionally is interrupted by one or more CO and wherein said $C_3$-$C_{20}$cycloalkyl or $C_3$-$C_{20}$heterocycloalkyl optionally is substituted by one or more identical or different $R_{2b}$;

or $R_{33}$ and $R_{34}$ are $C_6$-$C_{20}$aryl or $C_3$-$C_{20}$heteroaryl, wherein $C_6$-$C_{20}$aryl or $C_3$-$C_{20}$heteroaryl optionally is substituted by one or more identical or different $R_{2c}$;

$R_{35}$, $R_{36}$ and $R_{37}$ independently of one another are hydrogen, F, Cl, Br, I, CN, $NO_2$, $SR_{19}$, $OR_{20}$, $COR_{21}$, $COOR_{22}$, $CONR_{23}R_{24}$, $C_1$-$C_{20}$alkyl, $C_2$-$C_{20}$alkyl which is interrupted by one or more non-adjacent O, S, C(O) or N($R_N$), wherein said $C_1$-$C_{20}$alkyl or interrupted $C_2$-$C_{20}$alkyl optionally is substituted by one or more $R_{2a}$;

or $R_{35}$, $R_{36}$ and $R_{37}$ are $C_2$-$C_{20}$alkenyl or $C_2$-$C_{20}$alkynyl, wherein said $C_2$-$C_{20}$alkenyl or $C_2$-$C_{20}$-alkynyl optionally is substituted by one or more identical or different $R_{2a}$ and wherein said unsubstituted or substituted $C_2$-$C_{20}$alkenyl or $C_2$-$C_{20}$alkynyl optionally is interrupted by one or more non-adjacent O, S, C(O) or N($R_N$);

or $R_{35}$, $R_{36}$ and $R_{37}$ are $C_3$-$C_{20}$cycloalkyl or $C_3$-$C_{20}$heterocycloalkyl, wherein said $C_3$-$C_{20}$cycloalkyl or $C_3$-$C_{20}$heterocycloalkyl optionally is substituted by one or more identical or different $R_{2b}$;

or $R_{35}$, $R_{36}$ and $R_{37}$ are $C_6$-$C_{20}$aryl or $C_3$-$C_{20}$heteroaryl, wherein optionally is substituted by one or more identical or different $R_{2c}$;

or $R_{35}$ and $R_{36}$ together form straight-chain $C_2$-$C_6$alkylene or a straight-chain $C_2$-$C_6$alkenylene, wherein said $C_2$-$C_6$alkylene or $C_2$-$C_6$alkenylene optionally is substituted by one or more identical or different $R_{32}$ and wherein said $C_2$-$C_6$alkylene or $C_2$-$C_6$alkenylene optionally is interrupted by one or more non-adjacent O, S, C(O) or N($R_N$);

or two radicals $R_{33}$ and $R_{35}$, $R_{33}$ and $R_{37}$, $R_{34}$ and $R_{35}$ and/or $R_{34}$ and $R_{37}$ together form straight-chain $C_2$-$C_6$alkylene or $C_2$-$C_6$alkenylene, wherein said $C_2$-$C_6$alkylene or $C_2$-$C_6$alkenylene optionally is substituted by one or more identical or different $R_{32}$ and wherein said unsubstituted or substituted $C_2$-$C_6$alkylene optionally is interrupted by one or more non-adjacent groups O, S, C(O), C(O)O, C(O)N($R_N$) or N($R_N$).

The invention further provides heat-curable composition comprising (a) at least one compound which is capable of undergoing cationic polymerization; and (b) at least one compound of the formula I, Ia or Ib as defined above.

In a further aspect, the invention provides a method for curing a cationic polymerizable-composition, which method comprises applying a composition comprising (a) at least one compound which is capable of undergoing cationic polymerization, preferably a compound having at least one group selected from an epoxy group, oxetane group and vinyl ether group; and (b) at least one sulfonium sulfonate selected from compounds of the formula I, Ia or Ib as defined above, to a substrate and exposing the composition to treatment with heat.

In a further aspect, the invention provides the use of the compounds of the formula I, Ia or Ib as thermal acid generator compound. A thermal acid generator compound is meant to be a compound which generates an acid upon treatment with heat.

The invention further provides the use of a composition as defined above for the production of a layer or a component of a flat panel display such as liquid crystal display, OLED display and plasma display panel; as well as the use for producing an overcoat layer of a colour filter or an insulating layer or a dielectric layer.

Another aspect of the invention is the use of the composition as defined above for producing pigmented and non-pigmented paints, printing inks, printing plates, adhesives, dental compositions or gel coats.

Another subject of the invention is the method as described above for the production of a layer or a component of a flat panel display and the method as described above for producing an overcoat layer of a colour filter or an insulating layer or a dielectric layer.

A further subject of the invention is a substrate which is coated on at least one surface with a composition as defined above.

The term "steroisomers" encompasses both optical isomers, such as enantiomers or diastereomers, the latter existing due to more than one center of chirality in the molecule, as well as geometrical isomers (cis/trans isomers). Depending on the substitution pattern, the compounds of the formulae Ia and Ib may have one or more centers of chirality, in which case they are present as mixtures of enantiomers or diastereomers. The invention provides both the pure enantiomers or diastereomers and their mixtures and the use according to the invention of the pure enantiomers or diastereomers of the compound Ia and Ib or its mixtures. Suitable compounds of the formulae Ia and Ib also include all possible geometrical stereoisomers (cis/trans isomers) and mixtures thereof. Cis/trans isomers may be present with respect to a carbon-carbon double bond.

For the purpose of the present invention the term halogen denotes fluorine, chlorine, bromine or iodine, particularly fluorine or chlorine.

The term "alkyl" as used herein refers to saturated straight-chain or branched hydrocarbon radicals having usually 1 to 4, to 6, to 8, to 12, to 16 or to 20 carbon atoms. Alkyl is preferably $C_1$-$C_{12}$-alkyl and more preferably $C_1$-$C_8$-alkyl. Examples of alkyl groups are especially methyl, ethyl, n-propyl, isopropyl, n-butyl, isobutyl, sec-butyl, tert-butyl, n-pentyl, neo-pentyl, n-hexyl, n-heptyl, n-octyl, n-nonyl, n-decyl, n-undecyl, n-dodecyl, n-tridecyl, n-tetradecyl, n-hexadecyl, n-octadecyl and n-eicosyl.

Alkyl radicals interrupted by non-adjacent groups selected from O, S C(O) and N($R_N$) may be interrupted by one or more, e.g. 1, 2, 3, 4, 5, 6, 7, 8 or more than 8 of the above-mentioned groups, i.e, the termini of the alkyl group are formed by carbon atoms. $R_N$ is as defined above. If a plurality of those interrupting groups selected from O, S and N($R_N$) occurs in the radical alkyl, those heteroatoms are usually identical. Examples for alkyl interrupted by one or more O-atoms are —$CH_2$—O—$CH_3$, —$CH_2CH_2$—O—$CH_2CH_3$, —[$CH_2CH_2O$]$_y$—$CH_3$, with y=1-9, —($CH_2CH_2O$)$_7CH_2CH_3$, —$CH_2$—CH($CH_3$)—O—$CH_2$—$CH_2CH_3$, and —$CH_2$—CH($CH_3$)—O—$CH_2CH_3$. A skilled person will readily understand that alkyl interrupted by 1 oxygen atom may also be referred to as alkoxy-alkyl or alkyl interrupted by 2 oxygen atoms may also be referred to as alkoxy-alkoxy-alkyl. Likewise, alkyl interrupted by 1 sulfur atom may also be referred to as alkyl-S-alkyl (alkylsulfanyl-alkyl) or, alkyl interrupted by 2 sulfur atoms may also be referred to as alkyl-S-alkyl-S-alkyl (alkylsulfanyl-alkylsulfanyl-alkyl).

Substituted alkyl groups may, depending on the length of the alkyl chain, have one or more (e.g. 1, 2, 3, 4, 5 or more than 5) identical or different substituents. In the case of halogen substituted alkyl, the alkyl group can be partially of fully halogenated and/or may carry further substituents.

Examples for haloalkyl are $C_1$-$C_{20}$-fluoroalkyl, $C_1$-$C_{20}$ chloroalkyl and $C_1$-$C_{20}$-bromoalkyl, such as chloromethyl, trichloromethyl, fluoromethyl, difluoromethyl, trifluoromethyl, 2,2,2,-trifluoroethyl and 2-bromopropyl.

An example for alkyl substituted by cycloalkyl, where cycloalkyl is interrupted by one CO group and carries one or more alkyl groups is camphoryl, especially camphor-10-yl

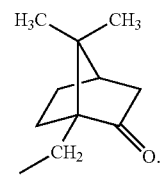

The term "alkoxy" as used herein refers to a saturated straight-chain or branched, alkyl radical having usually 1 to 4, to 6, to 8, to 12, to 16 or to 20 carbon atoms which is attached via an oxygen atom to the remainder of the molecule. Examples are methoxy, ethoxy, propoxy, isopropoxy, n-butyloxy, sec-butyloxy, iso-butyloxy, tert-butyloxy, pentyloxy, hexyloxy, heptyloxy, 2,4,4-trimethylpentyloxy, 2-ethyihexyloxy, octyloxy, nonyloxy, decyloxy, dodecyloxy, hexadecyloxy, octadecyloxy or icosyloxy, in particular methoxy, ethoxy, propoxy, isopropoxy, n-butyloxy, sec-butyloxy, iso-butyloxy, tert-butyloxy, especially methoxy.

The term "phenylalkoxy" as used herein refers to phenyl, which is bound via an alkoxy group having preferably 1 to 4 carbon atoms, in particular a 1 or 2 carbon atoms, to the remainder of the molecule, examples including phenoxymethyl, 1-phenoxyethyl, 2-phenoxyethyl, and the like.

The term "alkylsulfanyl" as used herein refers to a saturated straight-chain or branched, alkyl radical having 1 to 4, to 6, to 8, to 12, to 16 or to 20 carbon atoms as defined above which is attached via a sulfur atom to the remainder of the molecule. Examples are methylsulfanyl, ethylsulfanyl, propylsulfanyl, isopropylsulfanyl, n-butylsulfanyl, sec-butylsulfanyl, isobutylsulfanyl and tert-butylsulfanyl.

The term "$C_2$-$C_8$-alkanoyl" ($C_1$-$C_7$alkyl-C(=O)—) as used herein refers to a saturated straight-chain or branched alkyl radical having 1 to 7 carbon atoms attached through the carbon atom of the carbonyl group at any position in the alkyl group, for example acetyl, propanoyl, 2-methyl-propanoyl, butanoyl, pentanoyl, hexanoyl.

The term "$C_m$-$C_n$-alkoxycarbonyl" ($C_m$-$C_n$-alkyl-O—C(O)—) as used herein refers to a saturated straight-chain or branched alkoxy radical having m to n carbon atoms as defined above attached through the carbon atom of the carbonyl group to the remainder of the molecule. Examples are methoxycarbonyl, ethoxycarbonyl, propoxycarbonyl, butoxy-carbonyl, isobutoxycarbonyl or pentoxycarbonyl.

The term "alkenyl" as used herein refers to mono- or polyunsaturated, straight-chain or branched hydrocarbon radicals having usually 2 to 20, preferably 2 to 16, more preferably 2 to 10 carbon atoms, having one or more, e.g. 1, 2, 3 or more than two double bonds, e.g., $C_2$-$C_6$-alkenyl having one double bond such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, or alkadienyl having usually 4 to 10 carbon atoms and two double bonds in any position, for example 1,3-butadienyl, 1,3-pentadienyl, hexa-1,4-dien-1-yl, hexa-1,4-dien-3-yl, hexa-1,4-dien-6-yl, hepta-1,4-dien-7-yl, hepta-1,5-dien-1-yl and the like.

Alkenyl radicals interrupted by non-adjacent groups selected from O, S, C(O) and N($R_N$) may be interrupted by one or more e.g. 1, 2, 3, 4, 5, 6, 7 or 8, of the above-mentioned groups, i.e, the termini of the alkenyl group are formed by carbon atoms. $R_N$ is as defined above. If a plurality of those interrupting heteroatoms or heteroatomic groups selected from O, S and $NR^N$ occurs, they are usually identical.

Substituted alkenyl groups may, depending on the length of the alkenyl chain, have one or more (e.g. 1, 2, 3, 4, 5 or more than 5) identical or different substituents. In the case of halogen substituted alkenyl, the alkenyl group can be partially of fully halogenated and/or may carry further substituents.

The term "haloalkenyl" as used herein, which is also expressed as alkenyl which may be substituted by halogen", refers to unsaturated straight-chain or branched hydrocarbon radicals having one or more double bonds (as mentioned above), where some or all of the hydrogen atoms in these groups are replaced by halogen atoms as mentioned above, in particular fluorine, chlorine and bromine. Examples for haloalkenyl are $C_2$-$C_{20}$-fluoroalkenyl, $C_2$-$C_{20}$ chloroalkenyl and $C_2$-$C_{20}$-bromoalkenyl.

The term "$C_3$-$C_6$-alkenoxy" as used herein refers to a mono- or diunsaturated straight-chain or branched alkenyl radical having 3 to 6 carbon atoms as defined above linked via an oxygen atom to the remainder of the molecule. Examples are vinyloxy, 1-propenyloxy, 2-propenyloxy, 1-methylethenyloxy, 1-butenyloxy, 2-butenyloxy, 3-butenyloxy, 1-methyl-1-propenyloxy, 2-methyl-1-propenyloxy, 1-methyl-2-propenyloxy, 2-methyl-2-propenyloxy, 1-pentenyloxy, 2-pentenyloxy, 3-pentenyloxy, 4-pentenyloxy, 1-methyl-1-butenyloxy, 2-methyl-1-butenyloxy, 3-methyl-1-butenyloxy, 1-methyl-2-butenyloxy, 2-methyl-2-butenyloxy, 3-methyl-2-butenyloxy, 1-methyl-3-butenyloxy, 2-methyl-3-butenyloxy, 3-methyl-3-butenyl, 1,1-dimethyl-2-propenyloxy, 1,2-dimethyl-1-propenyloxy, 1,2-dimethyl-2-propenyloxy, 1-ethyl-1-propenyloxy, 1-ethyl-2-propenyloxy, 1-hexenyloxy, 2-hexenyloxy, 3-hexenyloxy, 4-hexenyloxy and 5-hexenyloxy.

The term "$C_3$-$C_6$-alkenoyl ($C_2$-$C_6$-alkenyl-C(O)—)" as used herein refers to a mono- or diunsaturated straight-chain or branched alkenyl radical having 2 to 5 carbon atoms as defined above linked attached through the carbon atom of the carbonyl group at any position in the alkenyl group, for example propenoyl, 2-methyl-propenoyl, butenoyl, pentenoyl, 1,3-pentadienoyl, 5-hexenoyl.

The term "$C_2$-$C_{20}$-alkynyl" as used herein refers to unsaturated straight-chain or branched hydrocarbon radicals having 2 to 20, preferably 2 to 10 carbon atoms and one or two triple bonds in any position, e.g. ethynyl, propargyl (2-propyn-1-yl), 1-propyn-1-yl, 1-methylprop-2-yn-1-yl), 2-butyn-1-yl, 3-butyn-1-yl, 1-pentyn-1-yl, 3-pentyn-1-yl, 4-pentyn-1-yl, 1-methylbut-2-yn-1-yl, 1-ethylprop-2-yn-1-yl and the like. Alkynyl radicals interrupted by non-adjacent groups selected from O, S, C(O) and $N(R_N)$ may be interrupted by one or more, e.g. 1, 2, 3, 4, 5, 6, 7, 8 or more than 8 of these groups, i.e, the termini of the alkynyl group are formed by carbon atoms. $R_N$ is as defined above. If a plurality of those interrupting heteroatoms or heteroatomic groups occurs in the radical alkynyl, they are usually identical.

Substituted alkynyl groups may, depending on the length of the alkynyl chain, have one or more (e.g. 1, 2, 3, 4, 5 or more than 5) identical or different substituents. In the case of halogen substituted alkynyl, the alkynyl group can be partially of fully halogenated and/or may carry further substituents.

The term "haloalkynyl" as used herein, which is also expressed as "alkynyl which may be substituted by halogen", refers to unsaturated straight-chain or branched hydrocarbon radicals having one or more triple bonds (as mentioned above), where some or all of the hydrogen atoms in these groups are replaced by halogen atoms as mentioned above, in particular fluorine, chlorine and bromine. Examples for haloalkynyl are $C_2$-$C_{20}$-fluoroalkynyl, $C_2$-$C_{20}$ chloroalkynyl and $C_1$-$C_{20}$-bromoalkynyl.

The term "alkynyloxy" as used herein refers to a mono- or diunsaturated straight-chain or branched alkynyl radical having 3 to 6 carbon atoms as defined above which is attached via an oxygen atom to the remainder of the molecule, for example 2-propynyloxy, 2-butynyloxy, 3-butynyloxy, 1-methyl-2-propynyloxy, 2-pentynyloxy, 3-pentynyloxy, 4-pentynyloxy, 1-methyl-2-butynyloxy, 1-methyl-3-butynyloxy, 2-methyl-3-butynyloxy, 1-ethyl-2-propynyloxy, 2-hexynyloxy, 3-hexynyloxy, 4-hexynyloxy, 5-hexynyloxy, 1-methyl-2-pentynyloxy and 1-methyl-3-pentynyloxy.

The term "cycloalkyl" as used herein refers to a mono- or polycyclic, e.g. bi- or tricyclic aliphatic radical having usually from 3 to 30, preferably 3 to 20, more preferably 3 to 16, or 3 to 12 carbon atoms or in particular 3 to 8 carbon atoms. Examples of monocyclic rings are cyclopropyl, cyclobutyl, cyclopentyl, cyclohexyl, cycloheptyl or cyclooctyl, especially cyclopentyl and cyclohexyl. Examples of polycyclic rings are perhydroanthracyl, perhydronaphthyl, perhydrofluorenyl, perhydrochrysenyl, perhydropicenyl, adamantyl, bicyclo[1.1.1]pentyl, bicyclo[2.2.1]heptyl, bicyclo[4.2.2]decyl, bicyclo[2.2.2]octyl, bicyclo[3.3.0]octyl bicyclo[3.3.2]decyl, bicyclo[4.4.0]decyl, bicyclo[4.3.2]undecyl, bicy-clo[4.3.3]dodecyl, bicyclo[3.3.3]undecyl, bicyclo[4.3.1]decyl, bicyclo[4.2.1]nonyl, bicy-clo[3.3.1]nonyl, bicyclo[3.2.1]octyl and the like. Cycloalkyl may be interrupted by one or more CO groups, usually one or two groups. If cycloalkyl is interrupted by one or more CO groups, one or more methylene groups are replaced by CO. An example for cycloalkyl interrupted by 1 CO group is 3-oxobicyclo[2.2.1]heptyl. When cycloalkyl is substituted by one or more identical or different radicals, it is for example mono-, di-, tri-, tetra- or pentasubstituted, e.g. by $C_1$-$C_4$-alkyl. When cycloalkyl is substituted by one or more substituents, it is, for example, mono-, di-, tri-, tetra- or pentasubstituted or more than pentasubstituted.

The term "heterocyclyl" (also referred to as heterocycloalkyl), namely $C_2$-$C_9$heterocyclyl as used herein includes in general 3-, 4-, 5-, 6-, 7- or 8-membered, in particular 5-, 6-, 7- or 8-membered mono-cyclic heterocyclic non-aromatic radicals and 8 to 10 membered bicyclic heterocyclic non-aromatic radicals, the mono- and bicyclic non-aromatic radicals may be saturated or unsaturated. The mono- and bicyclic heterocyclic non-aromatic radicals usually comprise 1, 2, 3 or 4 heteroatoms, in particular 1 or 2 heteroatoms selected from N, O and S as ring members, where S-atoms as ring members may be present as S, SO or $SO_2$. If heterocycloalkyl is interrupted by one or more, e.g. 1 or 2, CO groups, one or more methylene groups are replaced by CO. Examples of saturated or unsaturated 3-, 4-, 5-, 6-, 7- or 8-membered heterocyclic radicals comprise saturated or unsaturated, non-aromatic heterocyclic rings, such as oxiranyl, oxetanyl, thietanyl, thietanyl-S-oxid (S-oxothietanyl), thietanyl-S-dioxid (S-dioxothiethanyl), pyrrolidinyl, pyrazolinyl, imida-zolinyl, pyrrolinyl, pyrazolinyl, imidazolinyl, tetrahydrofuranyl, dihydrofuranyl, 1,3-dioxolanyl, dioxolenyl, thiolanyl, S-oxothiolanyl, S-dioxothiolanyl, dihydrothienyl, S-oxodihydrothienyl, S-dioxodihydrothienyl, oxazolidinyl, isoxazolidinyl, oxazolinyl, isoxa-zolinyl, thiazolinyl, isothiazolinyl, thiazolidinyl, isothiazolidinyl, oxathiolanyl, piperidinyl, piperazinyl, pyranyl, dihydropyranyl, tetrahydropyranyl, 1,3- and 1,4-dioxanyl, thiopyranyl, S-oxothiopyranyl, S-dioxothiopyranyl, dihydrothiopyranyl, S-oxodihydrothiopyranyl, S-dioxodihydrothiopyranyl, tetrahydrothiopyranyl, S-oxotetrahydrothiopyranyl, S-dioxotetrahydrothiopyranyl, morpholinyl, thiomorpholinyl, S-oxothiomorpholinyl, S-dioxothiomorpholinyl, thiazinyl and the like. Examples for heterocyclic ring also comprising 1 or 2 carbonyl groups as ring members comprise pyrrolidin-2-onyl, pyrrolidin-2,5-dionyl, imidazolidin-2-onyl, oxazolidin-2-onyl, thiazolidin-2-onyl and the like.

If $C_2$-$C_9$heterocyclyl is substituted by one or more substituents, it is, for example, mono-, di-, tri-, tetra- or pentasubstituted or more than pentasubstituted.

The term "$C_6$-$C_{20}$aryl" as used herein refers to a monovalent aromatic group which is monocyclic, such as phenyl, or condensed polycyclic, for example naphthyl, phenanthryl or anthracenyl. Preferred examples of aryl are phenyl and naphthyl.

The term "$C_6$-$C_{10}$aryl" as used herein refers to phenyl and naphthyl.

The term "heteroaryl" (also referred to as "hetaryl") includes in general 5- or 6-membered unsaturated monocyclic heterocyclic radicals and 8 to 10 membered unsaturated bicyclic heterocyclic radicals which are aromatic, i.e. they comply with Hückel's rule (4n+2 rule). Hetaryl usually comprise besides carbon atom(s) as ring member(s) 1, 2, 3 or 4 heteroatoms selected from N, O and S as ring members. Examples of 5- or 6-membered heteroaromatic radicals include: 2-furyl, 3-furyl, 2-thienyl, 3-thienyl, 1-pyrrolyl, 2-pyrrolyl, 3-pyrrolyl, 1-pyrazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 3-isoxazolyl, 4-isoxazolyl or 5-isoxazolyl, 3-isothiazolyl, 4-isothiazolyl or 5-isothiazolyl, 1-imidazolyl, 2-imidazolyl, 4-imidazolyl, 2- or 5-[1,3,4]oxadiazolyl, 4- or 5-(1,2,3-oxadiazol)yl, 3- or 5-(1,2,4-oxadiazol)yl, 2- or 5-(1,3,4-thiadiazol)yl, 2- or 5-(1,3,4-thiadiazol)yl, 4- or 5-(1,2,3-thiadiazol)yl, 3- or 5-(1,2,4-thiadiazol)yl, 1H-, 2H- or 3H-1,2,3-triazol-4-yl, 1,3,4-triazol-2-yl, 2H-triazol-3-yl, 1H-, 2H-, or 4H-1,2,4-triazolyl, 1H- or 2H-tetrazolyl 2-pyridinyl, 3-pyridinyl, 4-pyridinyl, 3-pyridazinyl, 4-pyridazinyl, 2-pyrimidinyl, 4-pyrimidinyl, 5-pyrimidinyl and 2-pyrazinyl.

The term "heteroaryl" also includes bicyclic 8- to 10-membered heteroaromatic radicals comprising as ring members 1, 2 or 3 heteroatoms selected from N, O and S, wherein a 5- or 6-membered heteroaromatic ring is fused to a phenyl ring or to a 5- or 6-membered heteroaromatic radical. Examples of a 5- or 6-membered heteroaromatic ring fused to a phenyl ring or to a 5- or 6-membered heteroaromatic radical include benzofuranyl, benzothienyl, indolyl, indazolyl, benzimidazolyl, benzoxathiazolyl, benzoxadiazolyl, benzothiadiazolyl, benzoxazinyl, chinolinyl, isochinolinyl, purinyl, 1,8-naphthyridyl, pteridyl, pyrido[3,2-d]pyrimidyl or pyridoimidazolyl and the like. These fused hetaryl radicals may be bonded to the remainder of the molecule via any ring atom of 5- or 6-membered heteroaromatic ring or via a carbon atom of the fused phenyl moiety.

When heteroaryl is substituted by one or more identical or different radicals, it is for example mono-, di-, tri-, tetra- or pentasubstituted.

The term "$C_1$-$C_{20}$alkylene" as used herein in each case denotes an alkyl radical having 1 to 20 carbon atoms as defined above, wherein one hydrogen atom at any position of the alkyl radical is replaced by one further binding site, thus forming a bivalent moiety for example —$CH_2$—, —$CH_2CH_2$—, —$CH(CH_3)$—, —$CH_2CH_2CH_2$—, —$CH(CH_3)CH_2$—, —$CH_2CH_2CH_2CH_2$—, —$CH_2CH(CH_3)$ $CH_2$—, —$CH(CH_3)CH(CH_3)$—, —$CH_2CH_2CH_2CH_2$ $CH_2$—, —$CH_2(CH_2)_2CH(CH_3)$—, —$CH_2C(CH_3)_2CH_2$—, and the like.

The $C_1$-$C_{20}$-alkylene may be interrupted by one or more, identical or different non-adjacent groups denotes an alkylene chain having 1 to 20 carbon atoms as defined above where at least one internal methylene group of the alkylene chain is replaced by the interrupting group. The alkylene can be interrupted e.g. once, twice, three times, four times or more than four times.

If alkylene is substituted by one or more substituents, it is, for example, mono-, di-, tri-, tetra- or pentasubstituted or more than pentasubstituted.

The term "$C_2$-$C_{20}$-alkenylene" (or $C_2$-$C_{20}$-alkenediyl) as used herein in each case denotes a straight-chain or branched $C_2$-$C_{20}$-alkenyl radical as defined above, wherein one hydrogen atom at any position of the alkenyl radical is replaced by one further binding site, thus forming a bivalent moiety, for example —CH=CH—, —CH=CHCH$_2$—, —CH=C(H$_3$)CH$_2$—CH$_2$CH=CHCH$_2$—, —CH=CH—CH=CH—, —CH$_2$CH=CHCH$_2$CH$_2$— and the like.

"$C_2$-$C_{20}$-alkenylene may be interrupted by one or more identical or different non-adjacent groups" denotes an alkenylene chain having 2 to 20 carbon atoms as defined above where at least one internal methylene group of the alkenylene chain is replaced by a group $R_{Mi}$. The alkenylene can be interrupted e.g. once, twice, three times, four times or more than four times.

If alkenylene is substituted by one or more substituents, it is, for example, mono-, di-, tri-, tetra- or pentasubstituted or more than pentasubstituted.

The term "alkynylene" (or alkynediyl) as used herein in each case denotes a straight-chain or branched alkynyl radical as defined above, wherein one hydrogen atom at any position of the alkynyl radical is replaced by one further binding site, thus forming a bivalent moiety. Accordingly, $C_2$-$C_{20}$-alkynylene is a divalent straight-chain or branched aliphatic chain having 2 to 20 carbon atoms.

"$C_2$-$C_{20}$-alkynylene may be interrupted by one or more identical or different non-adjacent groups" denotes an alkynylene chain having 2 to 20 carbon atoms as defined above where at least one internal methylene group of the alkynylene chain is replaced by a group The alkynylene can be interrupted e.g. once, twice, three times, four times or more than four times.

The term "$C_3$-$C_{20}$-cycloalkylene" (also referred to as cycloalkanediyl) refers to cycloalkyl radical having 3 to 20 carbon atoms as defined above, wherein one hydrogen atom at any position of cycloalkyl is replaced by one further binding site, thus forming a divalent radical. In case of polycyclic cycloalkanediyl, the bonding sites are either situated in the same ring or in different rings. Examples for monocyclic rings are cyclopropylene, cyclobutylene, cyclopentylene, cyclohexylene or cycloheptylen, especially cyclohexylene. Examples of polycyclic rings are perhydroanthracylene, perhydronaphthylene, perhydrofluorenylene, perhydrochrysenylene, perhydropicenylene, adamantylene, bicyclo[1.1.1]pentylen, bicycle[2.2.1]heptylene, bicyclo[4.2.2]decylene, bicyclo[2.2.2]-octylene, bicyclo[3.3.2]decylene, bicyclo[4.3.2]undecylene, bicy-clo[4.3.3] dodecylene, bicyclo[3.3.3]undecylene, bicyclo[4.3.1]decylene, bicy-clo[4.2.1]nonylene, bicycle-[3.3.1]nonylene, bicyclo[3.2.1]octylene and the like. If cycloalkanediyl is substituted by one or more substituents, it is, for example, mono-, di-, tri-, tetra- or pentasubstituted or more than pentasubstituted, e.g. by $C_1$-$C_4$-alkyl.

The term "$C_6$-$C_{20}$-arylene" (also referred to as arenediyl) as used herein refers to an aryl group as defined above, wherein one hydrogen atom at any position of the aryl group is replaced by one further binding site, thus forming a bivalent radical. In case of polycyclic arylene, the bonding sites are either situated in the same ring or in different rings. Examples of arylene are phenylen, naphthylene, e.g. 1,5-naphthalenediyl, and 1,8-naphthalenediyl, anthracenediyl or phenanthrenediyl. If arylene is substituted by one or more substituents, it is, for example, mono-, di-, tri-, tetra- or pentasubstituted or more than pentasubstituted.

The term "phenylene" refers to 1,2-phenylene (o-phenylene or 1,2-benzenediyl), 1,3-phenylene (m-phenylene, 1,3-benzenediyl) and 1,4-phenylene (p-phenylene or 1,4-benzenediyl). The term "naphthylene" refers to 1,2-naphthylene, 1,3-naphthylene, 1,4-naphthylene, 1,5-naphthylene, 1,8-naphthylene, 2,3-naphthylene and 2,7-naphthylene. The term "xylylene" refers to 1,2-xylylene (1,2-methylenephenylenemethylene, 1,2-$CH_2$—$C_6H_4$—$CH_2$), 1,3-xylylene (1,3-methylenephenylenemethylene, 1,3-$CH_2$—$C_6H_4$—$CH_2$) and 1,4-xylylene (1,4-methylenephenylenemethylene, 1,4-$CH_2$—$C_6H_4$—$CH_2$).

The term "heteroarylene" (also referred to as heteroarenediyl) refers to a heteroaryl radical as defined above, where one hydrogen atom at any position of the heteroaryl group is replaced by a further binding site, thus forming a divalent radical. In case of polycyclic heteroarenediyl, the bonding sites are either situated in the same ring or in different rings. Heteroarenediyl can be C-attached or N-attached where such is possible. For example, a pyrrolediyl, imidiazolediyl or pyrazolediyl can be N-attached or C—attached. Examples for heteroarenediyl are pyridinediyl, pyrimidinediyl, pyridazinediyl, 1,2,3-triazinediyl, 1,2,4-triazinediyl, 1,2,3,4-tetrazinediyl, furandiyl, thiophenediyl, pyrrolediyl, thiazolediyl, thiadiazolediyl, pyrazolediyl, imidazolediyl, triazolediyl, oxazolediyl, isoxazolediyl, isothiazolediyl, oxadiazolediyl and the like. If heteroarenediyl is substituted by one or more substituents, it is, for example, mono-, di-, tri-, tetra- or pen-tasubstituted or more than pentasubstituted.

The term "arylalkyl" (also referred to as aryl-alkylene) as used herein refers to an aryl radical as defined below which is linked via an alkylene group, in particular via a methylene, 1,1-ethylene or 1,2-ethylene group, e.g. benzyl, 1-phenyl-ethyl and 2-phenylethyl and the like.

The terms "and/or" or "or/and" in the present context are meant to express that not only one of the defined alternatives (substituents) may be present, but also several of the defined alternatives (substituents) together, namely mixtures of different alternatives (substituents).

The term "at least" is meant to define one or more than one, for example one or two or three, preferably one or two.

The term "optionally substituted" means, that the radical to which it refers is either unsubstituted or substituted.

The term "one or more identical or different radicals" is meant to define one, two, three, four, five, six, seven, eight or more than eight identical or different radicals.

Throughout this specification and the claims which follow, unless the context requires otherwise, the word "comprise", or variations such as "comprises" or "comprising", will be understood to imply the inclusion of a stated integer or step or group of integers or steps but not the exclusion of any other integer or step or group of integers or steps.

The term "(meth)acrylate" in the context of the present application is meant to refer to the acrylate as well as to the corresponding methacrylate.

The preferences indicated for the compounds of the formula I, Ia or Ib according to the present invention in the context of this invention are intended to refer to all categories of the claims, that is to the composition, use and method claims as well.

The remarks made below as to preferred embodiments of the variables (substituents) of the compounds of formula I, Ia or Ib are valid on their own as well as in combination with each other.

Preferred are compounds of the formula I, wherein $R_4$ is the group of the formula (A)

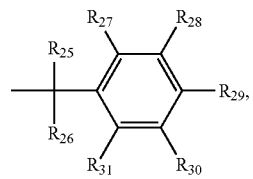

wherein $R_{25}$, $R_{26}$, $R_{27}$, $R_{28}$, $R_{29}$, $R_{30}$ and $R_{31}$ are as defined above.

Further interesting are compounds of the formula I wherein $R_{25}$ is hydrogen, $C_1$-$C_{12}$alkyl or phenyl;

$R_{26}$ is hydrogen, $C_1$-$C_{12}$alkyl or phenyl;

$R_{28}$ is hydrogen, fluorine, chlorine, $NO_2$, $OR_{20}$, $COR_{21}$, $COOR_{22}$, $CONR_{23}R_{24}$ or $C_1$-$C_{12}$alkyl;

$R_{29}$ is hydrogen, fluorine, chlorine, $NO_2$, $OR_{20}$, $COR_{21}$, $COOR_{22}$, $CONR_{23}R_{24}$ or $C_1$-$C_{12}$alkyl;

$R_{30}$ is hydrogen, fluorine, chlorine, $NO_2$, $OR_{20}$, $COR_{21}$, $COOR_{22}$, $CONR_{23}R_{24}$ or $C_1$-$C_{12}$alkyl; and $R_{31}$ is hydrogen, fluorine, chlorine, $NO_2$, $OR_{20}$, $COR_{21}$, $COOR_{22}$, $CONR_{23}R_{24}$ or $C_1$-$C_{12}$alkyl; or $R_{27}$ and $R_{28}$, $R_{28}$ and $R_{29}$, $R_{29}$ and $R_{30}$ and/or $R_{30}$ and $R_{31}$ together with the carbon atoms to which they are attached may be together a group selected from —$CH_2CH_2CH_2$—, —$CH_2CH_2CH_2CH_2$— and —CH=CH—CH=CH—, thus forming, together with the carbon atoms to which they are bound, a 5- or 6-membered ring, in particular a benzene ring; where $R_{20}$, $R_{21}$, $R_{23}$ and $R_{24}$ are as defined above and preferably have one of the meanings being preferred.

In particular $R_4$ is benzyl, i.e. $R_{27}$, $R_{28}$, $R_{29}$, $R_{30}$, $R_{31}$ are each hydrogen. Likewise, in particular, $R_{25}$ and $R_{26}$ are both hydrogen, and one or two of the radicals $R_{27}$, $R_{28}$, $R_{29}$, $R_{30}$ and $R_{31}$ are selected from nitro, fluorine, chlorine, $C_1$-$C_4$alkyl, $OR_{20}$, $COOR_{22}$, and $CONR_{23}R_{24}$ and the other radicals $R_{27}$, $R_{28}$, $R_{29}$, $R_{30}$ and $R_{31}$ are hydrogen. Likewise, in particular $R_{25}$, $R_{26}$, $R_{27}$, $R_{28}$ and $R_{29}$ are each hydrogen and $R_{30}$ and $R_{31}$ are together —CH=CH—CH=CH—, thus forming, together with the carbon atoms, to which they are bound a benzene ring.

In the compounds of the formula I, wherein $R_4$ is the group of the formula A, more preference is given to those compounds, wherein $R_4$ is naphthylmethyl; benzyl or benzyl which is substituted by one or two radicals selected from nitro, fluorine, chlorine, $C_1$-$C_4$-alkyl, $C_1$-$C_4$-alkoxy, $C_1$-$C_4$-alkoxycarbonyl, C(O)O—($C_1$-$C_4$-alky-OH) and C(O)N($C_1$-$C_4$-alkyl)$_2$.

Preference is likewise given to compounds of the formula I, in which $R_4$ is the group of the formula B

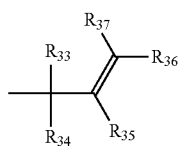

and $R_{33}$, $Ra_{34}$, $R_{35}$, $R_{36}$ and $R_{37}$ are as defined above.

$R_4$ for example is the group of the formula B, where
$R_{33}$ is hydrogen, $C_1$-$C_{12}$alkyl or phenyl;
$R_{34}$ is hydrogen, $C_1$-$C_{12}$alkyl or phenyl;
$R_{35}$ is hydrogen, $C_1$-$C_{12}$alkyl, phenyl or $C_2$-$C_{12}$alkenyl;
$R_{36}$ is hydrogen, $C_1$-$C_{12}$alkyl, phenyl or $C_2$-$C_{12}$alkenyl; and
$Ra_{37}$ is hydrogen, fluorine, chlorine, $C_1$-$C_{12}$alkyl, phenyl or $C_2$-$C_{12}$alkenyl.

In particular, $R_{33}$ and $R_{34}$ are both hydrogen, and one or two of the radicals $R_{35}$, $R_{36}$ and $R_{37}$ are $C_1$-$C_4$alkyl or phenyl and the other radicals $R_{35}$, $R_{36}$ and $R_{37}$ are hydrogen In the compounds of the formula I, wherein $R_4$ is the group of the formula B, more preference is given to those compounds, wherein $R_4$ is prop-2-en-1-yl, 3-phenyl-prop-2-en-1-yl, 2-($C_1$-$C_4$-alkyl)-prop-2-en-1-yl, or 3-($C_1$-$C_4$-alkyl)-prop-2-en-1-yl.

Preference is likewise given to compounds of the formula I, in which $R_4$ is $C_3$-$C_{12}$cycloalkyl, in particular $C_3$-$C_8$cycloalkyl. Examples are cyclobutyl, cyclopentyl, cyclohexyl, cycloheptyl and cyclooctyl, in particular cyclopentyl or cyclohexyl.

Preference is likewise given to compounds of the formula I, in which $R_4$ is $C_3$-$C_{12}$cycloalkyl, which is substituted by one or more, e.g. 1, 2 or 3, identical or different radicals selected from F, Cl, Br, I, $C_1$-$C_{12}$-alkyl, $OR_{20}$, $COR_{21}$, $COOR_{22}$ and $CONR_{23}R_{24}$, where $R_{20}$, $R_{21}$, $R_{22}$, $R_{23}$ and $R_{24}$ are as defined above and preferably have one of the meanings being preferred. More preferably, $R_4$ is $C_3$-$C_8$cycloalkyl which is substituted by one, two or three of identical or different radicals selected from F, Cl, Br, I, $C_1$-$C_8$alkyl, $OR_{20}$, $COOR_{22}$ and $CONR_{23}R_{24}$. In particular $R_4$ is $C_3$-$C_8$cycloalkyl which is substituted by one, two or three of identical or different radicals selected from F, Cl, Br, I, $C_1$-$C_8$alkyl, $C_1$-$C_4$alkoxy, hydroxy, $C_1$-$C_4$fluoroalkylcarbonyloxy, $C_1$-$C_4$ chloroalkylcarbonyloxy, C(O)O—($C_1$-$C_4$-alkyl-OH) and C(O)N($C_1$-$C_4$-alkyl)$_2$.

Preference is likewise given to compounds of the formula I, in which $R_4$ is $C_1$-$C_{12}$alkyl. In particular $R_4$ is $C_1$-$C_8$alkyl such as methyl, ethyl, n-propyl, isopropyl, n-butyl, pentyl or hexyl, in particular methyl.

Preference is likewise given to compounds of the formula I, in which $R_4$ is $C_1$-$C_{12}$alkyl, which is substituted by one or more, e.g. 1 or 2, identical or different radicals selected from F, Cl, Br, I, $OR_{20}$, $COR_{21}$, $COOR_{22}$, $CONR_{23}R_{24}$, $C_3$-$C_{12}$cycloalkyl and 5- to 6-membered heterocyclyl, where $R_{20}$, $R_{21}$, $R_{23}$ and $R_{24}$ are as defined above and preferably have one of the meanings being preferred. Examples are $C_1$-$C_{12}$fluoroalkyl, $C_1$-$C_{12}$chloroalkyl, $C_1$-$C_4$alkoxy-$C_1$-$C_{12}$alkyl, phenoxy-$C_1$-$C_{12}$alkyl, phenylcarbonyl-$C_1$-$C_{12}$alkyl, $C_1$-$C_4$-alkoxycarbonyl-$C_1$-$C_{12}$alkyl, $C_1$-$C_4$alkoxy-$C_1$-$C_4$alkoxycarbonyl-$C_1$-$C_{12}$alkyl, $C_3$-$C_{12}$cycloalkyl-$C_1$-$C_{12}$alkyl and 5- or 6-membered heterocyclyl-$C_1$-$C_{12}$alkyl, where the heterocyclyl moiety is a 5- to 6-membered saturated heterocyclic ring comprising besides carbon atoms one or two heteroatoms selected from O, S or N.

Examples for $R_4$ are phenoxy-$C_1$-$C_6$alkyl, especially phenoxymethyl or 2-phenoxyethyl; $C_1$-$C_4$alkoxycarbonyl-$C_1$-$C_6$alkyl, especially methoxycarbonylmethyl, ethoxycarbonylmethyl, 2-methoxycarbonylethyl, 2-ethoxycarbonylethyl, 3-methoxycarbonylpropyl, 3-ethoxycarbonylpropyl, 4-methoxycarbonylbutyl or 4-ethoxycarbonylbutyl; phenylcarbonyl-$C_1$-$C_6$alkyl, especially benzoylmethyl; $C_1$-$C_4$alkoxy-$C_1$-$C_6$alkyl, especially 2-methoxy-ethyl or 3-methoxypropyl; $C_1$-$C_4$alkoxy-$C_1$-$C_4$-alkoxycarbonyl-$C_1$-$C_6$alkyl, especially 3-methoxy-butoxycarbonyl, 2-methoxypropoxycarbonyl, 3-ethoxybutoxycarbonyl or 2-ethoxypropoxycarbonyl; $C_3$-$C_{12}$cycloalkyl-$C_1$-$C_6$alkyl, especially cyclohexylmethyl, 2-cyclohexylethyl, cyclopentylmethyl or 2-cyclopentylethyl; heterocycloalky-$C_1$-$C_{62}$alkyl is preferably tetrahydrofuan-2-yl-methyl, tetrahydrofuran-3-yl-methyl, tetrahydrothiophen-2-ylmethyl, tetrahydrothiophen-3-ylmethy, 2-(tetrahydrofuran-2-yl)-ethyl, 2-(tetrahydrofuran-3-yl)-ethyl, 2-(tetrahydrothiophen-2-yl)-ethyl or 2-(tetrahydrothiophen-3-yl)-ethyl.

Even more preferably, in this embodiment $R_4$ is $C_1$-$C_6$alkyl, $C_1$-$C_4$alkoxy-(CO)—$C_1$-$C_4$alkyl, tetrahydrofuranyl-$C_1$-$C_4$alkyl, tetrahydrothiophen-$C_1$-$C_4$alkyl or phenoxy-$C_1$-$C_4$alkyl.

Examples of radicals $R_4$ are 1-naphthylmethyl, benzyl, 4-methylbenzyl, 4-ethoxycarbonylbenzyl, 4-chlorobenzyl, 2,4-dichlorobenzyl, 3,4-dichlorobenzyl, 4-nitrobenzyl, 4-diisopropylcarbamoylbenzyl, 4-(2-hydroxyethoxycarbonyl)benzyl, 4-(2-methoxy-1-methylethoxycarbonyl)benzyl, 4-ethoxycarbonylbenzyl, 3-methoxybenzyl, 3-methylbenzyl, 2-methylbenzyl, 2-chlorobenzyl, 2-methylprop-2-enyl, 3-methylbut-2-enyl, allyl, (E)-3-phenylprop-2-enyl, (Z)-3-phenylprop-2-enyl, 3-phenylprop-2-enyl, cyclohexyl, methyl, ethyl, n-butyl, n-octyl, 2-methoxycarbonylethyl, 2-phenoxyethyl, 3-methoxybutoxycarbonylmethyl, tetrahydrofuran-2-ylmethyl, tetrahydrothiophen-2-ylmethyl and ethoxycarbonylmethyl.

Preference is also given to those compounds of the formula I, where $R_5$ and $R_6$ are independently of one another selected from $C_1$-$C_{12}$alkyl; $C_1$-$C_{12}$alkyl, which is substituted by one or more identical or different radicals $R_{2a}$, where $R_{2a}$ is as defined above; $C_3$-$C_{12}$cycloalkyl; $C_3$-$C_{12}$cycloalkyl, which is substituted by one or more identical or different radicals $R_{2b}$, where $R_{2b}$ is as defined above; phenyl; and phenyl, which is substituted by one, two, three, four or five radicals $R_{2c}$, where $R_{2c}$ is as defined above. Preferred among these are compounds of the formula I, where $R_5$ and/or $R_6$ is $C_1$-$C_{12}$alkyl which is unsubstituted or is partly or completely halogenated and/or has 1, 2 or 3 identical or different radicals $R_{2a}$ selected from $OR_{20}$, $COR_{21}$, $COOR_{22}$, $CONR_{23}R_{24}$, heterocycloalkyl, $C_3$-$C_8$cydoalkyl, phenyl and naphthyl, where the two last-mentioned radicals are unsubstituted or substituted by 1, 2, 3, 4, or 5 identical or different radicals selected from $C_1$-$C_{12}$alkyl, F, Cl, Br, I, $NO_2$, $OR_{20}$, $COOR_{22}$ and $CONR_{23}R_{24}$. $R_{20}$, $R_{22}$, $R_{23}$ and $R_{24}$ are as defined above and preferably have one of the meanings being preferred.

In a particular preferred embodiment $R_5$ and/or $R_6$ is $C_1$-$C_8$alkyl such as methyl, ethyl, n-propyl, isopropyl, n-butyl, sec-butyl, tert-butyl, n-pentyl, or hexyl or n-octyl, in particular methyl, ethyl, n-propyl, n-butyl or n-octyl.

Likewise, in a particular preferred embodiment $R_5$ and/or $R_6$ are $C_1$-$C_8$-fluoroalkyl, $C_1$-$C_8$chloroalkyl, $C_1$-$C_4$alkoxy-$C_1$-$C_6$alkyl, phenoxy-$C_1$-$C_6$alkyl, benzoyl-$C_1$-$C_6$alkyl, benzyloxycarbonyl-$C_1$-$C_6$alkyl or phenyl-$C_1$-$C_6$alkyl, where the alkyl moiety of the last-mentioned radical is substituted by benzoyl.

Examples for $R_5$ and/or $R_6$ are $C_1$-$C_4$alkoxy-$C_1$-$C_2$alkyl, especially are 2-methoxy-ethyl or 3-methoxypropyl; phenoxy-$C_1$-$C_4$alkyl, especialy phenoxymethyl, 2-phenoxyethyl or 3-phenoxypropyl; benzoyl-$C_1$-$C_4$-alkyl, especially 2-oxo-2-phenylethyl, 3-oxo-3-phenylpropyl or 4-oxo-4-phenylbutyl; benzyloxycarbonyl-$C_1$-$C_4$-alkyl, especially 2-benzyloxycarbonyl-ethyl or 2-methyl-2-benzyloxycarbonylethyl; phenyl-$C_1$-$C_4$alkyl, where the alkyl moiety of phenylalkyl is substituted by benzoyl, especially 2-oxo-1,2-diphenylethyl, 3-oxo-1,3-diphenylpropyl or 4-oxo-1,4-diphenylbutyl.

Likewise, in a particular preferred embodiment, $R_5$ and/or $R_6$ are $C_1$-$C_4$alkoxycarbonyl-$C_1$-$C_6$alkyl, $C_1$-$C_4$alkoxy-$C_1$-$C_4$alkoxycarbonyl-$C_1$-$C_6$alkyl, $C_3$-$C_8$cycloalkyl-$C_1$-$C_6$alkyl, naphthyl-$C_1$-$C_6$alkyl or heterocyclyl-$C_1$-$C_6$alkyl, wherein heterocyclyl is a 5- to 6-membered saturated heterocyclic ring comprising besides carbon atoms one or two heteroatoms selected from O and S.

Examples for $R_5$ and/or $R_6$ are $C_1$-$C_4$alkoxycarbonyl-$C_1$-$C_4$alkyl, especially methoxycarbonylmethyl, ethoxycarbonylmethyl, 2-methoxycarbonylethyl, 2-ethoxycarbonylethyl, 3-methoxycarbonylpropyl, 3-ethoxycarbonylpropyl, 4-methoxycarbonylbutyl or 4-ethoxycarbonylbutyl; $C_1$-$C_4$-alkoxy-$C_1$-$C_4$-alkoxycarbonyl-$C_1$-$C_4$-alkyl, especially 3-methoxybutoxycarbonylmethyl, 3-methoxybutoxycarbonylethyl, 3-ethoxybutoxycarbonylmethyl or 3-ethoxybutoxycarbonylethyl; $C_3$-$C_8$cycloalkyl-$C_1$-$C_4$ alkyl, especially cyclohexylmethyl, 2-cyclohexylethyl, cyclopentylmethyl or 2-cyclopentylethyl; naphthyl-$C_1$-$C_4$-alkyl, especially 1-naphthylmethyl, 2-napthylmethyl, 1-(naphthalene-1-yl)ethyl, 1-(naphthalene-2-yl)ethyl, 2-(naphthalene-1-yl)ethyl or 2-(naphthalene-2-yl)ethyl; heterocyclyl-$C_1$-$C_4$-alkyl are tetrahydrofuran-2-ylmethyl, tetra-hydrofuran-3-ylmethyl, 2-(tetrahydrofuran-2-yl)ethyl, 2-(tetrahydrofuran-3-yl)ethyl, 3-(tetrahydrofuran-2-yl)propyl, 3-(tetrahydrofuran-3-yl)propyl, tetrahydrothiophen-2-ylmethyl, tetrahydrothiophen-3-yl-methyl, 2-(tetrahydrothiophen-2-yl)ethyl, 2-(tetrahydrothiophen-3-yl)ethyl, 3-(tetrahydrothiophen-2-yl)propyl or 3-(tetrahydrothiophen-3-yl)propyl.

Likewise, in a preferred embodiment, $R_5$ and/or $R_6$ is phenyl-$C_1$-$C_6$alkyl, in which the phenyl moiety of phenylalkyl is unsubstituted or substituted by 1, 2, 3, 4 or 5 identical ordifferent radicals selected from F, Cl, Br, I, OH, $NO_2$, $C_1$-$C_{10}$alkyl, $C_1$-$C_4$alkoxy, heterocyclyl-$C_1$-$C_4$alkoxy, $C_1$-$C_4$fluoroalkanoyloxy, hydroxy-$C_1$-$C_4$alkoxycarbonyl, $C_1$-$C_4$alkoxycarbonyl, $C_1$-$C_4$-alkoxy-$C_1$-$C_4$-alkoxycarbonyl, benzyloxycarbonyl and $C(=O)N(C_1$-$C_8$-alkyl$)_2$. In particular $R_5$ and/or $R_6$ is phenyl-$C_1$-$C_2$alkyl, in which the phenyl moiety of phenylalkyl is unsubstituted or substituted by 1 or 2 identical or different radicals selected from fluorine, chlorine, $C_1$-$C_4$alkyl, $C_1$-$C_4$alkoxy, ($C_1$-$C_4$ alkoxy)carbonyl, C(O)O—($C_1$-$C_4$alkyl-OH), and C(O)N($C_1$-$C_8$alkyl$)_2$.

Examples for $R_5$ and/or $R_6$ are phenyl-$C_1$-$C_4$alkyl, where the phenyl moiety of phenylalkyl is substituted by 1 or 2 chlorines, especially 2-chlorobenzyl, 3-chlorobenzyl, 4-chlorobenzyl, 2,4-dichlorobenzyl, 3,4-dichlorbenzyl, 3,5-dichlorobenzyl, 2-(2-chlorophenyl)ethyl, 2-(3-chlorophenyl)ethyl, 2-(4-chlorophenyl)ethyl, 2-(2,4-dichlorophenyl)-ethyl, 2-(3,5-dichlorophenyl)ethyl or 2-(3,4-dichlorophenyl)ethyl; phenyl-$C_1$-$C_4$alkyl, where the phenyl moiety of phenylalkyl is substituted by hydroxy, especially 2-hydroxybenzyl, 3-hydroxybenzyl, 4-hydroxybenzyl, 2-(2-hydroxyphenyl)ethyl, 2-(3-hydroxyphenyl)ethyl or 2-(4-hydroxyphenyl); phenyl-$C_1$-$C_4$alkyl, where the phenyl moiety of phenylalkyl is substituted by 1 or 2 $C_1$-$C_{10}$alkyl groups, especially 2-, 3- or 4-methylbenzyl, 2-, 3-, 4-ethylbenzyl, 2-, 3- or 4-propylbenzyl, 2-, 3- or 4-butylbenzyl, 2,4-dimethylbenzyl or 3,5-dimethylbenzyl; phenyl-$C_1$-$C_4$alkyl, where the phenyl moiety of phenylalkyl is substituted by 1 or 2 $C_1$-$C_4$-alkoxy groups, especially 2-, 3- or 4-methoxybenzyl, 2-, 3-, 4-ethoxybenzyl, 2-, 3- or 4-propoxybenzyl, 2-, 3- or 4-butoxybenzyl, 2,4-dimethoxybenzyl or 3,5-dimethoxybenzyl; phenyl-$C_1$-$C_4$alkyl, where the phenyl moiety of phenylalkyl is substituted by $C_1$-$C_4$-alkoxycarbonyl, especially 2-ethoxycarbonylbenzyl, 3-ethoxycarbonylbenzyl, 4-ethoxycarbonylbenzyl, 2-(2-ethoxy-carbonylphenyl)ethyl, 2-(3-ethoxycarbonylphenyl)ethyl or 4-(3-ethoxycarbonylphenyl)-ethyl; phenyl-$C_1$-$C_4$-alkyl, where the phenyl moiety of phenylalkyl is substituted by hydroxy-$C_1$-$C_4$-alkoxycarbonyl, especially 4-(2-hydroxyethoxycarbonyl)benzyl, 2-(4-(2-hydroxyethoxycarbonylphenyl)ethyl; phenyl-$C_1$-$C_4$-alkyl, where the phenyl moiety of phenylalkyl is substituted by $C(=O)N(C_1$-$C_8$-alkyl$)_2$, especially 4-dimethylcarbamoylbenzyl, 4-diethylcarbamoylbenzyl, 4-diisopropylcarbamoylbenzyl, 2-(4-dimethylcarbamoylphenyl)ethyl, 2-(4-diethylcarbamoylphenyl)ethyl or 2-(4-diisopropylcarbamoylphenyl)ethyl.

Likewise preferred among these are compounds of the general formula Ia, where $R_5$ and/or $R_6$ are $C_3$-$C_{12}$-Cycloalkyl, which is unsubstituted or has 1, 2 or 3 identical or different radicals $R^{2b}$ selected from F, Cl, Br, I, $OR_{20}$, $COR_{21}$, $COOR_{22}$, $CONR_{23}R_{24}$, $C_2$-$C_9$heterocyclyl, $C_3$-$C_8$cycloalkyl, phenyl and naphthyl, where the two last-mentioned radicals may be substituted by 1, 2, 3, 4, or 5 different or identical radicals selected from F, Cl, Br, I, $NO_2$, $C_1$-$C_{12}$-alkyl, $OR_{20}$, $COOR_{22}$ and $CONR_{23}R_{24}$. $R_{20}$, $R_{22}$, $R_{23}$ and $R_{24}$ are as defined above and preferably have one of the meanings being preferred. In a particular preferred embodiment, $R_5$ and/or $R_6$ are $C_3$-$C_8$cycloalkyl such as cyclopropyl, cyclobutyl, cyclopentyl, cyclohexyl or cyclheptyl. Likewise, in a particular preferred embodiment, $R_5$ and/or $R_6$ are $C_3$-$C_8$cycloalkyl which is substituted by one, two or three of identical or different radicals selected from F, Cl, Br, I, $C_1$-$C_8$-alkyl, $OR_{20}$, $COOR_{22}$ and $CONR_{23}R_{24}$, where $R_{20}$, $R_{22}$, $R_{23}$ and $R_{24}$ are as defined above.

Likewise preferred among these are compounds of the general formula I where $R_5$ and/or $R_6$ are phenyl, which is unsubstituted or has 1, 2, 3, 4 or 5 identical or different radicals $R_{2c}$ selected from F, Cl, Br, I, $C_1$-$C_{10}$-alkyl, $SR_{19}$ and $OR_{20}$. $R_{19}$ and $R_{20}$ are as defined above and preferably have one of the meanings being preferred. More preferably, $R_5$ and/or $R_6$ are phenyl which is unsubstituted or substituted by 1, 2, 3, 4 or 5 identical or different radicals which are selected from the group consisting of F, Cl, Br, I, OH, $NO_2$, $C_1$-$C_{10}$alkyl, $C_1$-$C_4$alkoxy, $C_2$-$C_9$heterocyclyl-$C_1$-$C_4$alkoxy, $C_1$-$C_4$fluoroalkanoyloxy, hydroxy-$C_1$-$C_4$alkoxycarbonyl, $C_1$-$C_4$alkoxycarbonyl, $C_1$-$C_4$alkoxy-$C_1$-$C_4$alkoxycarbonyl, benzyloxycarbonyl and $C(=O)N(C_1$-$C_8$-alkyl$)_2$. In particular $R_5$ and/or $R_6$ are phenyl which is unsubstituted or substituted by 1 or 2 identical or different radicals selected from fluorine, chlorine, hydroxy, nitro, $C_1$-$C_{10}$alkyl, $C_1$-$C_4$alkoxy, $C_1$-$C_4$fluoralkylcarbonyloxy and (heterocyclyl)-$C_1$-$C_4$alkoxy, where the heterocyclyl moiety is a 5- to 6-membered saturated heterocyclic ring comprising besides carbon atoms one or two heteroatoms selected from O or S.

In this embodiment, examples for $R_5$ and/or $R_6$ are phenyl; phenyl substituted by one, two, three or four $C_1$-$C_{10}$ alkyl groups, especially 2-methylphenyl, 3-methylphenyl, 4-methylphenyl, 2-ethylphenyl, 3-ethylphenyl, 4-ethylphenyl, 2-, 3-, 4-n-propylphenyl, 2-, 3-, 4-isopropylphenyl, 2-, 3-, 4-butylphenyl, 2-(1,1,3,3-tetramethylbutyl)phenyl, 3-(1,1,3,3-tetramethylbutyl)phenyl, 4-(1,1,3,3-tetramethylbutyl)phenyl, 2,4-dimethylphenyl, 3,5-dimethylphenyl, 3,5-diisopropylphenyl; phenyl substituted by OH, especially 2-hydroxyphenyl, 3-hydroxyphenyl and 4-hydroxyphenyl; phenyl substituted by one, two, three or four groups selected from OH and $C_1$-$C_{10}$ alkyl, especially are 2-hydroxy-5-(1,1,3,3-tetramethylbutyl)phenyl, 3,5-diisopropyl-4-hydroxyphenyl, 5-tert-butyl-4-hydroxy-2-methylphenyl or 3,5-di-tert-butyl-4-hydroxyphenyl; phenyl substituted by $C_2$-$C_9$heterocyclyl-$C_1$-$C_4$-alkoxy, especially 2-(tetrahydrofuran-2-ylmethoxy)phenyl, 3-(tetrahydrofuran-2-ylmethoxy)phenyl, 4-(tetrahydrofuran-2-ylmethoxy)phenyl, 2-(tetrahydrofuran-3-ylmethoxy)phenyl, 3-(tetrahydrofuran-3-ylmethoxy)phenyl, 4-(tetrahydrofuran-3-ylmethoxy)phenyl, 2-(tetrahydrothiophen-2-ylmethoxy)phenyl, 3-(tetrahydrothiophen-2-ylmethoxy)phenyl, 4-(tetrahydrothiophen-2-ylmethoxy)phenyl, 2-(tetrahydrothiophen-3-ylmethoxy)phenyl, 3-(tetrahydrothiophen-3-ylmethoxy)phenyl or 4-(tetrahydrothiophen-3-ylmethoxy)phenyl; phenyl substituted by $C_1$-$C_4$fluoroalkanoyloxy, especially 2,2,2-trifluoroacetoxyphenyl or 3,3,3-trifluoropropionyloxyphenyl.

Examples for radicals $R_5$ and $R_6$ are benzyl, 4-methoxybenzyl, 4-methylbenzyl, 4-ethoxycarbonylbenzyl, 4-chlorobenzyl, 2,4-dichlorobenzyl, 3,4-dichlorobenzyl, 4-nitrobenzyl, 4-diisopropylcarbamoylbenzyl, 4-(2-hydroxyethoxycarbonyl)benzyl, 4-(2-methoxy-1-methylethoxycarbonyl)benzyl, 4-ethoxycarbonylbenzyl, 4-benzyloxycarbonylbenzyl, 3-methoxybenzyl, 3-methylbenzyl, 3-chlorobenzyl, 2-methylbenzyl, 2-chlorobenzyl, 1-naphthylmethyl, 2-naphthylmethyl, 2-methoxycarbonylethyl, 2-phenoxyethyl, 2-oxo-1,2-diphenylethyl, 2-oxo-2-phenylethyl, 2-benzyloxycarbonyl-ethyl, 2-benzyloxycarbonylpropyl, methyl, ethyl, n-butyl, 1-phenylethyl, 2-phenylethyl, 3-methoxybutoxycarbonylmethyl, tetrahydrofuran-2-ylmethyl, tetrahydrothiophen-2-ylmethyl, ethoxycarbonylmethyl, 2-hydroxy-5-(1,1,3,3-tetramethylbutyl)phenyl, 4-hydroxyphenyl, 4-methylphenyl, 4-isopropoxyphenyl, 4-(tetrahydrofuran-2-ylmethoxy)phenyl, 2,2,2-trifluoroacetoxyphenyl, 3,5-diisopropyl-4-hydroxyphenyl, 3,5-di-tert-butyl-4-hydroxy-phenyl, 3-methyl-4-hydroxyphenyl, 2-methyl-4-hydroxyphenyl, 5-tert-butyl-4-hydroxy-2-methylphenyl, 4-(tetrahydrofuran-2-ylmethoxy)phenyl, 4-(tetrahydrofuran-3-ylmethoxy)-phenyl, 4-(tetrahydrothiophen-2-ylmethoxy)phenyl, or 4-(tetrahydrothiophen-3-ylmethoxy)phenyl.

Specific examples for $R_5$ are $C_1$-$C_8$alkyl such as methyl, n-butyl, n-octyl; $C_1$-$C_4$alkoxy-$C_1$-$C_4$alkyl such as ethoxycarbonylmethyl, methoxycarbonylethyl, methoxycarbonylmethyl; $C_1$-$C_4$alkoxy-$C_1$-$C_4$alkoxy-C(=O)—$C_1$-$C_6$alkyl such as 3-methoxybutoxycarbonylmethyl; (5- or 6-memberd heterocycloalkyl)-$C_1$-$C_4$alkyl such as tetrahydrofuran-2-ylmethyl; naphthalene-$C_1$-$C_4$alkyl such as naphthalene-1-ylmethyl; phenyl-$C_1$-$C_4$alkyl such as benzyl, 1-phenylethyl, phenethyl; phenyl-$C_1$-$C_4$alkyl, where the alkyl moiety is substituted by benzoyl such as 2-oxo-1,2-diphenylethyl; phenyl-$C_1$-$C_4$alkyl, where the phenyl moiety is substituted by 1, 2, 3, 4 or 5 radicals selected from nitro, chlorine, hydroxy, $C_1$-$C_{10}$alkyl, $C_1$-$C_4$alkoxy, $C_1$-$C_4$alkoxycarbonyl, $C_1$-$C_4$alkoxy-$C_1$-$C_4$alkoxycarbonyl, hydroxy-$C_1$-$C_4$alkoxycarbonyl, benzyloxycarbonyl, C(=O)N($C_1$-$C_8$alkyl)$_2$ such as 2-chlorobenzyl, 2-methylbenzyl, 3-methylbenzyl, 3,4-dichlorobenzyl, 3,5-dichlorobenzyl, 3-hydroxybenzyl, 3-methoxybenzyl, 3-methoxybenzyl, 4-methylbenzyl, 4-nitrobenzyl, 4-(diisopropylaminocarbonyl)benzyl, 2-methoxy-1-methyl-ethoxycarbonylbenzyl, 4-(2-ethoxycarbonyl)benzyl, 4-(2-hydroxyethoxycarbonyl)benzyl, 4-(2-methoxy-1-methylethoxycarbonyl)benzyl, 4-benzyloxycarbonylbenzyl, benzoyl-$C_1$-$C_4$alkyl such as 2-oxo-2-phenylethyl; phenoxy-$C_1$-$C_4$alkyl such as 2-phenoxyethyl, benzyloxycarbonyl-$C_1$-$C_4$-alkyl such as 2-benzyloxycarbonylpropyl; phenyl; phenyl which is substituted by 1, 2, 3, 4 or 5 radicals selected from OH and $C_1$-$C_{10}$alkyl such as 4-hydroxyphenyl, 4-isopropoxyphenyl, 4-hydroxy-2-methyl-5-tert-butyl-phenyl, 4-hydroxy-3-methyl-phenyl, or 2-hydroxy-5(1,1,3,3-tetramethylbutyl)-phenyl.

Specific examples for $R_6$ are $C_1$-$C_8$alkyl such as methyl, n-butyl, n-octyl; $C_1$-$C_4$alkoxy-$C_1$-$C_6$alkyl such as methoxycarbonylethyl; benzyloxycarbonyl-$C_1$-$C_4$-alkyl such as 2-benzyloxycarbonylpropyl; phenyl; phenyl which is substituted by 1, 2, 3, 4 or 5 radicals selected from OH, $C_1$-$C_4$fluoroalkanoyloxy, (5- or 6-membered heterocycyloalkyl)-$C_1$-$C_4$alkoxy, $C_1$-$C_6$alkoxy, and $C_1$-$C_{10}$alkyl such as 2-hydroxy-5(1,1,3,3-tetramethylbutyl)-phenyl, 4-(2,2,2-trifluoroacetoxy)phenyl, 3,5-diisopropyl-4-hydroxyphenyl, 3-methoxyphenyl, 4-(tetrahydrofuran-2-ylmethoxy)phenyl, 4-hydropxyphenyl, 4-hydroxy-2-methyl-5-tert-butyl-phenyl, 4-hydroxy-2-methyl-phenyl, 4-hydroxy-3-methyl-phenyl, 4-hydroxyphenyl, 4-isopropoxyphenyl; phenyl-$C_1$-$C_4$alkyl such as benzyl; phenyl-$C_1$-$C_4$alkyl, where the phenyl moiety is substituted by 1, 2, 3, 4 or 5 radicals selected from $C_1$-$C_4$alkyl such as 4-methylbenzyl.

Preference is given to compounds of the formula I, where $R_5$ and $R_6$ are identical. Likewise preference is given to compound of the formula I, where $R_5$ is different from $R_6$.

Likewise preferred among these are compounds of the general formula I where $R_4$ and $R_5$ or $R_5$ and $R_6$ or $R_4$ and $R_6$ together form a straight-chain $C_4$-$C_5$ alkylene chain, thus forming, together with the sulfur atom to which they are bound, a 5- or 6-membered saturated ring which may be fused to one phenyl ring. In particular, $R_4$ and $R_5$ together with the sulfur atom to which they are bound form a tetrahydrothiophen-1-yl or 1,3-dihydrobenzo[c]thiophen-2-yl radical.

With respect to the intended use of the compounds of formula I, the substituents $R_4$, $R_5$ and $R_6$ independently of one another and preferably in combination have the following meanings:

$R_4$ is selected from the group of the formula A as defined above, where $R_{25}$ and $R_{26}$ are each independently of one another selected from hydrogen, $C_1$-$C_{12}$alkyl and phenyl; and $R_{27}$, $R_{28}$, $R_{29}$, $R_{30}$ and $R_{31}$ are each independently of one another selected from hydrogen, F, Cl, Br, I, $NO_2$, $OR_{20}$, $COOR_{22}$, $CONR_{23}R_{24}$, $C_2$-$C_{12}$alkenyl and phenyl or two radicals $R_{27}$ and $R_{28}$, and/or $R_{28}$ and $R_{29}$ and/or $R_{29}$ and $R_{30}$ and/or $R_{30}$ and $R_{31}$ bound on adjacent carbon atoms may be together a group selected from $CH_2CH_2CH_2$—, —$CH_2CH_2CH_2CH_2$— and —CH=CH—CH=CH—, thus forming, together with the carbon atoms to which they are bound, a 5- or 6-membered ring;

the group of the formula B as defined above, where $R_{33}$ and $R_{34}$ are each independently of one another selected from hydrogen, $C_1$-$C_{12}$alkyl and phenyl; and $R_{35}$, $R_{36}$ and $R_{37}$ are independently of one another selected from hydrogen, F, Cl, $C_1$-$C_{12}$alkyl, $C_2$-$C_{12}$alkenyl and phenyl; $C_3$-$C_{12}$cycloalkyl which may be substituted by one or more radicals selected from F, Cl, Br, I, $C_1$-$C_{12}$alkyl, $OR_{20}$, $COR_{21}$, $COOR_{22}$ and $CONR_{23}R_{24}$; $C_1$-$C_{12}$-alkyl which may be substituted by one or more radicals selected from F, Cl, Br, I, $OR_{20}$, $COR_{21}$, $COOR_{22}$, $CONR_{23}R_{24}$, $C_3$-$C_{12}$cycloalkyl and $C_2$-$C_9$heterocyclyl.

$R_7$ and $R_8$ are independently of one another selected from $C_1$-$C_{12}$alkyl, which is unsubstituted or substituted by one or more radicals selected from F, Cl, Br, I, $OR_{20}$, $COR_{21}$, $COOR_{22}$, $CONR_{23}R_{24}$, heterocycloalkyl, $C_3$-$C_8$cycloalkyl, phenyl and naphthyl, where the two last-mentioned radicals are unsubstituted or substituted by 1, 2, 3, 4, or 5 radicals selected from F, Cl, Br, I, $NO_2$, $C_1$-$C_{12}$alkyl, $OR_{20}$, $COOR_{22}$ and $CONR_{23}R_{24}$;

$C_3$-$C_{12}$cycloalkyl, which is unsubstituted or substituted by one or more radicals selected from F, Cl, Br, I, $OR_{20}$, $COR_{21}$, $COOR_{22}$, $CONR_{23}R_{24}$, $C_2$-$C_9$heterocyclyl, $C_3$-$C_8$cycloalkyl, phenyl and naphthyl, where the two last-mentioned radicals are unsubstituted or substituted by 1, 2, 3, 4, or 5 radicals selected from F, Cl, Br, I, $NO_2$, $C_1$-$C_{12}$-alkyl, $OR_{20}$, $COOR_{22}$ and $CONR_{23}R_{24}$; and phenyl, which is unsubstituted or substituted by one, two, three, four or five radicals selected from F, Cl, Br, I, $C_1$-$C_{10}$-alkyl, $SR_{19}$ and $OR_{20}$.

More preferably, with respect to the intended use of the compounds of the formula Ia, the substituents $R^1$, $R^2$, $R^3$ and $R^4$ in combination have the following meanings:

$R_4$ is a group of the formula A as defined above; a group of the formula B as defined above; $C_3$-$C_8$cycloalkyl; $C_1$-$C_6$alkyl; $C_1$-$C_4$alkoxy-(CO)—$C_1$-$C_4$alkyl; (5- or 6-membered saturated heterocycloalkyl)-$C_1$-$C_4$alkyl; or phenoxy-$C_1$-$C_4$alkyl;

$R_5$ is $C_1$-$C_8$alkyl; $C_1$-$C_4$alkoxy-$C_1$-$C_4$alkyl; $C_1$-$C_4$alkoxy-$C_1$-$C_4$alkoxy-C(=O)—$C_1$-$C_6$alkyl; (5- or 6-memberd heterocycloalkyl)-$C_1$-$C_4$alkyl; naphthalene-$C_1$-$C_4$alkyl, phenyl-$C_1$-$C_4$alkyl; phenyl-$C_1$-$C_4$alkyl; phenyl-$C_1$-$C_4$alkyl, where the phenyl moiety is substituted by 1, 2, 3, 4 or 5 radicals selected from nitro, chlorine, hydroxy, $C_1$-$C_{10}$alkyl, $C_1$-$C_4$alkoxy, $C_1$-$C_4$alkoxycarbonyl, $C_1$-$C_4$alkoxy-$C_1$-$C_4$alkoxycarbonyl, hydroxy-$C_1$-$C_4$alkoxycarbonyl, benzyloxycarbonyl and C(=O)N($C_1$-$C_8$alkyl)$_2$; benzoyl-$C_1$-$C_4$alkyl; phenoxy-$C_1$-$C_4$alkyl; benzyloxycarbonyl-$C_1$-$C_4$alkyl; phenyl; phenyl which is substituted by 1, 2, 3, 4 or 5 radicals selected from OH and $C_1$-$C_{10}$alkyl;

$R_6$ is $C_1$-$C_8$alkyl; $C_1$-$C_4$alkoxy-$C_1$-$C_6$alkyl; benzyloxycarbonyl-$C_1$-$C_4$alkyl; phenyl; phenyl which is substituted by 1, 2, 3, 4 or 5 radicals selected from OH, $C_1$-$C_4$-fluoroalkanoyloxy, (5- or 6-membered heterocycloalkyl)-$C_1$-$C_4$alkoxy, $C_1$-$C_6$alkoxy and $C_1$-$C_{10}$alkyl; phenyl-$C_1$-$C_4$alkyl; phenyl-$C_1$-$C_4$alkyl, where the phenyl moiety is substituted by 1, 2, 3, 4 or 5 radicals selected from $C_1$-$C_4$alkyl such as 4-methylbenzyl A further preferred embodiment relates to those compounds of the formula I, where $R_4$ is a group of the formula A or a group of the formula B, where the group of the formula A and the group B are as defined above and preferably have one of the preferred meanings;

$R_5$ is $C_1$-$C_8$alkyl; $C_1$-$C_4$alkoxy-$C_1$-$C_4$alkyl; $C_1$-$C_4$alkoxy-$C_1$-$C_4$alkoxy-C(=O)—$C_1$-$C_6$alkyl; (5- or 6-memberd heterocycloalkyl)-$C_1$-$C_4$alkyl; naphthalene-$C_1$-$C_4$-alkyl, phenyl-$C_1$-$C_4$alkyl; phenyl-$C_1$-$C_4$alkyl, where the phenyl moiety is substituted by 1, 2, 3, 4 or 5 radicals selected from nitro, chlorine, hydroxy, $C_1$-$C_{10}$alkyl, $C_1$-$C_4$alkoxy, $C_1$-$C_4$alkoxycarbonyl, $C_1$-$C_4$alkoxy-$C_1$-$C_4$alkoxycarbonyl, hydroxy-$C_1$-$C_4$alkoxycarbonyl, benzyloxycarbonyl and C(=O)N($C_1$-$C_8$alkyl)$_2$; benzoyl-$C_1$-$C_4$alkyl; phenoxy-$C_1$-$C_4$alkyl; benzyloxycarbonyl-$C_1$-$C_4$alkyl; phenyl; phenyl which is substituted by 1, 2, 3, 4 or 5 radicals selected from OH and $C_1$-$C_{10}$alkyl;

$R_6$ is $C_1$-$C_8$alkyl; $C_1$-$C_4$alkoxy-$C_1$-$C_6$alkyl; benzyloxycarbonyl-$C_1$-$C_4$alkyl; phenyl; phenyl which is substituted by 1, 2, 3, 4 or 5 radicals selected from OH, $C_1$-$C_4$ fluoroalkanoyloxy, (5- or 6-membered heterocycloalkyl)-$C_1$-$C_4$alkoxy, $C_1$-$C_6$ alkoxy and $C_1$-$C_{10}$alkyl; phenyl-$C_1$-$C_4$alkyl; phenyl-$C_1$-$C_4$alkyl, where the phenyl moiety is substituted by 1, 2, 3, 4 or 5 radicals selected from $C_1$-$C_4$alkyl such as 4-methylbenzyl.

A particular preferred embodiment relates to compounds of the formula I, where $R_4$ is benzyl, $C_1$-$C_4$alkyl, $C_5$-$C_8$cycloalkyl, 3-methylbut-2-enyl or tetrahydrofuran-2-ylmethyl;

$R_5$ is benzyl; and $R_6$ is benzyl.

In particular preferred are the compounds as denoted in the examples below.

A further preferred embodiment of the present invention relates to a heat-curable composition comprising at least one compound of the formula Ia. In the compounds of the formula Ia, $R_7$, $R_8$, $R_9$ and $R_{10}$ can be identical or different. Preferably, $R_7$ and $R_9$ are identical and $R_8$ and $R_{10}$ are identical.

Preference is given to compounds of the formula Ia, where $R_7$, $R_8$, $R_9$ and $R_{10}$ are independently of one another selected from $C_1$-$C_{12}$alkyl; $C_1$-$C_{12}$alkyl, which is substituted by one or more identical or different radicals $R_{2a}$, where $R_{2a}$ is as defined above; $C_3$-$C_{12}$cycloalkyl; $C_3$-$C_{12}$cycloalkyl, which is substituted by one or more identical or different radicals $R_{2b}$, where $R_{2b}$ is as defined above; phenyl; and phenyl, which is substituted by one, two, three, four or five radicals $R_{2c}$, where $R_{2c}$ is as defined above.

Preferred among these are compounds of the formula Ia, where $R_7$ and/or $R_8$ and/or $R_9$, and/or $R_{10}$ are $C_1$-$C_{12}$alkyl which is unsubstituted or is partly or completely halogenated and/or has 1, 2 or 3 identical or different radicals $R_{2a}$ selected from $OR_{20}$, $COR_{21}$, $COOR_{22}$, $CONR_{23}R_{24}$, $C_2$-$C_9$heterocyclyl, $C_3$-$C_8$cycloalkyl, phenyl and naphthyl, where the two last-mentioned radicals are unsubstituted or substituted by 1, 2, 3, 4, or 5 identical or different radicals selected from $C_1$-$C_{12}$-alkyl, F, Cl, Br, I, $NO_2$, $OR_{20}$, $COOR_{22}$, and $CONR_{23}R_{24}$. $R_{20}$, $R_{22}$, $R_{23}$ and $R_{24}$ are as defined above and preferably have one of the meanings being preferred. Examples are $C_1$-$C_6$alkyl such as methyl, ethyl, n-propyl, isopropyl, n-butyl, sec-butyl, tert-butyl, n-pentyl or hexyl, in particular methyl, ethyl, n-propyl or n-butyl Likewise, in a particular preferred embodiment $R_7$ and/or $R_8$ and/or $R_9$, and/or $R_{10}$ are $C_1$-$C_6$fluoroalkyl; $C_1$-$C_6$chloroalkyl; $C_1$-$C_4$alkoxy-$C_1$-$C_6$alkyl; phenoxy-$C_1$-$C_6$alkyl; benzoyl-$C_1$-$C_6$alkyl; phenyl-$C_1$-$C_6$alkyl, where the alkyl moiety of phenylalkyl is substituted by benzoyl; $C_1$-$C_4$alkoxycarbonyl-$C_1$-$C_6$alkyl; $C_1$-$C_4$alkoxy-$C_1$-$C_4$alkoxycarbonyl-$C_1$-$C_6$alkyl; $C_3$-$C_8$cycloalkyl-$C_1$-$C_6$alkyl; naphthyl-$C_1$-$C_6$alkyl; heterocyclyl-$C_1$-$C_6$alkyl, wherein heterocyclyl is a 5- to 6-membered saturated heterocyclic ring comprising besides carbon atoms one or two heteroatoms selected from O and S; phenyl-$C_1$-$C_6$alkyl, in which the phenyl moiety of phenylalkyl is unsubstituted or substituted by 1, 2, 3, 4 or 5 identical or different radicals selected from F, Cl, Br, I, OH, $NO_2$, $C_1$-$C_{10}$alkyl, $C_1$-$C_4$alkoxy, $C_2$-$C_9$heterocyclyl-$C_1$-$C_4$alkoxy, $C_1$-$C_4$fluoroalkanoyloxy, hydroxy-$C_1$-$C_4$alkoxycarbonyl, $C_1$-$C_4$alkoxycarbonyl, $C_1$-$C_4$alkoxy-$C_1$-$C_4$alkoxycarbonyl, benzyloxycarbonyl and C(=O)N($C_1$-$C_8$-alkyl)$_2$. Examples are $C_1$-$C_4$fluoroalkyl; $C_1$-$C_4$ chloroalkyl; $C_1$-$C_4$alkoxy-$C_1$-$C_8$alkyl such as 2-methoxy-ethyl or 3-methoxypropyl; phenoxy-$C_1$-$C_4$alkyl such as phenoxymethyl, 2-phenoxyethyl or 3-phenoxypropyl; benzoyl-$C_1$-$C_4$alkyl such as 2-oxo-2-phenylethyl, 3-oxo-3-phenylpropyl or 4-oxo-4-phenylbutyl; phenyl-$C_1$-$C_4$alkyl, where the alkyl moiety of phenylalkyl is substituted by benzoyl such as 2-oxo-1,2-diphenylethyl, 3-oxo-1,3-diphenylpropyl or 4-oxo-1,4-diphenylbutyl; $C_1$-$C_4$alkoxycarbonyl-$C_1$-$C_4$alkyl such as methoxycarbonylmethyl, ethoxycarbonylmethyl, 2-methoxycarbonylethyl, 2-ethoxycarbonylethyl, 3-methoxycarbonylpropyl, 3-ethoxycarbonylpropyl, 4-methoxycarbonylbutyl or 4-ethoxycarbonylbutyl; $C_1$-$C_4$alkoxy-$C_1$-$C_4$alkoxycarbonyl-$C_1$-$C_4$alkyl such as 3-methoxybutoxycarbonylmethyl, 3-methoxybutoxycarbonylethyl, 3-ethoxybutoxycarbonylmethyl or 3-ethoxybutoxycarbonylethyl; $C_3$-Cecycloalkyl-$C_1$-$C_6$alkyl such as cyclohexylmethyl, 2-cyclohexylethyl, cyclopentylmethyl or 2-cyclopentylethyl; naphthyl-$C_1$-$C_4$alkyl such as 1-naphthylmethyl, 2-napthylmethyl, 1-(naphthalene-1-yl)ethyl, 1-(naphthalene-2-yl)ethyl, 2-(naphthalene-1-yl)ethyl or 2-(naphthalene-2-yl)ethyl; $C_2$-$C_9$heterocyclyl-$C_1$-$C_4$alkyl such as tetrahydrofuran-2-ylmethyl, tetrahydrofuran-3-ylmethyl, 2-(tetrahydrofuran-2-yl)ethyl, 2-(tetrahydrofuran-3-yl)ethyl, 3-(tetrahydrofuran-2-yl)propyl, 3-(tetrahydrofuran-3-yl)propyl, tetrahydrothiophen-2-ylmethyl, tetrahydrothiophen-3-yl-methyl, 2-(tetrahydrothiophen-2-yl)ethyl, 2-(tetrahydrothiophen-3-yl)ethyl, 3-(tetrahydrothiophen-2-yl)propyl or 3-(tetrahydrothiophen-3-yl)propyl; phenyl-$C_1$-$C_2$alkyl, in which the phenyl moiety of phenylalkyl is unsubstituted or substituted by 1 or 2 identical or different radicals selected from fluorine, chlorine, $C_1$-$C_4$alkyl, $C_1$-$C_4$alkoxy, ($C_1$-$C_4$alkoxy)carbonyl, C(O)O—($C_1$-$C_4$alkyl-OH), and C(O)N($C_1$-$C_8$alkyl)$_2$; phenyl-$C_1$-$C_4$alkyl, where the phenyl moiety of phenylalkyl is substituted by 1 or 2 chlorines such as 2-chlorobenzyl, 3-chlorobenzyl, 4-chlorobenzyl, 2,4-dichlorobenzyl, 3,4-dichlorbenzyl, 3,5-dichlorobenzyl, 2-(2-chlorophenyl)ethyl, 2-(3-chlorophenyl)ethyl, 2-(4-chlorophenyl)ethyl, 2-(2,4-dichlorophenyl)ethyl, 2-(3,5-dichlorophenyl)ethyl or 2-(3,4-dichlorophenyl)ethyl; phenyl-$C_1$-$C_4$alkyl, where the phenyl moiety of phenylalkyl is substituted by hydroxy such as 2-hydroxybenzyl, 3-hydroxybenzyl, 4-hydroxybenzyl, 2-(2-hydroxyphenyl)ethyl, 2-(3-hydroxyphenyl)ethyl or 2-(4-hydroxyphenyl); phenyl-$C_1$-$C_4$-alkyl, where the phenyl moiety of phenylalkyl is substituted by 1 or 2 $C_1$-$C_{10}$alkyl groups such as 2-, 3- or 4-methylbenzyl, 2-, 3-, 4-ethylbenzyl, 2-, 3- or 4-propylbenzyl, 2-, 3- or 4-butylbenzyl, 2,4-dimethylbenzyl or 3,5-dimethylbenzyl; phenyl-$C_1$-$C_4$alkyl, where the phenyl moiety of phenylalkyl is substituted by 1 or 2 $C_1$-$C_4$alkoxy groups such as 2-, 3- or 4-methoxybenzyl, 2-, 3-, 4-ethoxybenzyl, 2-, 3- or 4-propoxybenzyl, 2-, 3- or 4-butoxybenzyl, 2,4-dimethoxybenzyl or 3,5-dimethoxybenzyl; phenyl-$C_1$-$C_4$-alkyl, where the phenyl moiety of phenylalkyl is substituted by $C_1$-$C_4$alkoxycarbonyl such as 2-ethoxycarbonylbenzyl, 3-ethoxycarbonylbenzyl, 4-ethoxycarbonylbenzyl, 2-(2-ethoxycarbonylphenyl)ethyl, 2-(3-ethoxycarbonylphenyl)ethyl or 4-(3-ethoxycarbonylphenyl)ethyl, phenyl-$C_1$-$C_4$alkyl, where the phenyl moiety of phenylalkyl is substituted by hydroxy-$C_1$-$C_4$alkoxycarbonyl such as 4-(2-hydroxyethoxycarbonyl) benzyl, 2-(4-(2-hydroxyethoxycarbonylphenyl)ethyl; phenyl-$C_1$-$C_4$-alkyl, where the phenyl moiety of phenylalkyl is substituted by C(=O)N($C_1$-$C_8$-alkyl)$_2$ such as 4-dimethylcarbamoylbenzyl, 4-diethylcarbamoylbenzyl, 4-diisopropylcarbamoylbenzyl, 2-(4-dimethylcarbamoylphenyl)ethyl, 2-(4-diethylcarbamoylphenyl)ethyl or 2-(4-diisopropylcarbamoylphenyl)ethyl.

Likewise preferred among these are compounds of the general formula Ia, where $R_7$ and/or $R_8$ and/or $R_9$, and/or $R_{10}$ are $C_3$-$C_{12}$cycloalkyl, which is unsubstituted or has 1, 2 or 3 identical or different radicals $R_{2b}$ selected from F, Cl, Br, I, $OR_{20}$, $COR_{21}$, $COOR_{22}$, $CONR_{23}R_{24}$, $C_2$-$C_9$heterocyclyl, $C_3$-$C_8$cycloalkyl, phenyl and naphthyl, where the two last-mentioned radicals may be substituted by 1, 2, 3, 4, or 5 different or identical radicals selected from F, Cl, Br, I, NO$_2$, $C_1$-$C_{12}$-alkyl, $OR_{20}$, $COOR_{22}$ and $CONR_{23}R_{24}$. $R_{20}$, $R_{22}$, where $R_{23}$ and $R_{24}$ are as defined above and preferably have one of the meanings being preferred. Examples are $C_3$-$C_8$cycloalkyl such as cyclopropyl, cyclobutyl, cyclopentyl, cyclohexyl or cyclheptyl; $C_3$-$C_8$cycloalkyl which is substituted by one, two or three of identical or different radicals selected from F, Cl, Br, I, $C_1$-$C_8$-alkyl, $OR_{20}$, $COOR_{22}$ and $CONR_{23}R_{24}$, where $R_{20}$, $R_{22}$, where $R_{23}$ and $R_{24}$ are as defined above.

Likewise preferred among these are compounds of the formula Ia where $R_7$ and/or $R_8$ and/or $R_9$, and/or $R_{10}$ are phenyl, which is unsubstituted or has 1, 2, 3, 4 or 5 identical or different radicals $R_{2c}$ selected from F, Cl, Br, I, $C_1$-$C_{10}$-alkyl, $SR_{19}$ and $OR_{20}$. $R_{19}$ and $R_{20}$ are as defined above and preferably have one of the meanings being preferred.

More preferably, $R_7$ and/or $R_8$ and/or $R_9$, and/or $R_{10}$ are phenyl which is unsubstituted or substituted by 1, 2, 3, 4 or 5 identical or different radicals which are selected from the group consisting of F, Cl, Br, I, OH, NO$_2$, $C_1$-$C_{10}$alkyl, $C_1$-$C_4$alkoxy, $C_2$-$C_9$heterocyclyl-$C_1$-$C_4$alkoxy, $C_1$-$C_4$fluoroalkanoyloxy, hydroxy-$C_1$-$C_4$alkoxycarbonyl, $C_1$-$C_4$alkoxycarbonyl, $C_1$-$C_4$alkoxy-$C_1$-$C_4$alkoxycarbonyl, benzyloxycarbonyl and C(=O)N($C_1$-$C_8$-alkyl)$_2$. Examples are phenyl which is unsubstituted or substituted by 1 or 2 identical or different radicals selected from fluorine, chlorine, hydroxy, nitro, $C_1$-$C_{10}$alkyl, $C_1$-$C_4$alkoxy, $C_1$-$C_4$fluoralkylcarbonyloxy and (heterocyclyl)-$C_1$-$C_4$alkoxy, where the heterocyclyl moiety is a 5- to 6-membered saturated heterocyclic ring comprising besides carbon atoms one or two heteroatoms selected from O or S. Examples are phenyl substituted by one, two, three or four $C_1$-$C_{10}$alkyl groups such as 2-methylphenyl, 3-methylphenyl, 4-methylphenyl, 2-ethylphenyl, 3-ethylphenyl, 4-ethylphenyl, 2-, 3-, 4-n-propylphenyl, 2-, 3-, 4-isopropylphenyl, 2-, 3-, 4-butylphenyl, 2-(1,1,3,3-tetramethylbutyl)phenyl, 3-(1,1,3,3-tetramethylbutyl)phenyl, 4-(1,1,3,3-tetramethylbutyl)phenyl, 2,4-dimethylphenyl, 3,5-dimethylphenyl or 3,5-diisopropylphenyl; phenyl substituted by OH such as 2,5-hydroxyphenyl, 3-hydroxyphenyl or 4-hydroxyphenyl; phenyl substituted by one, two, three or four groups selected from OH and $C_1$-$C_{10}$alkyl such as 2-hydroxy-5-(1,1,3,3-tetramethylbutyl)phenyl, 3,5-diisopropyl-4-hydroxyphenyl, 5-tert-butyl-4-hydroxy-2-methylphenyl and 3,5-di-tert-butyl-4-hydroxyphenyl; phenyl which is substituted by $C_2$-$C_9$heterocyclyl-CO—$C_2$alkoxy such 2-(tetrahydrofuran-2-ylmethoxy)phenyl, 3-(tetrahydrofuran-2-ylmethoxy)phenyl, 4-(tetrahydrofuran-2-ylmethoxy)phenyl, 2-(tetrahydrofuran-3-ylmethoxy)phenyl, 3-(tetrahydrofuran-3-ylmethoxy)phenyl, 4-(tetrahydrofuran-3-ylmethoxy)phenyl, 2-(tetrahydrothiophen-2-ylmethoxy)phenyl, 3-(tetrahydrothiophen-2-ylmethoxy)phenyl, 4-(tetrahydrothiophen-2-ylmethoxy)phenyl, 2-(tetrahydrothiophen-3-ylmethoxy)phenyl, 3-(tetrahydrothiophen-3-ylmethoxy)phenyl or 4-(tetrahydrothiophen-3-ylmethoxy)phenyl; phenyl substituted by $C_1$-$C_4$-fluoroalkanoyloxy such as 2,2,2-trifluoroacetoxyphenyl or 3,3,3-trifluoropropionyloxyphenyl.

In particular $R_7$, $R_8$, $R_9$ and $R_{10}$ are independently of one another selected from $C_1$-$C_4$alkyl, phenyl and phenyl, which is substituted by one or more radicals selected from OH and $C_1$-$C_4$-alkyl, in particular methyl, ethyl, n-butyl, phenyl and 4-hydroxyphenyl Preference is also given to those compounds of the formula Ia, where M in formula Ia is $C_1$-$C_{12}$alkylene, which may be substituted by one or more identical or different radicals $R_{Ma}$ and/or may be interrupted by one or more non-adjacent groups $R_{Mb}$, or phenylene which may be substituted by one or more radicals $R_{Mc}$, where $R^{Ma}$ and $R^{Mc}$ are as defined above.

In particular M is

C$_1$-C$_{12}$ alkylene;

C$_1$-C$_{12}$alkylene, which is substituted by one or more, e.g. 1, 2 or 3, identical or different radicals selected from F, Cl, Br, I, C$_1$-C$_{12}$alkyl, C$_1$-C$_{12}$haloalkyl, CN, SR$_{19}$, OR$_{20}$, COR$_{21}$, COOR$_{22}$, CONR$_{23}$R$_{24}$, C$_6$-C$_{10}$aryl, heteroaryl or C$_6$-C$_{10}$aryl which is substituted by one or more identical or different radicals selected from F, Cl, Br, I, C$_1$-C$_{12}$ alkyl, C$_1$-C$_{12}$haloalkyl, CN, NO$_2$, SR$_{19}$, OR$_{20}$, COR$_{21}$, COOR$_{22}$ and CONR$_{23}$R$_{24}$;

C$_1$-C$_{12}$alkylene, interrupted by one or more, e.g. 1, 2 or 3, identical or different non-adjacent groups selected from O, S, —O-phenylene or phenylene where the 2 last-mentioned groups may be substituted by one or more radicals selected from F, Cl, Br, I, C$_1$-C$_{12}$ alkyl, C$_1$-C$_{12}$ haloalkyl, SR$_{19}$, OR$_{20}$, COR$_{21}$, COOR$_{22}$, CONR$_{23}$R$_{24}$ and phenyl;

C$_1$-C$_{12}$alkylene, which is substituted by one or more, e.g. 1, 2 or 3, identical or different radicals selected from F, Cl, Br, I, C$_1$-C$_{12}$-alkyl, C$_1$-C$_{12}$-haloalkyl, CN, SR$_{19}$, OR$_{20}$, COR$_{21}$, COOR$_{22}$, CONR$_{23}$R$_{24}$, C$_6$-C$_{10}$aryl, heteroaryl or C$_6$-C$_{10}$aryl which is substituted by one or more identical or different radicals selected from F, Cl, Br, I, C$_1$-C$_{12}$alkyl, C$_1$-C$_{12}$haloalkyl, CN, NO$_2$, SR$_{19}$, OR$_{20}$, COR$_{21}$, COOR$_{22}$ and CONR$_{23}$R$_{24}$, and interrupted by one or more snon-adjacent groups selected from O, S, —O-phenylene or phenylene where the 2 last-mentioned groups may be substituted by one or more radicals selected from F, Cl, Br, I, C$_1$-C$_{12}$alkyl, C$_1$-C$_{12}$haloalkyl, SR$_{19}$, OR$_{20}$, COR$_{21}$, COOR$_{22}$, CONR$_{23}$R$_{24}$ and phenyl, or phenylene which may be substituted by one or more, e.g. 1, 2 or 3, identical or different radicals selected from F, Cl, Br, I, C$_1$-C$_{12}$alkyl, C$_1$-C$_{12}$haloalkyl, SR$_{19}$, OR$_{20}$, COR$_{21}$, COOR$_{22}$, CONR$_{23}$R$_{24}$ and phenyl;

where R$_{19}$, R$_{20}$, R$_{22}$, R$_{23}$ and R$_{24}$ are as defined above and have preferably one of the preferred meanings.

More preferably, M is C$_2$-C$_8$alkylene interrupted by one, two, three, four, five or six non-adjacent groups selected from O, S, —O-phenylen and phenylene, where the last mentioned groups may be substituted by 1, 2, 3 or 4 radicals selected from C$_1$-C$_{12}$alkyl, C$_1$-C$_{12}$haloalkyl, CN, NO$_2$, SR$_{19}$, OR$_{20}$, COR$_{21}$, COOR$_{22}$, CONR$_{23}$R$_{24}$ and phenyl. In particular, M is C$_2$-C$_8$alkylene which is interrupted by one phenylene group or C$_2$-C$_8$-alkylene which is interrupted by 1, 2, 3 or four groups selected from oxygen and —O-phenylene. Even more preferably, M is —CH$_2$—C$_6$H$_4$—O—CH$_2$CH$_2$CH$_2$O—C$_6$H$_4$—CH$_2$— or —CH$_2$—C$_6$H$_4$—CH$_2$—.

Y is for example O, O(CO), O(CO)O, O(CO)NR$_{11}$, O(CO)NR$_{11}$(CO), OSO$_2$ or O(CS)NR$_{11}$; in which for each of these radicals the oxygen atom is directly bound to X;

or Y is for example, O(CO), O(CO)O, O(CO)NR$_{11}$, OSO$_2$ or O(CS)NR$_{11}$.

R$_1$ is for example hydrogen, C$_3$-C$_{30}$cycloalkyl, C$_3$-C$_{30}$cycloalkyl-C$_1$-C$_{18}$alkyl, C$_1$-C$_{18}$alkyl, C$_4$-C$_{30}$cycloalkenyl, or is C$_2$-C$_{18}$alkyl which is interrupted by one or more O, CO, O(CO) or NR$_{14}$(CO), or is C$_3$-C$_{30}$cycloalkyl which is interrupted by one or more O, CO, O(CO) or NR$_{14}$(CO), or R$_1$ is NR$_{12}$R$_{13}$, or is C$_3$-C$_{30}$ cycloalkyl-C$_1$-C$_{18}$alkyl which is interrupted by one or more O, CO, O(CO) or NR$_{14}$(CO), wherein the C$_1$-C$_{18}$alkyl, C$_4$-C$_{30}$cycloalkenyl, interrupted C$_2$-C$_{18}$alkyl, interrupted C$_3$-C$_{30}$acycloalkyl-C$_1$-C$_{18}$alkyl are unsubstituted or are substituted by one or more Z$_1$.

Z$_1$ as substituent for C$_1$-C$_{18}$alkyl preferably is methyl, ethyl, propyl, butyl or hexyl.

Z$_1$ as substituent for C$_4$-C$_{30}$cycloalkenyl preferably is cyclopentenyl, cyclohexenyl,

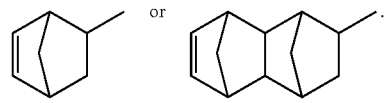

Z$_1$ as substituent for C$_3$-C$_{30}$cycloalkyl-C$_1$-C$_{18}$alkyl preferably is

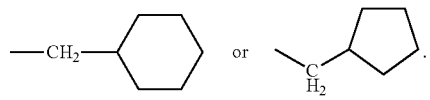

R$_2$ and R$_3$ for example independently of each other are C$_3$-C$_{30}$cycloalkylene, C$_1$-C$_{18}$alkylene, C$_4$-C$_{30}$cycloalkenylene or a direct bond, provided that R$_2$ and R$_3$ are not both simultaneously a direct bond. In particular R$_2$ and R$_3$ are C$_1$-C$_{18}$alkylene.

General Process to Prepare the Novel Compounds

The afore-described novel sulfonium compounds of the general formula I, Ia and Ib can generally be prepared by ion-exchange reaction, for example, between the desired sulfonium chloride, bromide, iodide, hydrogen sulfonate, sulfonate, tetrafluoroborate, trifluoroacetate, tosylate, methanesulfonate or methylsulfonate and the desired sulfonate salts having ammonium, tetramethylammonium, pyridinium, sodium, lithium, potassium or silver as cation. These reactions are usually carried out in an inert solvent, for example water, an alkanol such as methanol or ethanol, a halogenated hydrocarbons such as dichloromethane, trichloromethane or chlorobenzene, an aliphatic hydrocarbon, such as pentane, hexane, cyclohexane and petroleum ether, an aromatic hydrocarbon, such as toluene, o-, m- and p-xylene, an ether, such as diethyl ether, methyl ethyl ketone, diisopropyl ether, tert-butyl methyl ether, dioxane, dimethoxyethane, anisole and tetrahydrofuran, a nitrile, such as acetonitrile and propionitrile, a ketone such as acetone, methyl ethyl ketone, diethyl ketone and tert-butyl methyl ketone, and also ethyl acetate or dimethylformamide (DMF), or mixture of such solvents. The combination of solvents, for example water and ethyl acetate, affords a two phase system. Such two phase systems are also suitable for the ion-exchange reaction. These reactions are well known to those skilled in the art, and are generally carried out at temperatures in the range of 0 to 120° C., preferably 0 to 60° C.

The anions A and A$_1$ as defined above are for example prepared as described in WO 2011104127.

The sulfonium salts required as starting materials can be obtained by a variety of methods described, for instance, by George Andrew Olah in Onium ions, p. 167 or by J. V. Crivello in Advances in Polymer Science 62, 1-48, (1984). General methods for preparation of trialkyl(aryl)sulfonium involve alkylation or arylation of dialkyl, diaryl, and alkylaryl sulfides with alkyl halides, or with alkyl halides/silver tetrafluoroborate, alkyl halides/HCl, dialkyl sulfonates, sulfonic acid esters, alcohols in the presence of strong protic acids, esters/trifluoromethanesulfonic acid, benzyl halides/Lewis acids, or trialkyl(aryl)oxonium salts as respective alkylating (arylating) agents.

The desired sulfonium salts can, for example, be prepared by condensation of sulfoxides with aryl compounds in the presence of strong acids such as sulfuric acid, polyphosphoric acid, methanesulfonic acid or the like so that sulfonium salts of the strong acid used are formed.

Examples of components (a) in the composition of the present invention are compounds having at least one group selected from an epoxy group, oxetane group and vinyl ether group.

Suitable examples are:

compounds comprising an oxygen- or sulphur-containing saturated heterocycle, ethylenically unsaturated compounds which are polymerisable by a cationic mechanism, prepolymers of phenol-formaldehyde resins, acrylic resins, alkyd resins or polyester resins containing heat curable functional groups, mixtures of heat curable compounds and compounds polymerisable by a different mechanism, e.g. free radicals or UV irradiation, mixtures thereof.

Compounds (a) which comprise an oxygen- or sulphur-containing saturated heterocycle preferably comprise at least one heterocycle having 3, 4, 5 or 6 ring members. Preferred compounds (a) which comprise an oxygen- or sulphur-containing saturated heterocycle are selected from compounds containing at least one epoxy group, oxetanes, oxolanes, cyclic acetals, cyclic lactones, thiiranes, thietanes and mixtures thereof.

Suitable compounds (a) containing one epoxy group are ethylene oxide, propylene oxide, styrene oxide, phenyl glycidyl ether, butyl glycidyl ether, etc.

In a preferred embodiment of the invention, compound (a) is selected from epoxy resins. The term "epoxy resin" as utilized in the description of the curable compositions of the present invention, is understood in a broad sense and includes any monomeric, dimeric, oligomeric or polymeric epoxy material containing a plurality (2, 3, 4, 5, 6 or more than 6) of epoxy groups. The term "epoxy resins" also encompasses prepolymers which comprise two or more epoxide groups, wherein some of the epoxide groups (oxiran rings) may also have been opened to a hydroxyl group. The term also identifies part-cured epoxy resins, i.e., epoxy resins which have been crosslinked by means of suitable hardeners. If component (a) is a part cured epoxy resin, it still contains heat-curable epoxy groups that are still capable of undergoing cationic polymerization. The term "epoxy resins" also encompasses modified epoxy resins, such as esterified or etherified epoxy resins, obtainable for example by reaction with carboxylic acids or alcohols. Again, modified epoxy resins that are employed in a composition according to the invention still contain heat curable epoxy groups that are still capable of undergoing cationic polymerization. A complete definition of the term "epoxy resins" is found for example in Ullmann's Encyclopedia of Industrial Chemistry, 5th edition, on CD-ROM, 1997, Wiley-VCH, in the "Epoxy Resins" section.

The majority of commercial epoxy resins are prepared by coupling epichlorohydrin onto compounds which possess at least two reactive hydrogen atoms, such as polyphenols, monoamines and diamines, aminophenols, heterocyclic imides and amides, aliphatic diols or polyols or dimeric fatty acids. Epoxy resins derived from epichlorohydrin are referred to as glycidyl-based resins.

The majority of epoxy resins available commercially at the present time derive from the diglycidyl ether of bisphenol A (DGEBA resins) and possess the general formula

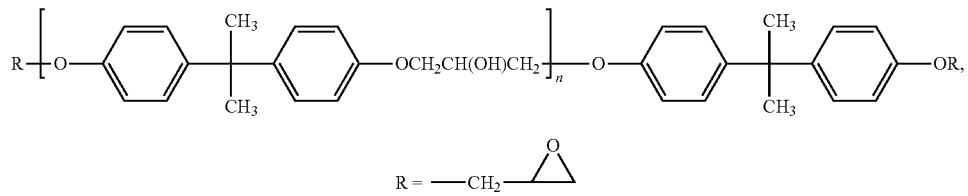

n is 0 to approximately 40.

Other important epoxy resins are phenol-based and cresol-based epoxy novolaks, examples being epoxy resins which derive from the diglycidyl ether of bisphenol F. Novolaks are prepared by the acid-catalyzed condensation of formaldehyde and phenol or cresol. The epoxidation of the novolaks leads to epoxy novolaks.

Other classes of glycidyl-based epoxy resins derive from glycidyl ethers of aliphatic diols, such as butane-1,4-diol, hexane-1,6-diol, pentaerythritol or hydrogenated bisphenol A; aromatic glycidylamines, an example being the triglycidyl adduct of paminophenol or the tetraglycidylamine of methylenedianilide; heterocyclic glycidylimides and amides, e.g., triglycidyl isocyanurate; and glycidyl esters, such as the diglycidyl ester of dimeric linoleic acid, for example.

The epoxy resins (a) may also derive from other epoxides (non-glycidyl ether epoxy resins). Examples are the diepoxides of cycloaliphatic dienes, such as 3,4-epoxycyclohexylmethyl 3,4-epoxycyclohexanecarboxylate and 4-epoxyethyl-1,2-epoxycyclohexane Examples of commercially available epoxy resins are bisphenol A type epoxy resin such as Epiculon N-3050, N-7050, N-9050 produced by Dainippon Ink & Chemicals Inc., XAC-5005, GT-7004, 6484T, 6099; bisphenol S type epoxy resin such as BPS-200 produced by Nippon Kayaku Co., Ltd., EPX-30 produced by ACR Co., Epiculon EXA-1514 produced by Dainippon Ink & Chemicals Inc., etc.; bisphenol F type epoxy resin such as YDF-2004, YDF2007 produced by Tohto Kasei Co., etc.; bisphenol fluorene type epoxy resin such as OGSOL PG, PG-100, EG, EG-210 produced by Osaka Gas Chemicals; a diglycidyl phthalate resin such as Blemmer DGT produced by Nip-pon Oil and Fats Co., Ltd., etc.; heterocyclic epoxy resin such as TEPIC produced by Nissan Chemical Industries, Ltd., Araldite PT810 produced by Huntsman, etc.; a bixy-lenol type epoxy resin such as YX-4000 produced by Yuka Shell Co., etc.; biphenol type epoxy resin such as YL-6056 produced by Yuka Shell Co., etc.; tetraglycidyl xylenoylethane resin such as ZX-1063 produced by Tohto Kasei Co., etc.; novolak type epoxy resin such as EPPN-201, EOCN-103, EOCN-1020, EOCN-1025 and BRRN produced by Nippon Kayaku Co., Ltd., ECN-278, ECN-292 and ECN-299 produced by Asahi Chemical Industry Co., Ltd., GY-1180, ECN-1273 and ECN-1299 produced by Ciba Specialty Chemicals Inc., YDCN-220L, YDCN-220HH, YDCN-702, YDCN-704, YDPN-601 and YDPN-602 produced by Tohto Kasei Co., Epiculon-673, N-680, N-695, N-770 and N-775 produced by Dainippon Ink & Chemicals Inc., etc.; novolak type epoxy resin of bisphenol A such as EPX-8001, EPX-8002, EPPX-8060 and EPPX-8061 produced by Asahi Chemical Industry Co., Ltd., Epiculon N-880 produced by Dainippon Ink & Chemicals Inc., etc.; chelate type epoxy resin such as EPX-49-69 and EPX-49-30 produced by Adeka, etc.; glyoxal type epoxy resin such as YDG-414 produced by Tohto Kasei Co., etc.; amino group-containing epoxy resin such as YH-1402 and ST-110 produced by Tohto Kasei Co., YL-931 and YL-933 produced by Yuka Shell Co., etc.; rubber-modified epoxy resin such as Epiculon TSR-601 produced by Dainippon Ink & Chemicals Inc., EPX-84-2 and EPX-4061 produced by Adeka, etc.; dicyclopentadiene phenolic type epoxy resin such as DCE-400 produced by Sanyo-Kokusaku Pulp Co., Ltd., etc.; silicone-modified epoxy resin such as X-1359 produced by Adeka, etc.; ε-caprolactone-modified epoxy resin such as Plaque G-402 and G-710 produced by Dicel Chemical Industries, Ltd., etc. and others.

Other important epoxy resins are copolymers of ethylenically unsaturated compounds which comprise at least one epoxide group in the molecule such as glycidyl acrylate, glycidyl methacrylate, 3,4-epoxybutyl acrylate, 3,4-epoxybutyl methacrylate, vinylbenzylglycidyl ether and allyl glycidyl ether and ethylenically unsaturated compounds which comprise no epoxide group in the molecule.

Examples of the ethylenically unsaturated compounds which comprise no epoxide group in the molecule are unsubstituted and substituted alkyl esters of acrylic and methacrylic acid which comprise 1 to 20 carbon atoms in the alkyl radical, more particularly methyl acrylate, methyl methacrylate, ethyl acrylate, ethyl methacrylate, butyl acrylate, butyl methacrylate, 2-ethylhexyl acrylate, 2-ethylhexyl methacrylate, 2-hydroxyethyl acrylate, 2-hydroxyethyl methacrylate, 2-hydroxypropyl acrylate, 2-hydroxypropyl methacrylate, 4-hydroxybutyl acrylate, 4-hydroxybutyl methacrylate, 1,2-dihydroxyethyl acrylate, and 1,2-dihydroxyethyl methacrylate.

Further examples of the ethylenically unsaturated compounds which comprise no epoxide groups in the molecule are unsaturated acids, such as acrylic acid and methacrylic acid, acid amides, such as acrylamide and methacrylamide, vinyl aromatic compounds, such as styrene, methylstyrene, hydroxystyrene and vinyitoluene, nitriles, such as acrylonitrile and methacrylonitrile, vinyl halides and vinylidine halides, such as vinyl chloride and vinylidine fluoride, vinyl esters, such as vinyl acetate, and hydroxyl-containing monomers, such as hydroxyethyl acrylate and hydroxyethyl methacrylate.

Further examples of the ethylenically unsaturated compounds which comprise no epoxide groups in the molecule are N-phenylmaleimide, N-cyclohexylmaleimide and N-benzylmaleimide.

Suitable oxetanes (a) are trimethylene oxide, 3,3-dimethyloxetane, 3,3-di(chloromethyl) oxetane, 3-ethyl-3-hydroxymethyl oxetane, 2-ethyihexyloxetane, xylene bisoxetane, 3-ethyl-3[[(3-ethyloxetane-3-yl)methoxy]methyl] oxetane, etc.

Examples of commercially available oxetanes are for example Aron Oxetane OXT-101, OXT-212, OXT-121, OXT-221 from Toagosei Co., Ltd.

Other important oxetane resins are copolymers of ethylenically unsaturated compounds which comprise at least one oxetane group in the molecule such as 3-methyl-3-acryloyloxymethyl oxetane, 3-methyl-3-methacryloyloxymethyl oxetane, 3-ethyl-3-acryloyloxymethyl oxetane, and 3-ethyl-3-methacryloyloxymethyl oxetane and ethylenically unsaturated compounds which comprise no epoxide group in the molecule as mentioned above.

Suitable oxolanes (a) are tetrahydrofuran, 2,3-dimethyltetrahydrofuran, etc.

Suitable cyclic acetals (a) are trioxan, 1,3-dioxolane, 1,3,6-trioxacyclooctane, etc.

Suitable cyclic lactones (a) are β-propiolactone, ε-caprolactone, the alkyl derivatives of β-propiolactone and ε-caprolactone, etc.

Suitable thiiranes (a) are ethylene sulfide, 1,2-propylene sulfide, thioepichlorohydrin, etc.

Suitable thietanes (a) are 1,3-propylene sulfide, 3,3-dimethyithietane, etc.

Further suitable compounds (a) are ethylenically unsaturated compounds which are polymerisable by a cationic mechanism, selected from mono- and diolefins, styrene, allylbenzene, vinylcyclohexane, vinyl ethers, vinyl esters, dihydropyran derivatives and mixtures thereof.

Suitable mono- and diolefins (a) are isobutene, 1-octene, butadiene, isoprene, etc.

Suitable vinyl ethers (a) are vinyl methyl ether, vinyl isobutyl ether, ethylene glycol divinyl ether, etc.

Suitable vinyl esters (a) are vinyl acetate, vinyl stearate, etc.

Suitable dihydropyran derivatives (a) are 3,4-dihydro-2H-pyran-2-carboxylic acid esters, 2-hydroxymethyl-3,4-dihydro-2H-pyran, etc.

Further suitable compounds (a) are mixtures of heat curable compounds and compounds polymerisable by a different mechanism, e.g. free radicals or UV irradiation.

Suitable are e.g. mixtures of epoxy resins with monomeric or oligomeric acrylic or methacrylic acid esters. In this case, the polymerisation takes place by a cationic mechanism and a different mechanism, e.g. free radical polymerization or UV cure The heat curable composition according to the invention may comprise at least one further component selected from solvents; reactive diluents; ethylenically unsaturated compounds, being different from reactive diluents; binder resins being different from compounds (a), reactive diluents and from ethylenically unsaturated compounds; photoinitiators; free radical initiators; sensitizers; pigments; fillers; dispersants; thermal curing promoters being different from compounds of formula I, Ia and Ib; further additives; and mixtures thereof.

Below, compounds which may be derived from acrylic acid and methacrylic acid are in some cases abbreviated by adding the syllable "(meth)" in the compound derived from acrylic acid.

The heat curable compositions of the invention may be either solvent-based or aqueous based. Solvent-based in this context means that the volatile constituents of the coating composition comprise substantially, i.e., to an extent of at least 51% by weight, preferably at least 60% by weight, based on the volatile constituents overall, of organic solvents (including reactive diluents if present). Water-based in this context means that the volatile constituents of the coating composition comprise substantially, i.e., to an extent of at least 51% by weight, preferably at least 60% by weight, more particularly at least 80% by weight, based on the volatile constituents overall, of water. Coating compositions are composed in principle of volatile and nonvolatile constituents. The nonvolatile fraction of the coating compositions can be determined to DIN EN ISO 3251 with the following test conditions: initial mass of (1±0.1) g, then 24 hours of drying at 23° C., thereafter (in accordance with DIN EN ISO 3251 appendix B1) 1 hour at 105° C. The volatile fraction is given by the difference between total amounts and nonvolatile fraction.

In contrast to solvent-based coating compositions, aqueous coating compositions have substantially water as their solvent, and little or no quantities of organic solvents. In the aqueous coating compositions the fraction of organic solvents is preferably not more than 30% by weight, more preferably not more than 20% by weight, and more particularly not more than 10% by weight, based on the total weight of the volatile constituents comprised in the coating composition.

Suitable solvents for solvent-based coating compositions are aliphatic, alicyclic, heterocyclic, aromatic, and heteroaromatic hydrocarbons, esters of aliphatic carboxylic acids with $C_2$-$C_{10}$alkanols or polyalkylene glycols, ketones, lactones, lactams, ethers, monohydric or polyhydric alcohols, and mixtures thereof. The solvents are then preferably selected from toluene, xylenes, solvent naphtha, white spirit, ligroin, ethyl acetate, propyl acetate, butyl acetate, amyl acetate, methoxyethyl acetate, methoxypropyl acetate, ethoxyethyl acetate, ethoxypropyl acetate, ethyl ethoxypropionate, acetone, methyl ethyl ketone, methyl isobutyl ketone, cyclopentanone, cyclohexanone, N-methylpyrrolidone, dipropylene glycol, dibutylglycol, methanol, ethanol, n-propanol, iso-propanol, butanol, propylene glycol monomethyl ether acetate, prolylene glycol monomethyl ether, γ-butyrolactone, ethyl lactate and mixtures thereof.

Preferably the boiling point of the solvent is such, that in the course of the curing of the heat curable composition they evaporate from the resin composition In an alternative embodiment, the polymerization can also be carried out solventless (in the molten state).

Sometimes the use of solvents results in an unwanted reduction in volume of the obtained resin (shrinking) or in the formation of pores, which may have a negative influence on the mechanical properties of the cured material, such as the fracture resistance or the surface properties.

The disadvantages of the conventional solvents can be circumvented through the use of reactive diluents. Similarly to solvents, reactive diluents are substances of low molecular mass, but differ from conventional solvents in having functional groups which are able to react with complementary functional groups of the employed component (a) and/or with the functional groups of an additional hardener, to form covalent bonds. Reactive diluents likewise lower the viscosity of the resin. They do not evaporate in the course of curing, and therefore, in the course of curing, are incorporated covalently into the resin matrix as it forms. Suitable reactive diluents are low molecular weight compounds having a molecular weight of preferably not more than 250 daltons, e.g., in the range from 100 to 250 daltons. The reactive diluents preferably contain oxirane groups, more preferably glycidyl groups, in the form, for example, of glycidyl ether groups, glycidyl ester groups or glycidyl amide groups. The epoxide functionality, i.e., the number of epoxide groups per molecule, in the case of the reactive diluents is typically in the range from 1 to 4, more particularly in the range from 1.1 to 3, in particular 12 to 2.5.

Preferred among these are, in particular, glycidyl ethers of aliphatic or cycloaliphatic alcohols which have preferably 1, 2, 3 or 4 OH groups and 2 to 20 or 4 to 20 C atoms, and also glycidyl ethers of aliphatic polyetherols which have 4 to 20 C atoms. Examples of such are as follows:

- glycidyl ethers of saturated alkanols having 2 to 20 C atoms, such as $C_2$-$C_{20}$-alkyl glycidyl ethers such as 2-ethylhexyl glycidyl ether, for example;
- glycidyl ethers of saturated alkanepolyols having 2 to 20 C atoms, examples being the glycidyl ethers of 1,4-butanediol, of 1,6-hexanediol, trimethylolpropane or of pentaerythritol, the aforementioned glycidyl ether compounds generally having an epoxide functionality in the range from 1 to 3.0 and preferably in the range from 1.2 to 2.5;
- glycidyl ethers of polyetherols having 4 to 20 C atoms, examples being glycidyl ethers of diethylene glycol, triethylene glycol, tetraethylene glycol, dipropylene glycol, and tripropylene glycol;
- glycidyl ethers of cycloaliphatic alcohols having 5 to 20 C atoms, such as, for exampe, bisglycidyl ethers of cyclohexane-1,4-diyl, the bisglycidyl ether of ring-hydrogenated bisphenol A or of ring-hydrogenated bisphenol F;
- glycidyl ethers of polyalkylene oxides having 2 to 4 C atoms such as polyethylene oxide or polypropylene oxide;

and mixtures of the above substances.

An overview over reactive diluents can be found in P. K. T. Oldring (Editor), Chemistry & Technology of UV & EB Formulations for Coatings, Inks & Paints, Vol. II, Chapter III: Reactive Diluents for UV & EB Curable Formulations, Wiley and SITA Technology, London 1997. The disclosure of this document is incorporated herein by reference.

The heat curable composition according to the invention may comprise at least one ethylenically unsaturated compound. The resulting composition is curable not only by heat but also a different curing mechanism, in particular UV irradiation. UV- and heat-curable compositions are also called dual cure compositions.

Suitable ethylenically unsaturated compounds may additionally comprise at least one heat curable functional group. Preferred are ethylenically unsaturated compounds which comprises in the molecule at least one epoxide group, more particularly in the form of a glycidyl ether group. Suitable ethylenically unsaturated compounds may also comprises no epoxide group in the molecule. Preferred are esters of acrylic acid or methacrylic acid.

Examples of the ethylenically unsaturated monomers which comprise at least one epoxide group in the molecule are glycidyl acrylate, glycidyl methacrylate, and allyl glycidyl ether.

Examples of ethylenically unsaturated monomers which comprise no epoxide group in the molecule are alkyl esters of acrylic and methacrylic acid which comprise 1 to 20 carbon atoms in the alkyl radical, more particularly methyl acrylate, methyl methacrylate, ethyl acrylate, ethyl methacrylate, butyl acrylate, butyl methacrylate, 2-ethylhexylacrylate, and 2-ethylhexyl methacrylate.

Further examples of ethylenically unsaturated monomers which comprise no epoxide groups in the molecule are unsaturated acids, such as acrylic acid and methacrylic acid, acid amides, such as acrylamide and methacrylamide, vinyl aromatic compounds, such as styrene, methylstyrene, and vinyitoluene, nitriles, such as acrylonitrile and methacrylonitrile, vinyl halides and vinylidine halides, such as vinyl chloride and vinylidine fluoride, vinyl esters, such as vinyl acetate, and hydroxyl-containing mono-mers, such as hydroxyethyl acrylate and hydroxyethyl methacrylate.

Examples of monomers with at least two ethylenically unsaturated double bonds and no epoxide groups in the molecule are esters of acrylic acid which are derived from diols or polyols, preferably aliphatic polyhydric polyalcohols and alkoxylation products thereof. They are preferably selected from hexanediol diacrylate, hexanediol dimethacrylate, octanediol diacrylate, octanediol dimethacrylate, nonanediol diacrylate, nonanediol dimethacrylate, decanediol diacrylate, decanediol dimethacrylate, cyclo-hexanediol di(meth)acrylate, bis(hydroxymethylethyl)cyclohexane di(meth)acrylate, trimethylolethane tri(meth)acrylate, trimethylolpropane tri(meth)acrylate, pentaerythritol tetra(meth)acrylate, dipentaerythritol penta(meth)acrylate, dipentaerythritol hexa(meth)acrylate and mixtures thereof.

The heat curable composition according to the invention may comprise at least one binder resin being different from the afore-mentioned compounds (a), reactive diluents and ethylenically unsaturated compounds.

The additional binder resins may be physically drying polymer compositions, self-crosslinking polymer compositions, UV-curable polymer compositions, thermosetting polymer compositions, polymer compositions crosslinkable by addition of a crosslinker (2-component dispersions), or dual-cure systems.

Self-crosslinking or crosslinkable polymers contain reactive groups which react withy one another or with a crosslinker substance comprised therein, with formation of bonds. The self-crosslinking polymers may be based on ethylenically unsaturated monomers. Also suitable are polyurethane-based polymers, which through incorporation of corresponding monomers and/or through selection of the stoichiometry of the polyurethane-forming monomers contain the desired functional groups.

In the case of thermosetting polymer compositions, the composition may be based on a polyurethane or based on a polymer of ethylenically unsaturated monomers, the polymer component containing hydroxyl groups, keto groups, urea groups, epoxide groups and/or carboxyl groups, and at least one low molecular mass or polymeric crosslinker having at least two reactive groups as specified above.

Examples of binder resins are homo- and co-polymers of acrylates and methacrylates, for example copolymers of methyl methacrylate/ethyl acrylate/methacrylic acid, poly(methacrylic acid alkyl esters), poly(acrylic acid alkyl esters); phenolic resins, cellulose derivatives, such as cellulose esters and ethers, for example cellulose acetate, cellulose acetate butyrate, methyl cellulose, ethyl cellulose; polyvinyl butyral, polyvinyl formal, polyolefins, cyclised rubber, polyethers, such as polyethylene oxide, polypropylene oxide, polytetrahydrofuran; polystyrene, polycarbonate, polyurethane, chlorinated polyolefins, polyvinyl chloride, copolymers of vinyl chloride/vinylidene chloride, copolymers of vinylidene chloride with acrylonitrile, methyl methacrylate and vinyl acetate, polyvinyl acetate, copoly(ethylene/vinyl acetate), polymers such as polycaprolac-tame and poly(hexamethyleneadipamide), polyesters such as poly(ethylene glycol terephthalate) and poly(hexamethylene glycol succinate); and polyamides.

Photoinitiators are preferably used in an amount of from 0.001% to 15% by weight, more preferably from 0.01 to 10% by weight, based on the total weight of the heat curable composition according to the invention.

Suitable photoinitiators for the heat curable compositions according to the invention are so called cationic photoinitiator that produce reactive cations (e.g. Lewis or Bronsted acids) under the action of light and thus are suitable to initiate cationic polymerization. Suitable cationic photoinitiators are derived from stable organic onium salts, particularly with nitrogen, phosphorus, oxygen, sulfur, selenium or iodine as central atom of the cation. Preferred are aromatic sulfonium and iodonium salts with complex anions, phenacylsulfonium salts, hydroxylphenylsulfonium salts and sulfoxonium salts. It is also possible to employ organic silicon compounds which release a silanol upon UV irradiation in the presence of an aluminous organic compound.

Initiators of this kind are, for example, the products available commercially under the brand names Irgacure® 250 from BASF SE, CYRACURE® UVI-6990, CYRACURE®UVI-6974 from Union Carbide, DEGACURE® KI 85 from Degussa, SP-55, SP-150, SP-170 from Adeka, GE UVE 1014 from General Electric, SarCat® CD 1012, SarCat® KI-85, SarCat® CD 1010; SarCat® CD 1011 from Sartomer.

Suitable cationic photoinitiator are also onium salts which are excited via a sensitizer. Suitable sensitizers are mentioned in the following UV-curable compositions generally comprise at least one photoinitiator (radical photoinitiator) which is able to initiate the polymerization of ethylenically unsaturated double bonds. They include, for example, benzophenone and its derivatives, such as 4-phenylbenzophenone and 4-chlorobenzophenone, Michler's ketone, anthrone, acetophenone derivatives, such as 1-benzoylcyclohexan-1-ol, 2-hydroxy-2,2-dimethylacetophenone, benzoin and benzoin ethers, such as methyl, ethyl, and butyl benzoin ether, benzil ketals, such as benzil dimethyl ketal, 2-methyl-1-(4-methyithiophenyl)-2-morpholinopropan-1-one, (4-morpholinobenzoyl)-1-benzyl-1-dimethylaminopropane, (4-morpholinobenzoyl)-1-(4-methylbenzyl)-1-dimethylaminopropane, anthraquinone and its derivatives, such as β-methylanthraquinone and tert-butylanthraquinone, oxime esters, such as 1,2-octanedione 1-[4-(phenylthio)phenyl]-2-(O-benzoyloxime) and ethanone 1-[9-ethyl-6-(2-methylbenzoyl)-9H-carbazol-3-yl]-1-(O-acetyloxime), acylphosphine oxides, such as 2,4,6-trimethylbenzoyldiphenylphosphine oxide, ethyl 2,4,6-trimethylbenzoyl-phenylphosphinate, and bisacylphosphine oxides, such as bis(2,4,6-trimethylbenzoyl)-phenylphosphine oxide. Initiators of this kind are, for example, the products available commercially under the brand names Irgacure® 184, Darocur® 1173, Irgacure® 127, Irgacure® 2959, Irgacure® 651, Irgacure® 907, Irgacure® 369, Irgacure®379, Irgacure® OXE01, Irgacure® OXE02, Lucirin® TPO, Irgacure® 819, Irgacure® 784, Irgacure® 754 from BASF SE, Adeka Optomer N-series N-1414, N-1717, N-1919 from Adeka or Genocure® from Rahn.

Suitable free-radical initiators for the heat curable compositions according to the invention are the peroxo and/or azo compounds customary for the purpose, examples being alkali metal or ammonium peroxidisulfates, diacetyl peroxide, dibenzoyl peroxide, succinyl peroxide, di-tert-butyl peroxide, tert-butyl perbenzoate, tert-butyl perpivalate, tert-butyl peroxy-2-ethylhexanoate, tert-butyl permaleate, cumene hydroperoxide, diisopropyl peroxidicarbamate, bis(o-toluoyl) peroxide, didecanoyl peroxide, dioctanoyl peroxide, dilauroyl peroxide, tert-butyl perisobutyrate, tert-butyl peracetate, di-tert-amyl peroxide, tert-butyl hydroperoxide, azobisisobutyronitrile, 2,2'-azobis(2-amidinopropane)-dihydrochloride or 2,2'-azobis(2-methylbutyronitrile). Mixtures of these initiators are suitable as well.

Compositions according to the invention based on compounds which contain ethylenically unsaturated double bonds may comprise at least one, which on exposure to elevated temperature produces polymerization of these groups and hence free-radical crosslinking. They include thermolabile free-radical initiators, such as organic peroxides, organic azo compounds, or C—C-cleaving initiators such as dialkyl peroxides, peroxocarboxylic acids, peroxodicarbonates, peroxide esters, hydroperoxides, ketone peroxides, azo dinitriles or benzpinacol silyl ethers Free radical initiators are preferably used in an amount of from 0.001% to 15% by weight, more preferably from 0.01 to 10% by weight, based on the total weight of the heat curable composition according to the invention.

Sensitizers are preferably used in an amount of from 0.001% to 15% by weight, more preferably from 0.01 to 10% by weight, based on the total weight of the heat curable composition according to the invention.

Suitable sensitizers are usually employed in combination with at least one of the afore-mentioned cationic photoinitiators or radical photoinitiators. Preferred sensitizers for cationic photoinitiators are polycyclic aromatic compounds, such as anthracene, naphthalene and derivatives thereof (see also U.S. Pat. No. 6,313,188, EP 0927726, WO 2006/073021, U.S. Pat. No. 4,997,717, U.S. Pat. No. 6,593,388, and WO 03/076491). A preferred combination comprises at least one sensitizer, selected from polycyclic aromatic compounds, and at least one iodonium photoinitiator. Preferred sensitizers for radical photoinitiators are aromatic compounds, such as thioxanthone, benzophenone, coumarin and derivatives thereof.

The heat curable composition of the invention may comprise at least one pigment. Suitable in principle are inorganic pigments, organic pigments, and mixtures thereof. The pigments may be color pigments, effect pigments, transparent pigments or mixtures thereof.

Examples of suitable inorganic pigments include white pigments such as titanium dioxide, preferably in the rutile form, barium sulfate, zinc oxide, zinc sulfide, basic lead carbonate, antimony trioxide, lithopones (zinc sulfide+barium sulfate) or colored pigments, examples being iron oxides, carbon black, graphite, zinc yellow, zinc green, ultramarine, manganese black, antimony black, manganese violet, Paris blue or Schweinfurt green. Suitable organic color pigments may come from a wide variety of dye classes with different chromophores, examples being anthraquinone dyes, monoazo and diazo dyes, indigo and indigoid dyes, quinophthalones, methine and azamethine dyes, naphthalimide dyes, naphthoquinone dyes, nitro dyes, quinacridone pigments, phthalocyanine pigments, isoindolinone pigments, and metal complex pigments, etc. Examples of suitable organic color pigments are indanthrene blue, chromophthal red, Irgazine orange, and Heliogen green.

Effect pigments used may be metal flake pigments such as commercial aluminum bronzes as per DE-A-36 36 183, chromated aluminum bronzes, and commercial stainless steel bronzes, and also nonmetallic effect pigments, such as pearlescent pigments and interference pigments, for example. Also suitable are synthetic white pigments with air inclusions for increasing light scattering, such as the Rhopaque® dispersions.

Other examples of suitable effect pigments are apparent from Römpp-Lexikon, Lacke und Druckfarben, Georg Thieme Veriag, 1998, page 176

The fraction of the pigments as a proportion of the heat curable composition may vary very widely. Advantageously the fraction is 1% to 95%, preferably 2% to 90%, more preferably 3% to 85%, and more particularly 4% to 80%, by weight, based in each case on the total weight of the heat curable composition of the invention.

Suitable fillers are organic and inorganic fillers, examples being aluminosilicates, such as feldspars, silicates, such as kaolin, talc, mica, magnesite, alkaline earth metal carbonates, such as calcium carbonate, in the form of calcite or chalk, for example, magnesium carbonate, dolomite, alkaline earth metal sulfates, such as calcium sulfate, silicon dioxide, etc. Suitable organic fillers are, for example, textile fibers, cellulose fibers, polyethylene fibers or wood flour. In coating materials, of course, finely divided fillers are preferred. The fillers may be used as individual components. In practice, mixtures of fillers have also proven particularly appropriate, examples being calcium carbonate/kaolin, calcium carbonate/talc. For further details refer to Römpp-Lexikon, Lacke und Druckfarben, Georg Thieme Verlag, 1998, pages 250 ff., "fillers". The fraction of the fillers as a proportion of the coating composition is preferably 0% to 95%, more preferably 0.5% to 90%, more particularly 1% to 75%, and especially 4% to 80%, by weight, based in each case on the total weight of the coating composition of the invention.

The heat curable composition of the invention may also comprise at least one dispersant. Suitable dispersants are in principle known emulsifiers and protective colloids (sur face active substances).

Suitable emulsifiers are anionic, nonionic, and cationic emulsifiers. Dispersants are used in particular if the heat curable composition comprises an aqueous medium. The term "aqueous medium" denotes water and mixtures of water and at least one water-miscible organic solvent. In a special embodiment, the heat curable composition is formulated as an aqueous coating composition.

Preferred are emulsifiers, whose relative molecular weights, in contrast to the protective colloids, are typically below 2000. They may be anionic, cationic or nonionic, preference being given to anionic emulsifiers and to a combination thereof with nonionic emulsifiers. The anionic emulsifiers include alkali metal salts and ammonium salts of alkyl sulfates (alkyl radical: $C_8$-$C_{12}$), of sulfuric monoesters with ethoxylated alkanols (EO degree: 2 to 50, alkyl radical: $C_{12}$-$C_{18}$) and with ethoxylated alkylphenols (EO degree: 3 to 50, alkyl radical: $C_4$-$C_9$), of alkylsulfonic acids (alkyl radical: $C_{12}$-$C_{18}$), of alkylarylsulfonic acids (alkyl radical: $C_9$-$C_{18}$), and of mono- and dialkyldiphenyl ether sulfonates, as are described in U.S. Pat. No. 4,269,749, for example. Suitable nonionic emulsifiers are araliphatic or aliphatic nonionic emulsifiers, examples being ethoxylated mono-, di-, and trialkylphenols (EO degree: 3 to 50, alkyl radical: $C_4$-$C_9$), ethoxylates of long-chain alcohols (EO degree: 3 to 50, alkyl radical: $C_8$-$C_{36}$), and polyethylene oxide/polypropylene oxide block copolymers. Preference is given to ethoxylates of long-chain alkanols (alkyl radical: $C_{10}$-$C_{22}$, average degree of ethoxylation: 3 to 50) and, of these, particular preference to those based on oxo process alcohols and natural alcohols having a linear or branched $C_{12}$-$C_{18}$ alkyl radical and a degree of ethoxylation of 8 to 50.

Suitable protective colloids are, for example, polyvinyl alcohols, starch derivates and cellulose derivatives, or copolymers comprising vinylpyrrolidone. A comprehensive description of further suitable protective colloids is found in Houben-Weyl, Methoden der organischen Chemie, volume XIV/1, Makromolekulare Stoffe, Georg-Thieme-Verlag, Stuttgart 1961, pp. 411-420.

Other examples of suitable dispersants are polymeric dispersants.

Polymeric dispersants include high molecular weight polymers with pigment affinic groups. Examples are: statistical co-polymers comprised from, for instance, styrene derivatives, (meth)acrylates and (meth)acrylamides, and such statistical co-polymers modified by post modification; block co-polymers and/or comb polymers comprised from, for instance, styrene derivatives, (meth)acrylates and (meth)acrylamides, and such block co-polymers and/or comb polymers modified by post modification; poly-ethylenimines, which for instance is crafted with polyesters; polyamines, which for instance is crafted with polyesters; and many kinds of (modified) polyurethanes.

Polymeric dispersants may also be employed. Suitable polymeric dispersants are, for example, BYK's DISPER-BYK® 101, 115, 130, 140, 160, 161, 162, 163, 164, 166, 168, 169, 170, 171, 180, 182, 2000, 2001, 2009, 2020, 2025, 2050, 2090, 2091, 2095, 2096, 2150, Ciba's Ciba® EFKA® 4008, 4009, 4010, 4015, 4046, 4047, 4050, 4055, 4060, 4080, 4300, 4310, 4330, 4340, 4400, 4401, 4402, 4403, 4406, 4500, 4510, 4520, 4530, 4540, 4550, 4560, Ajinomoto Fine Techno's PB®711, 821, 822, 823, 824, 827, Lubrizol's SOLSPERSE® 1320, 13940, 17000, 20000, 21000, 24000, 26000, 27000, 28000, 31845, 32500, 32550, 32600, 33500, 34750, 36000, 36600, 37500, 39000, 41090, 44000, 53095 and combinations thereof.

It is preferred to use BASF's EFKA® 4046, 4047, 4060, 4300, 4310, 4330, 4340, DISPERBYK® 161, 162, 163, 164, 165, 166, 168, 169, 170, 2000, 2001, 2020, 2050, 2090, 2091, 2095, 2096, 2105, 2150, PB®711, 821, 822, 823, 824, 827, SOLSPERSE® 24000, 31845, 32500, 32550, 32600, 33500, 34750, 36000, 36600, 37500, 39000, 41090, 44000, 53095 and combinations thereof as dispersant.

Suitable texture improving agents are, for example, fatty acids such as stearic acid or behenic acid, and fatty amines such as laurylamine and stearylamine. In addition, fatty alcohols or ethoxylated fatty alcohols, polyols such as aliphatic 1,2-diols or epoxidized soy bean oil, waxes, resin acids and resin acid salts may be used for this purpose.

Suitable pigment derivatives are, for example, copper phthalocyanine derivatives such as EFKA® 6745, Lubrizol's SOLSPERSE® 5000, 12000, BYK's SYNERGIST 2100 and azo derivatives such as EFKA® 6750, SOLSPERSE® 22000 and SYNERGIST 2105 The above mentioned dispersants and surfactants for pigments are for example employed in compositions of the present invention which are used as resist formulations, in particular in color filter formulations.

Where the heat curable compositions of the invention comprise at least one surface-active substance, the fraction thereof is typically 0.01% to 10% by weight, preferably 0.1% to 5% by weight, based on the total weight of the composition.

The heat curable composition according to the invention may comprise one or more additional thermal curing promotors, which are guided in a known way by the nature of the reactive functional groups in the binder.

Suitable thermal curing promotors catalysts are sulfonium and phosphonium salts of organic or inorganic acids, imidazole and imidazole derivatives, quatemary ammonium compounds, and amines.

Examples of commercially available thermal curing promoters are San-Aid SI series, SI-60L, SI-80L, SI-100L, SI-110L, SI-145, SI-150, SI-160, SI-180L produced by Sanshin Chemical.

The thermal curing promotors, where desired, are preferably used in an amount of from 0.001% by weight to about 10% by weight, based on the total weight of the heat curable composition according to the invention.

In a preferred embodiment there is no need for thermal curing promoters being different from compounds of formula I, Ia and Ib.

It is allowable to add a variety of known additives such as the following to the heat curable composition of this invention to modify certain application properties in view of a desired application.

Suitable further additives are selected from hardeners, crosslinkers, reinforcing materials, dyes, flow control assistants, UV stabilizers, heat stabilizers, weatherability improvers, rheology modifiers, flame retardants, antioxidants, discoloration inhibitors, biocides, antistatic agents, plasticizers, lubricants, slip additives, wetting agents, film-forming assistants, adhesion promoters, corrosion inhibitors, antifreeze agents, defoamers, mold release agents, photolatent acids, etc., and mixtures thereof.

They are each comprised in the quantities typical for such additives.

The composition according to the invention may contain at least one hardener. Hardeners are used in particular, if the compound (a) comprises an epoxy resin.

Suitable hardeners include aliphatic and aromatic polyamines, polyamidoamines, urons, amides, guanidines, aminoplasts and phenoplasts, polycarboxylic polyesters, polycarboxylic acids and polycarboxylic acid anhydrides, dihydroxy and polyhydroxy compounds, thiols, imidazoles, imidazolines, and certain isocyanates, and also latent polyfunctional hardeners.

Polyamine hardeners crosslink epoxy resins through reaction of primary or secondary amino functions of polyamines with terminal epoxide groups of the epoxy resins. Suitable polyamines are, for example, aliphatic polyamines such as ethylenediamine, 1,2- and 1,3-propylenediamine, neopentanediamine, hexamethylenediamine, octamethylenediamine, 1,10-diaminodecane, 1,12-diaminododecane, diethylenetriamine, triethylenetetramine, tetraethylenepentamine, and the like; cycloaliphatic diamines, such as 1,2-diaminocyclohexane, 1,3-bis(aminomethyl)cyclohexane, 1-methyl-2,4-diaminocyclohexane, 4-(2-aminopropan-2-yl)-1-methylcycohexan-1-amine, isophoronediamine, 4,4'-diaminodicyclohexylmethane, 3,3'-dimethyl-4,4'-diamino-dicyclohexylmethane, norbomanediamine, menthanediamine, menthenediamine and the like; aromatic diamines, such as tolylenediamine, xylylenediamine, more particularly meta-xylylenediamine, bis(4-aminophenyl)methane (MDA or methylenedianiline), bis(4-aminophenyl) sulfone (also known as DADS, DDS or dapsone), and the like; cy-clic polyamines, such as piperazine, N-aminoethylpiperazine and the like; polyether-diamines, examples being the reaction product of polypropylene oxide or polyethylene oxide or butylene oxide or pentylene oxide or poly(1,4-butanediol) or polytetrahydrofuran or mixtures of the 5 last-mentioned alkylene oxides with propylene oxide with am-monia, e.g., 4,7,10-trioxatridecane-1,3-diamine, 4,7,10-trioxatridecane-1,13-diamine, XTJ-500, XTJ-501, XTJ-511, XTJ-542, XTJ-559, XTJ-566, XTJ-568 (Huntsman), 1,8-diamino-3,6-dioxaoctane (XTJ-504 from Huntsman), 1,10-diamino-4,7-dioxadecane (XTJ-590 from Huntsman), 1,12-diamino-4,9-dioxadodecane (BASF), 1,3-diamino-4,7,10-trioxatridecane (BASF), polyetheramine T 5000, Jeffamines and the like; and polyamide diamines (amidopolyamines), which are obtainable through the reaction of dimeric fatty acids (e.g., dimeric linoleic acid) with low molecular mass polyamines, such as diethylenetriamine or triethylenetetramine A further class of suitable hardeners are those known as urons (urea derivatives), such as 3-(4-chlorophenyl)-1,1-dimethylurea (monuron), 3-(3,4-dichlorophenyl)-1,1-dimethylurea (diuron), 3-phenyl-1,1-dimethylurea (fenuron), 3-(3-chloro-4-methylphenyl)-1,1-dimethylurea (chlortoluron), and the like.

Suitable hardeners are also carbamides, such as tolyl-2,4-bis(N,N-dimethylcarbamide), and tetraalkylguanidines, such as N,N,N'N'-tetramethylguanidine.

Melamine-, urea-, and phenol-formaldehyde adducts, which are also referred to as aminoplasts or phenoplasts, respectively, form a further class of suitable hardeners.

Polycarboxylic polyesters as hardeners are being employed increasingly in powder coatings. The crosslinking takes place by virtue of the reaction of the free carboxyl groups e.g. with the epoxide groups of an epoxy resin.

Further polyfunctional hardeners comprise aromatic compounds having two or more hydroxyl groups. Examples of such are resins obtainable by the reaction of phenol or alkylated phenols, such as cresol, with formaldehyde, examples being phenol novolaks, cresol novolaks and dicyclopentadiene novolaks; furthermore, resins of nitro-gen-containing heteroaromatics, such as benzoguanamine-phenol-formaldehyde resins or benzoguanamine-cresol-formaldehyde resins, acetoguanamine-phenol-formaldehyde resins or acetoguanamine-cresol-formaldehyde resins, and melamine-phenol-formaldehyde resins or melamine-cresol-formaldehyde resins, and also hydroxylated arenes, such as hydroquinone, resorcinol, 1,3,5-trihydroxybenzene, 1,2,3-trihydroxybenzene (pyrogallol), 1,2,4-trihydroxybenzene (hydroxyhydroquinone), 3,4,5-trihydroxybenzoic acid (gallic acid) or derivatives thereof, 1,8,9-trihydroxyanthracene, (dithranol or 1,8,9-anthracenetriol), 1,2,10-trihydroxyanthracene (anthrarobin) and 2,4,5-trihydroxypyrimidine; additionally, alkanes substituted by hydroxylated arenes, such as triphenolmethane, triphenolethane and tetraphenolethane. Further examples are phosphinates and phosphonates derived from hydroquinone and naphthoquinone, as described in WO 2006/034445, hereby fully incorporated by reference.

Further polyfunctional hardeners comprise thiols, imidazoles, such as imidazole, 1-methylimidazole, 2-methylimidazole, 2-ethyl-4-methylimidazole, 1-cyanoethyl-imidazole and 2-phenylimidazole, and imidazolines, such as 2-phenylimidazoline.

Blocked isocyanates have more recently been used as latent hardeners for water-based coatings.

Dicyandiamide (dicy), $HN=C(NH_2)(NHCN)$, is a latent polyfunctional hardener frequently employed in powder coatings and electrical laminates.

Also suitable are reaction products of dicy with amines, known as bisguanidines, such as HAT 2844 from Vantico.

Further suitable latent polyfunctional hardeners are boron trifluoride-amine adducts such as $BF_3$-monoethylamine, and quaternary phosphonium compounds.

The composition according to the invention may contain at least one crosslinkers. Suitable hardeners further include melamine compounds, for example melamine, monomethyrol melamine, dimethyrol melamine, trimethyrol melamine, tetramethyrol melamine, pentamethyrol melamine, hexamethyrol melamine, monobutyrol melamine, dibutyrol melamine, tributyrol melamine, tetrabutyrol melamine, pentabutyrol melamine, hexabutyrol melamine, monomethoxymethyl melamine, dimethoxymethyl melamine, trimethoxymethyl melamine, tetramethoxymethyl melamine, pentamethoxymethyl melamine, hexamethoxymethyl melamine, monobutoxymethyl melamine, dibutoxymethyl melamine, tributoxymethyl melamine, tetrabutoxymethyl melamine, pentabutoxymethyl melamine, hexabutoxymethyl melamine and guanamine compounds, for example acetoguanamine, benzoguanamine, monomethyrol benzoguanamine, dimethyrol benzoguanamine, trimethyrol benzoguanamine, tetramethyrol benzoguanamine and alkylated methyrol benzoguanamines.

The heat curable composition of the invention may also comprise at least one dye as additive. The dyes in question may be, for example, the molecularly dispersely soluble dyes that are typical for such compositions, or solvent dye.

Suitable flow control assistants are, for example, modified silicone oils such as the Byk® products of Altana-Byk, or high molecular mass polyacrylates, such as the Resiflow® products of Worlée.

UV stabilizers (light stabilizers) suitable as additive are, for example, 4,4-diarylbutadienes, cinnamic esters, triazoles, triazines, benzophenones, diphenyl-cyanoacrylates, oxamides (oxalamides), oxanilides, etc. Suitable sterically hindered amines are, for example, 2,2,6,6-tetramethylpiperidine, 2,6-di-tert-butylpiperidine or derivatives thereof, an example being bis(2,2,6,6-tetramethyl-4-piperidyl) sebacate. UV 0 stabilizers are used typically in an amount of 0.1% to 5.0%, and preferably of 0.5% to 3.5%, by weight, based on the total weight of the heat curable composition.

Suitable wetting agents are, for example, siloxanes, fluorine-containing compounds, carboxylic monoesters, phosphoric esters, polyacrylic acids and their copolymers, or polyurethanes.

Examples of suitable film-forming assistants are cellulose derivatives.

The coating composition of the invention may also comprise as additive at least one rheology control additive. Suitable rheology control additives are described in, for example, WO 94/22968, EP-A-0 276 501, EP-A-0 249 201 or WO 97/12945. Also suitable are crosslinked polymeric microparticles of the kind disclosed in EP-A-0 008 127, for example; inorganic phyllosilicates, preferably smectites, more particularly montmorillonites and hectorites, such as aluminum magnesium silicates, sodium magnesium phyllosilicates and sodium magnesium fluorine lithium phyllosilicates of the montmorillonite type, or inorganic phyllosilicates such as aluminum magnesium silicates, sodium magnesium phyllosilicates and sodium magnesium fluorine lithium phyllosilicates of the montmorillonite type, silicas such as Aerosils, or synthetic polymers with ionic and/or associative groups, such as polyvinyl alcohol, poly(meth)acrylamide, crosslinked poly(meth)acrylic acid, polyvinylpyrrolidone, styrene-maleic anhydride or ethylene-maleic anhydride copolymers and their derivatives, or hydrophobically modified polyacrylates, or else polyurethane-based associative thickeners, of the kind described in Römpp-Lexikon, Lacke und Druckfarben, Georg Thieme Verlag, Stuttgart, N.Y., 1998, "thickeners", pp. 599-600, and in the textbook "Lackadditive" by Johan Bieleman, Wiley-VCH, Weinheim, N.Y., 1998, pp. 51-59 and 65.

Examples of suitable photolatent acids are quinonediazide compounds, for example 1,2-quinonediazidesulfonic acid ester compounds of polyhydroxy compounds. Preferred are compounds having a 1,2-quinonediazidesulfonyl group, e.g. a 1,2-benzoquinonediazide-4-sulfonyl group, a 1,2-naphthoquinonediazide-4-sulfonyl group, a 1,2-naphthoquinonediazide-5-sulfonyl group, a 1,2-naphthoquinonediazide-6-sulfonyl group or the like. Particularly preferred are compounds having a 1,2-naphthoquinonediazide-4-sulfonyl group or a 1,2-naphthoquinonediazide-5-sulfonyl group. In particular suitable are 1,2-quinonediazidesulfonic acid esters of (poly) hydroxyphenyl aryl ketones such as 2,3,4-trihydroxybenzophenone, 2,4,6-trihydroxybenzophenone, 2,3,4,4'-tetrahydroxybenzophenone, 2,2',3,4-tetrahydroxybenzo-phenone, 2,3,4,4'-tetrahydroxybenzophenone, 2,2',4,4'-tetrahydroxybenzophenone, 2,2',3,4,4'-pentahydroxybenzophenone, 2,2'3,2,6'-pentahydroxybenzophenone, 2,3,3',4,4'5'-hexahydroxybenzophenone, 2,3',4,4',5'6-hexahydroxybenzophenone and the like; 1,2-quinonediazidesulfonic acid esters of bis-[(poly)hydroxyphenyl]alkanes such as bis(4-hydroxyphenyl)ethane, bis(2,4-dihydroxyphenyl)ethane, 2,2-bis(4-hydroxyphenyl)propane, 2,2-bis(2,4-dihydroxyphenyl)propane, 2,2-bis-(2,3,4-tridroxyphenyl)propane and the like; 1,2-quinonediazidesulfonic acid esters of (poly)hydroxyphenylalkanes such as 4,4'-dihydroxytriphenylmethane, 4,4'4"-trihydroxytriphenylmethane, 4,4'5,5'-tetramethyl-2,2'2"-trihydroxytriphenylmethane, 2,2,5,5'-tetramethyl-4,4',437-trihydroxytriphenylmethane, 1,1,1-tris(4-hydroxyphenyl)ethane, 1,1-bis(4-hydroxyphenyl)-1-phenylethane, 1,1-bis(4-hydroxyphenyl)-1-(4-[1-(hydroxyphenyl)-1-methylethyl]phenyl)ethane and the like; 1,2-quinonediazidesulfonic acid esters of (poly) hydroxyphenylflavans such as 2,4,4-trimethyl-2',4',7-trihydroxy-2-phenylflavan, 2,4,4-trimethyl-2',4',5',6,7-pentahydroxy-2-phenyfflavan and the like Further examples of suitable coatings additives are described in the textbook "Lackadditive" by Johan Bieleman, Wiley-VCH, Weinheim, N.Y., 1998.

The compositions according to the invention are prepared by mixing of the components in apparatus conventional for this purpose.

The heat curable compositions according to the invention are outstandingly suitable as coating agents for substrates of any type.

Suitable substrates are metals (preferably metals of groups 8, 9, 10 or 11 of the periodic table, e.g. Au, Ag, Cu), oxidic materials (like glass, quartz, ceramics, $SiO_2$), insulating materials (e.g. $Si_3N_4$), semiconductors (e.g. doped Si, doped Ge, and GaAs), metal alloys (e.g. on the basis of Au, Ag, Cu, etc.), semiconductor alloys, polymers (e.g. polyvinylchloride, polyolefines, like polyethylene and polypropylene, polyesters, fluoropolymers, polyamides, polyurethanes, polyalkyl(meth)acrylates, polystyrene, rubber and mixtures and composites thereof), ceramics, glass, paper, wood, cloth, concrete, ceramic, etc.

The substrate can be a flexible or inflexible solid substrate with a curved or planar geometry, depending on the requirements of the desired application.

Coated substrates can be produced, for example, by preparing a heat curable composition according to the invention in form of a solution or suspension. The choice of a solvent and the concentration depends mainly on the type of composition and on the coating process.

The solution or suspension can be uniformly applied to a substrate by methods known to a person skilled in the art. Suitable is the application for example by spreading, spraying, dipping, rolling, brushing, knifecoating, whirier-coating, curtain coating methods, reverse-roll coating, electrostatic methods, etc.

The heat curable composition of the invention may be used as a primer, surfacer, pigmented topcoat or basecoat, or as a clearcoat. It may be used as the sole coating composition or in one or more layers of a multilayer coating. It is also especially suitable for coating pretreated substrates, such as metals with conventional primers, etc. The coating composition may be applied in one step or else in two or more steps, such as in 1, 2 or 3 steps, for example. A further possibility is to apply two or more coating compositions successively, for example, one or more primers in combination with one or more topcoats, so as to give a multicoat—for example, a 2-, 3-, 4- or 5-coat—coating system. Between the individual application steps it is possible to carry out drying and/or curing steps. Depending on the nature of the coating composition and of the desired coating, the coating compositions may also be applied wet on wet.

The amount of composition applied is guided in a conventional way by the desired properties of the treated surface, and is situated typically in the range from 1 to 500 $g/m^2$, reckoned as nonvolatile constituents of the coating composition. In the case of a multicoat system the amount of coating composition is typically 1 to 200 $g/m^2$ per coat.

The curing of the epoxy resins is accomplished, preferably, thermally by heating of the composition to a temperature of preferably 5 to 300° C., more preferably 20 to 250° C., even more preferably from 50 to 230° C., and more particularly 80 to 230° C. Which temperature is suitable depends on the particular compound (a), compound (b), and optionally compounds of the composition and on the desired cure rate. A suitable temperature range can be determined in each individual case by the skilled worker on the basis, for example, of simple preliminary tests.

Alternatively the curing takes place with microwave induction.

UV-curing systems are cured by application of actinic radiation such as UV light or electron beams. In the case of dual-cure systems the general approach would be to carry out a UV curing first and then a thermal cure.

As is known, the photopolymerization of unsaturated compounds can be inhibited by atmospheric oxygen, especially in thin layers. This effect can be diminished by known conventional methods, for example application of a temporary covering layer of polyvinyl alcohol or by (pre-)exposure or (pre-)conditioning under an inert gas. Suitable inert gases are nitrogen, helium, argon, etc. In many cases it is sufficient to reduce the oxygen concentration by a stream of inert gas.

The exposure of the compositions according to the invention can be effected by means of a large number of the most diverse light sources. Both point light sources and two-dimensional emitters (lamp carpets) are suitable. Examples are: carbon arc lamps, xenon arc lamps, mercury vapour lamps, if appropriate doped with metal halides (metal halide lamps), fluorescent lamps, incandescent argon lamps, electronic flashlights and photographic floodlights. Those lamps are particularly suitable which have a comparatively high radiation intensity in the spectral region from 400 to 480 nm. The distance between the lamp and the image material according to the invention can vary depending on the application and the type or intensity of the lamp, for example between 2 cm and 150 cm.

The compositions according to the invention are particularly useful for the production of a layer of a liquid crystal display. Thus, they can be employed e.g. for producing an overcoat layer of a colour filter or an insulating layer or a dielectric layer of a liquid crystal display.

In a special embodiment, the composition according to the invention is used for to form an overcoat layer of a color filter. Color filters are an important part of a liquid crystal display panel and must satisfy various requirements. Of importance are e.g. the heat resistance and chemical resistance of the color filter. Electronic display usually contains a color filter set comprising: a green color filter having a green filter layer a blue color filter having a blue filter layer; a red color filter having a red filter layer (RGB color filters) and optionally a black matrix. To form liquid crystal display panels, a transparent layer (overcoat layer) is to be formed on the color filter and further processed into a transparent electrode. If the transparent electrode layer is deposited after applying the RGB color filter elements and the black matrix, an additional overcoat film as a protective layer can be applied on the color filter layer prior to deposition of the electrode layer. The production of color filters for LCDs is described e.g. in U.S. Pat. No. 5,650,263, which is incorporated herein by reference.

To form an overcoat layer of a color filter, usually a thermosetting composition is employed. The composition of the present invention can also be used as a thermosetting composition to form such overcoat layers.

Cured films of the compositions of the invention have at least one of the following advantageous properties: excellent in flatness, good hardness, good chemical and/or thermal resistance, good transparency, especially in a visible region, good adhesion to various substrates, suitability for forming transparent conductive films, e.g. an ITO film.

It is a demand of protective layers that unnecessary parts of the protective layer, for example on scribing lines for cutting the substrate and on bonding pads of solid image sensors should be easily removable from the substrate (see e.g. JP57-42009-A, JP1-130103-A and JP1-134306-A). Resins that are only cured thermally are not always optimal for this application. Now it was surprisingly found that a thermosetting composition according to the invention that includes photopolymerizable components (dual cure composition), allows to easily remove the unnecessary parts of the protective layer by photolithography.

The thermosetting compositions including photosensitive components according to the invention are also suitable for manufacturing interlayer insulating layers or dielectric layers in a liquid crystal display including an active matrix type display having a thin film transistor (TFT) as a switching device, and a passive matrix type without a switching device.

In recent years, liquid crystal displays have, for example, been widely used for pocket-type TV sets and terminal devices for communication by virtue of its small thickness and light weight. A reflection type liquid crystal display without necessity of using a back light is in particular in demand because it is ultra-thin and light-weight, and it can significantly reduce power consumption. However, even if a back light is removed out of a presently available transmission type color liquid crystal display and a light reflection plate is added to a lower surface of the display, it would cause a problem in that the efficiency of utilizing lights is low, and it is not possible to have practical brightness.

As a solution to this problem, there have been suggested various reflection type liquid crystal displays for enhancing an efficiency of utilizing lights. For instance, a certain reflection type liquid crystal display is designed to include a pixel electrode having reflection function The reflection type liquid crystal display includes an insulating substrate and an opposing substrate spaced away from the insulating substrate. A space between the substrates is filled with liquid crystals. A gate electrode is formed on the insulating substrate, and both the gate electrode and the insulating substrate are covered with a gate insulating film. A semiconductor layer is then formed on the gate insulating film above the gate electrode. A source electrode and a drain electrode are also formed on the gate insulating film in contact with the semiconductor layer. The source electrode, the drain electrode, the semiconductor layer, and the gate electrode cooperate with one another to thereby constitute a bottom gate type TFT as a switching device. An interlayer insulating film is formed covering the source electrode, the drain electrode, the semiconductor layer, and the gate insulating film therewith. A contact hole is formed throughout the interlayer insulating film on the drain electrode. A pixel electrode made of aluminum is formed on both the interlayer insulating film and an inner sidewall of the contact hole. The drain electrode of the TFT is eventually in contact with the pixel electrode through the interlayer insulating film. The interlayer insulating layer is generally designed to have a roughened surface by which the pixel electrode acts as a reflection plate which diffuses lights to get a wider angle for viewing (angle of visibility). The reflection type liquid crystal display remarkably enhances an efficiency of using lights by virtue that the pixel electrode acts as a light reflection plate.

In the above-mentioned reflection type liquid crystal display, the interlayer insulating film is designed to have projections and recesses by photolithography. To form and control a fine shape of the projections and recesses in micrometer order for surface roughness and to form contact holes, photolithography methods using positive and negative photoresists are used. For these resists the compositions according to the invention are especially suitable.

The interlayer insulating film may also be used for a transmissive type liquid crystal displays.

The thermosetting compositions according to the invention can further be used for manufacturing column spacers in liquid crystal display panels. In liquid crystal display devices, a liquid crystal layer capable of displaying images is generally arranged between a pair of substrates in accordance with a predetermined orientation. Maintenance of a uniform distance between the substrates, that is, maintaining a uniform thickness of the liquid crystal layer, is one factor determining image quality. For this purpose, spacers are disposed in order to keep the thickness of the liquid crystal layer uniform. The distance between the substrates is generally called the "cell thickness". The cell thickness usually represents the thickness of the liquid crystal layer, that is, the distance between two electrodes for applying an electric field to the liquid crystal in a display region.

The spacers have been formed by scattering beads. In recent years, however, spacers have been formed with high positional precision by photolithography using a photosensitive composition. Such a spacer, which is formed by use of a photosensitive composition, is called a photospacer.

Since the properties of light transmitted or reflected through the liquid crystal layer in a liquid crystal display are dependent on the cell gap, the thickness accuracy and uniformity over the pixel array are critical parameters for the performance of the liquid crystal display unit. A method of forming columns in the cell gap as spacers has been developed. In this method, columns of a resin are formed as spacers in the region between the pixel array region and the counter electrode to form a prescribed cell gap. Photosensitive materials having adhesive properties with photolithography are commonly used, for instance, in the manufacturing process of color filters. This method is advantageous compared with the conventional method using spacer beads in the points that location, number and height of the spacers may be controlled freely. In a color liquid crystal display panel, such spacers are formed in the nonimaging area under black matrix of color filter elements. Therefore, the spacers formed using photosensitive compositions do not decrease brightness and optical aperture.

Photosensitive compositions for producing protective layer with spacers for color filters are disclosed in JP2000-81701A and dry film type photoresists for spacer materials are also disclosed in JP11-174459A and JP11-174464A. As described in the documents, the photosensitive compositions, liquid and dry film photoresists, are comprising at least an alkaline or acid soluble binder polymer, a radically polymerizable monomer, and a radical initiator. Thermally crosslinkable components such as epoxide and oxetane are additionally included.

The steps to form spacers using a photosensitive composition are as follows: a photosensitive composition is applied to the substrate, for instance a color filter panel and after the substrate is prebaked, it is exposed to light through a mask. Then, the substrate is developed with a developer and patterned to form the desired spacers. A postbaking is carried out to thermally cure the composition.

The photocurable thermosetting compositions according to the invention are particularly suitable for producing spacers for liquid crystal displays (as described above) and lead to cured films with excellent application properties, e.g. excellent hardness, chemical and/or thermal resistance and good deformation restorability.

The thermosetting compositions including photosensitive components according to the invention are also suitable for manufacturing color filters for a liquid crystal display including an active matrix type display having a TFT as a switching device, and a passive matrix type without a switching device and other devices such as image sensors.

The color filters usually are prepared by forming red, green and blue pixels and optionally a black matrix on a glass substrate. A particularly preferred method of use comprises adding of the coloring matters, dyes and/or pigments of red, green and blue colors to the light-sensitive resin composition of the present invention, coating of the substrate with the composition, drying of the coating with a short heat treatment, pattern-wise exposure of the coating to actinic radiation and subsequent development of the pattern in an aqueous alkaline developer solution and a heat treatment. Thus, by subsequently applying a red, green and blue pigmented coating, in any desired order, on top of each other with this process a color filter layer with red, green and blue color pixels can be produced.

Negative or positive resists for manufacturing color filters are disclosed in JP1995-281440, JP1996-334893, JP1997-325483, 1997-197660, JP1995-261015 and WO9418274.

The compositions according to the invention can also be used advantageously for the following applications:

Adhesives, for example for electronic or optical materials in electronic devices such as semiconductor IC, semi-conductor devices, printed circuit board, LCD panel, PDP, EL, FED; for bonding between display panel and flexible printed circuit board (FPC), or chip on FPC (COF) and tape carrier package (TCP); for micro-bonding between semiconductor IC and circuit board: for optical component fixation.

Die bonding materials for bonding an electronic component, such as a semiconductor element, and a supporting member, such as a lead frame and an insulating supporting substrate; for example, a dicing/die bonding tape, a lead frame fixing tape and a LOC fixing tape; for hot press bonding of electric components through circuit-interconnecting hot-melt adhesive films, anisotropic electroconductive adhesives, pressure-sensitive adhesives and adhesive sheets.

Sealants for example for display elements such as liquid crystal panel, plasma display panel, and electroluminescence devices; for opto-electonic semiconductor such as LED or CCD; for electronic parts of semiconductor such as diode, transistor, IC, VLSI; for high-density recording media such as a magneto-optical disk; for solar battery, and optical waveguide.

Insulating materials, for example for electric or electronic parts, such as an insulating layer between circuits and insula-tors of printed circuit boards; for insulated coils; for wire insulation.

Coating compositions, for example for protective coating, decorative coating, insulating coatings, powder coating, surfacecoating, textile coatings; coating film of conventional organic solvent type paints used as an automobile topcoat paint.

Impregnating compositions, for example in the preparation of adhesives for metals, wood, cement and the like; in the preparation of reinforced composite products, such as laminated products, fila-ment windings, sheet molding compounds (SMC), electrical laminates, molding pow-ders, fluidized bed powders, potting compounds, etc; for electrical high-tension or low-tension components or electronic components; for liquid or solid coating, typically paints, lacquers or powder coating; Impregnating resins or impregnated tapes such as glass fiber impregnated tape.

Laminates e.g. laminating resins for electronic components, and copper-lined laminated sheets.

Molding materials, e.g. as or in a low pressure molding compound.

Casting materials e.g. as or in casting resins for the manufacture of transformers, especially of coil, e.g. for car ignition coils.

Substrates, e.g. substrates for semiconductor connection to be used in mounting a semiconductor element or a semiconductor integrated circuit for a wiring board (i.e. interposer), such as a TAB-type pattern processing tape and an interposer for a BGA package; plastic substrates for displays.

Other uses are for example printing inks, paints, color-proofing materials for printing, lacquers, varnishes, like gloss varnish; potting compounds, dipping resins, especially for electric condensers, matrix resins, especially for encapsulating or impregnating objects, construction materials, lenses, solder resist composition.

The examples which follow illustrate the invention in more detail, without restricting the scope to said examples only. Parts and percentages are, as in the remainder of the description and in the claims, by weight, unless stated otherwise. Where alkyl radicals having more than three carbon atoms are referred to in the examples without any mention of specific isomers, the n-isomers are meant in each case.

Example 1

Preparation of S1

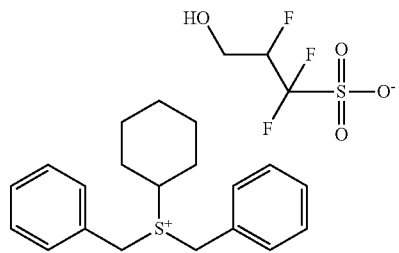

To 0.66 g of benzyl alcohol and 0.23 g of cyclohexanethiol are added 1.54 g of methanesulfonic acid at room temperature and stirred for 3.5 hours. The reaction mixture is neutralized with NaHCO₃ aq. solution, and then the aq. layer is washed with t-butyl methyl ether 3 times. To the aq. layer are added 0.44 g of sodium 1,1,2-trifluoro-3-hydroxypropane-1-sulfonate, which is prepared according to WO2011104127, at room temperature, and the reaction mixture is stirred for 30 min. The resulting sulfonium sulfonate is extracted with ethyl acetate. The organic layer is washed with water twice and then concentrated in vacuo. The resulting resin is washed with a mixed solvent of 1,4-dioxane and hexane twice, and 0.68 g of white resin are obtained.

Example 4

Preparation of S4

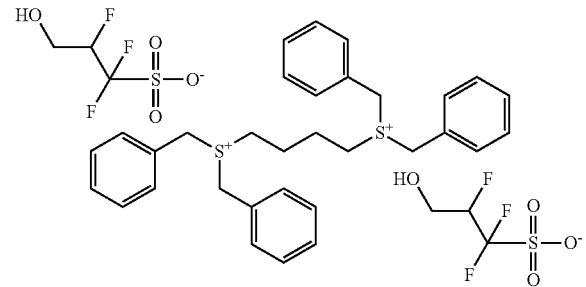

To 0.7 g of benzyl alcohol and 0.15 g of 1,4-bis(benzylthio)butane are added 0.58 g of methanesulfonic acid at room temperature and stirred overnight. After neutralizing the reaction mixture with NaHCO₃ aq. solution, the aq. layer is washed with t-butyl methyl ether. 0.25 g of sodium 1,1,2-trifluoro-3-hydroxypropane-1-sulfonate are added to this aq. layer at room temperature, and the reaction mixture is stirred for 1 hour. The resulting sulfonium sulfonate is extracted with ethylacetate and 2-butanone. The organic layer is repeatedly washed with water and then concentrated in vacuo. The resulting resin is washed with t-butyl methyl ether, and 0.26 g of colorless resin are obtained.

Example 17

Preparation of S17

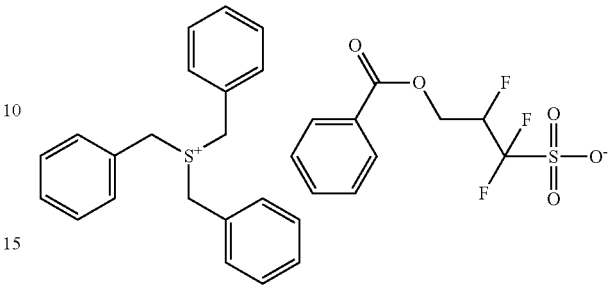

17.1 Preparation of 1,1,2-trifluoro-3-benzoyloxypropane-1-sulonate

To a suspension of 2.16 g of sodium 1,1,2-trifluoro-3-hydroxypropane-1-sulfonate in 5 mL of acetonitrile is added 2.81 g of benzoylchloride in 1 mL of acetonitrile and then 2.13 g of triethylamine in 1 mL of acetonitrile dropwise at room temperature. After stirring overnight, the reaction mixture is concentrated, and the residue was washed with t-butyl methyl ether. Water and ethyl acetate are added to this residue, and the organic layer is concentrated. 2.96 g of triethylammonim salt are obtained as colorless oil. ¹H-NMR (DMSO/TMS, δ ppm), 1.15 (t, 9H), 3.08 (q, 6H), 4.55 (ddd, 1H), 4.89 (dd, 1H), 5.18-5.41 (m, 1H), 7.53 (t, 2H), 7.66 (t, 1H), 7.98 (d, 2H), 8.81 (br s, 1H).

17.2 Preparation of S17

0.80 g of triethylammonim 1,1,2-trifluoro-3-benzoyloxypropane-1-sulfonate are dissolved in water, and this aq. layer is washed with t-butyl methyl ether. To this aq. solution are added 0.81 g of tribenzylsulfonium hydrogensulfonate and then 2 mL of ethyl acetate. After stirring for 1 hour at room temperature, 2-butanone is added, and the organic layer is separated and washed with water. 1.13 g of white solid is obtained after removal of organic solvents in vacuo.

The following novel compounds were prepared in a similiar manner.

| | Sulfonium sulfonates | | ¹H NMR solvent/δ (ppm, TMS) |
|---|---|---|---|
| S1 | | | DMSO-d6/1.12-1.40 (m), 1.50-1.66 (m), 1.71-1.85 (br d), 2.00-2.14 (br d), 3.46-3.61 (m), 3.66 (tt), 4.03 (ddd), 4.68-4.91 (m), 4.68 (d), 4.85 (d), 5.07 (t) 7.11-7.44 (m) |

| Sulfonium sulfonates | ¹H NMR solvent/δ (ppm, TMS) |
|---|---|
| S2 | DMSO-d6/0.84 (t), 1.26-1.38 (m), 1.46-1.69 (m), 3.19-3.32 (m), 3.46-3.61 (m), 4.03 (ddd), 4.68-4.91 (m), 4.74 (s), 5.06 (t), 7.43-7.54 (m) |
| S3 | DMSO-d6/3.24 (s), 3.46-3.61 (m), 4.03 (br dd), 4.68-4.91 (m), 4.81 (d), 4.98 (d), 5.07 (t), 6.96 (d), 7.17 (d), 7.23-7.42 (m), 7.70 (d), 10.78 (br s) |
| S4 | DMSO-d6/1.24-1.52 (br m), 2.94-3.16 (br m), 3.46-3.62 (m), 4.04 (br dd), 4.54-4.92 (m), 4.64 (d), 4.75 (d), 5.08 (br s) 7.04-7.64 (m) |
| S5 | DMSO-d6/3.47-3.62 (m), 4.04 (ddd), 4.68-4.92 (m), 4.76 (s), 5.07 (t), 7.24-7.37 (m) |
| S6 | DMSO-d6/2.41 (s), 4.19 (ddd), 4.64 (ddd), 4.76 (s), 5.00-5.24 (m), 7.24-7.38 (m), 7.48 (d), 7.78 (d) |

-continued

| | Sulfonium sulfonates | ¹H NMR solvent/δ (ppm, TMS) |
|---|---|---|
| S7 | (1-naphthylmethyl)(tetrahydrothiophenium) with 3-hydroxy-1,1,2-trifluoropropanesulfonate | DMSO-d6/2.12-2.24 (m), 2.34-2.46 (m), 3.30-3.62 (m), 4.04 (ddd), 4.68-4.92 (m), 4.98 (s), 5.07 (t), 7.57 (dd), 7.64 (t), 7.71 (t), 7.78 (d), 8.04 (d), 8.06 (d), 8.42 (d) |
| S8 | (1-naphthylmethyl)(methyl)(4-hydroxyphenyl)sulfonium with 3-hydroxy-1,1,2-trifluoropropanesulfonate | DMSO-d6/3.38 (s), 3.47-3.62 (m), 4.04 (dd), 4.68-4.92 (m), 5.07 (br s), 5.27 (d), 5.52 (d), 6.87 (d), 7.22 (d), 7.37 (dd), 7.56-7.68 (m), 7.95 (d), 7.97 (d), 8.32 (d), 10.72 (s) |
| S9 | dibenzyl(tetrahydrofurfuryl)sulfonium with 3-hydroxy-1,1,2-trifluoropropanesulfonate | DMSO-d6/1.43-1.56 (m), 1.69-1.86 (m), 1.88-2.00 (m), 3.35 (dd), 3.46-3.72 (m), 3.94-4.13 (m), 4.68-4.92 (m), 4.74 (d), 4.79 (d), 5.07 (t), 7.27-7.47 (m) |
| S10 | cyclohexyl bis(4-methylbenzyl)sulfonium with 3-hydroxy-1,1,2-trifluoropropanesulfonate | DMSO-d6/1.10-1.36 (m), 1.47-1.63 (m), 1.70-1.82 (br d), 1.98-2.08 (br d), 2.28 (s), 3.45-3.63 (m), 4.05 (ddd), 4.61 (d), 4.68-4.92 (m), 4.78 (d), 5.06 (t), 7.19 (d), 7.26 (d) |
| S11 | dibutyl(2-methylbenzyl)sulfonium with 3-hydroxy-1,1,2-trifluoropropanesulfonate | DMSO-d6/0.83 (t), 1.25-1.37 (m), 1.42-1.69 (m), 2.39 (s), 3.22-3.44 (m), 3.45-3.62 (m), 4.03 (dd), 4.68-4.92 (m), 4.77 (s), 5.06 (t), 7.28 (t), 7.31 (d), 7.37 (t), 7.46 (d) |
| S12 | ethyl(2-hydroxyethyl)(1-naphthylmethyl)sulfonium with 3-hydroxy-1,1,2-trifluoropropanesulfonate | DMSO-d6/1.23 (t), 3.28-3.65 (m), 3.69-3.88 (m), 4.03 (dd), 4.68-4.92 (m), 5.07 (t), 5.20 (d), 5.26 (d), 5.57 (t), 7.58 (dd), 7.64 (d), 7.70 (t), 7.76 (d), 8.05 (d), 8.07 (d), 8.29 (d) |
| S13 | benzyl(cyclopentyl)(phenyl)sulfonium with 3-hydroxy-1,1,2-trifluoropropanesulfonate | DMSO-d6/1.48-1.76 (m), 1.93-2.08 (m), 3.46-3.61 (m), 3.81-3.93 (m), 4.04 (ddd), 4.68-4.91 (m), 4.73 (d), 4.79 (d), 5.06 (t) 7.25-7.47 (m) |

-continued
| | Sulfonium sulfonates | ¹H NMR solvent/δ (ppm, TMS) |
|---|---|---|
| S14 | 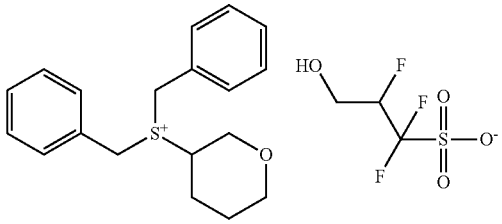 [SMILES: c1ccc(C[S+](Cc2ccccc2)C2CCCOC2)cc1 ; O=S(=O)([O-])C(F)(F)C(F)CO] | DMSO-d6/1.43-1.57 (m), 1.71-1.85 (m), 1.89-2.01 (m), 3.33 (dd), 3.46-3.76 (m), 3.85-4.04 (m), 4.04 (ddd), 4.68-4.91 (m), 4.74 (d), 4.79 (d), 5.07 (br s) 7.22-7.50 (m) *Mixture of stereoisomers |
| S15 | 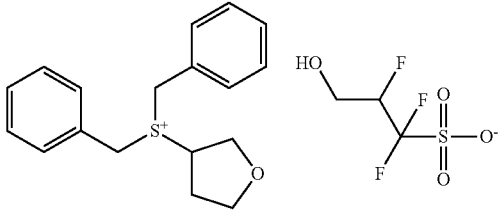 [SMILES: c1ccc(C[S+](Cc2ccccc2)C2CCOC2)cc1 ; O=S(=O)([O-])C(F)(F)C(F)CO] | DMSO-d6/2.07-2.18 (m), 2.29-2.42 (m), 3.46-3.65 (m), 3.78 (dd), 3.86 (dt), 3.94 (dd), 4.04 (ddd), 4.18-4.28 (m), 4.61-4.92 (m), 5.07 (t), 7.24-7.50 (m) *Mixture of stereoisomers |
| S16 | 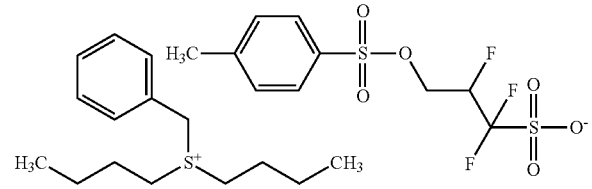 [SMILES: CCCC[S+](CCCC)Cc1ccccc1 ; Cc1ccc(S(=O)(=O)OCC(F)C(F)(F)S(=O)(=O)[O-])cc1] | DMSO-d6/0.84 (t), 1.26-1.39 (m), 1.46-1.69 (m), 2.41 (s), 3.17-3.30 (m), 4.19 (ddd), 4.64 (dd), 4.74 (s), 5.00-5.25 (m), 7.43-7.53 (m), 7.78 (d) |
| S17 | 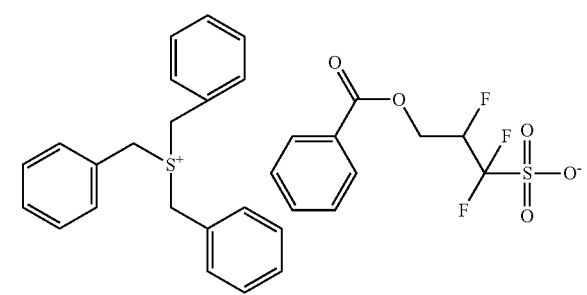 [SMILES: c1ccc(C[S+](Cc2ccccc2)Cc2ccccc2)cc1 ; O=C(OCC(F)C(F)(F)S(=O)(=O)[O-])c1ccccc1] | DMSO-d6/4.55 (ddd), 4.76 (s), 4.90 (dd), 5.19-5.41 (m), 7.22-7.38 (m), 7.53 (t), 7.66 (t), 7.98 (d) |
| S18 | 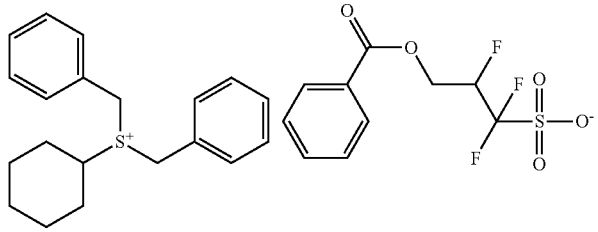 [SMILES: c1ccc(C[S+](Cc2ccccc2)C2CCCCC2)cc1 ; O=C(OCC(F)C(F)(F)S(=O)(=O)[O-])c1ccccc1] | DMSO-d6/1.12-1.40 (m), 1.50-1.66 (m), 1.71-1.85 (br d), 2.00-2.14 (br d), 3.60-3.72 (m), 4.55 (ddd), 4.68 (d), 4.85 (d), 4.90 (dd), 5.19-5.41 (m) 7.11-7.44 (m), 7.53 (t), 7.66 (t), 7.98 (d) |
| S19 | 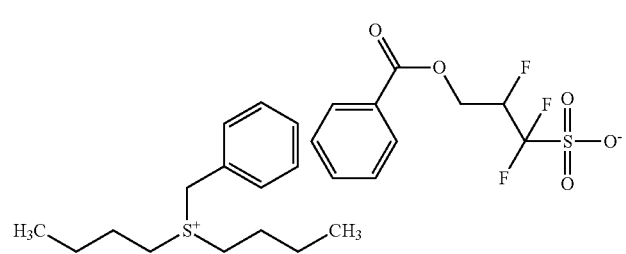 [SMILES: CCCC[S+](CCCC)Cc1ccccc1 ; O=C(OCC(F)C(F)(F)S(=O)(=O)[O-])c1ccccc1] | DMSO-d6/0.84 (t), 1.26-1.39 (m), 1.46-1.69 (m), 3.17-3.30 (m), 4.54 (ddd), 4.74 (s), 4.90 (dd), 5.18-5.41 (m), 7.41-7.57 (m), 7.67 (t), 7.98 (d) |

-continued

| | Sulfonium sulfonates | $^1$H NMR solvent/δ (ppm, TMS) |
|---|---|---|
| S20 | | DMSO-d6/3.66 (ddd), 4.12 (dd), 4.49 (d), 4.53 (d), 4.76 (s), 4.90-5.16 (m), 7.22-7.39 (m) |
| S21 | | DMSO-d6/1.12-1.40 (m), 1.50-1.66 (m), 1.71-1.85 (br d), 2.00-2.14 (br d), 3.60-3.72 (m), 4.11 (dd), 4.50 (d), 4.54 (d), 4.69 (d), 4.85 (dd), 4.90-5.16 (m) 7.11-7.44 (m) |
| S22 | | DMSO-d6/0.84 (t), 1.26-1.39 (m), 1.46-1.69 (m), 3.17-3.30 (m), 3.66 (ddd), 4.11 (dd), 4.50 (d), 4.54 (d), 4.74 (s), 4.90-5.16 (m), 7.22-7.38 (m), 7.41-7.55 (m) |
| S23 | | DMSO-d6/1.12-1.40 (m), 1.50-1.66 (m), 1.71-1.85 (br d), 2.00-2.14 (br d), 2.36 (s), 3.65 (br t), 4.51 (ddd), 4.68 (d), 4.85 (d), 4.86 (dd), 5.12-5.40 (m) 7.11-7.44 (m), 7.86 (d) |
| S24 | | DMSO-d6/2.04 (s), 4.20 (ddd), 4.65 (dd), 4.76 (s), 4.96-5.20 (m), 7.22-7.38 (m) |
| S25 | | DMSO-d6/1.12-1.40 (m), 1.50-1.66 (m), 1.71-1.85 (br d), 2.00-2.14 (br d), 2.04 (s), 3.66 (tt), 4.21 (ddd), 4.66 (dd), 4.68 (d), 4.85 (d), 4.96-5.20 (m) 7.11-7.44 (m) |

-continued

| Sulfonium sulfonates | $^1$H NMR solvent/δ (ppm, TMS) |
|---|---|
| S26 | DMSO-d6/3.22 (s), 4.46 (ddd), 4.82 (dd), 4.76 (s), 5.08-5.32 (m), 7.26-7.38 (m) |
| S27 | DMSO-d6/1.12-1.40 (m), 1.50-1.66 (m), 1.71-1.85 (br d), 2.00-2.14 (br d), 3.22 (s), 3.66 (tt), 4.46 (ddd), 4.69 (d), 4.73-4.90 (dd), 4.86 (d), 5.08-5.32 (m), 7.11-7.44 (m) |
| S28 | DMSO-d6/1.12-1.40 (m), 1.50-1.66 (m), 1.71-1.85 (br d), 2.00-2.14 (br d), 2.41 (s), 3.66 (tt), 4.17 (ddd), 4.57-4.72 (dd), 4.69 (d), 4.85 (d), 5.00-5.25 (m), 7.11-7.44 (m), 7.48 (d), 7.78 (d) |
| S29 | DMSO-d6/1.12-1.40 (m), 1.50-1.66 (m), 1.71-1.85 (br d), 2.00-2.14 (br d), 3.66 (tt), 4.24 (ddd), 4.68 (dd), 4.69 (d), 4.85 (d), 5.00-5.25 (m), 7.11-7.44 (m), 7.68 (t), 7.80 (t), 7.91 (d) |

APPLICATION EXAMPLES

Example A1

Thermal Curing Tests of Epoxy Formulation

An epoxy formulation is prepared by mixing:

| | |
|---|---|
| 25.0 parts by weight | poly[(o-cresyl glycidyl ether)-co-formaldehyde] (Sigma-Ardrich) |
| 75.0 parts by weight | propylene glycol monomethyl ether acetate |
| 0.5 parts by weight | sulfonium sulfonate according to the examples |

The sulfonium sulfonate to be tested is added to a solution of poly[(o-cresyl glycidyl ether)-co-formaldehyde] and mixed. The mixture is applied to a silicon wafer using a spin coater (1H-DX2, MIKASA). The solvent is removed by heating at 80° C. for 2 min in a convection oven. The thickness of the dry film is approximately 1.2 μm. The coating is further baked at 150° C. for 60 min or 180° C. for 60 min. The conversion of the epoxy group in baking is determined by measuring the IR absorption at 910 cm$^{-1}$ with a FT-IR spectrometer (FT-720, HORIBA) before and after baking. The higher the conversion, the more active is the tested sulfonium sulfonate. The results of the tests are given in table 2.

The formulations comprising the compounds of the comparative examples 1 and 2 were processed in the same manner as described above, except that the content of C2 in the formulation instead of 0.5 part by weight was 1 part by weight.

TABLE 2

| | Epoxy conversion (%) | |
|---|---|---|
| Compound | 150° C. for 60 min | 180° C. for 60 min |
| S1 | 94.4 | 100.0 |
| S2 | 93.8 | 99.0 |
| S3 | 95.4 | 98.3 |

TABLE 2-continued

| Compound | Epoxy conversion (%) 150° C. for 60 min | 180° C. for 60 min |
|---|---|---|
| S4 | 94.2 | 100.0 |
| S5 | 95.0 | 100.0 |
| S6 | 97.4 | 99.6 |
| S7 | 98.1 | 99.0 |
| S8 | 92.6 | 99.5 |
| S9 | 92.2 | 99.5 |
| S10 | 94.8 | 99.7 |
| S11 | 96.6 | 100.0 |
| S12 | 95.5 | 100.0 |
| S13 | 94.3 | 100.0 |
| S14 | 93.9 | 99.5 |
| S15 | 95.5 | 99.6 |
| S16 | 82.9 | 99.2 |
| S17 | 96.8 | 99.7 |
| S18 | 97.7 | 99.7 |
| S19 | 97.7 | 99.2 |
| S20 | 91.3 | 99.6 |
| S21 | 90.4 | 98.8 |
| S22 | 90.8 | 98.6 |
| S23 | 97.5 | 99.1 |
| S24 | 98.0 | 100.0 |
| S25 | 97.1 | 100.0 |
| S26 | 98.8 | 98.8 |
| S27 | 100.0 | 98.7 |
| S28 | 100.0 | 99.7 |
| S29 | 98.8 | 99.5 |
| C1 | 80.2 | 88.1 |
| C2 | 16.1 | 20.9 |

C1:

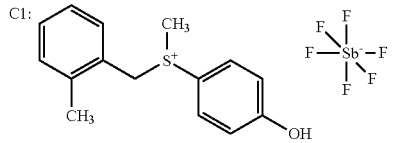

San-Aid SI-80, product of Sanshin Chemical Industry Co., Ltd

C2:

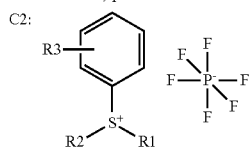

San-Aid SI-110L, product of Sanshin Chemical Industry Co., Ltd

The invention claimed is:

1. A compound of the formula I, Ia or Ib

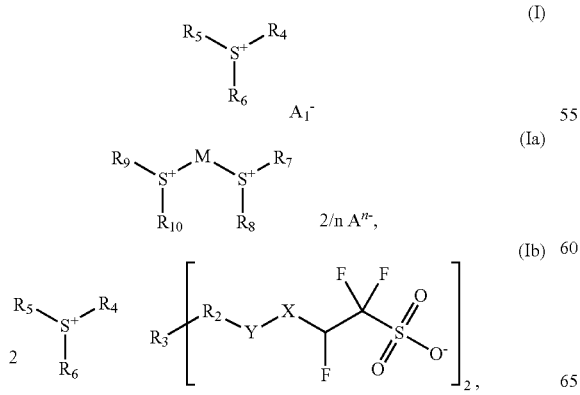

wherein $A_1^-$ is an anion selected from the group consisting of

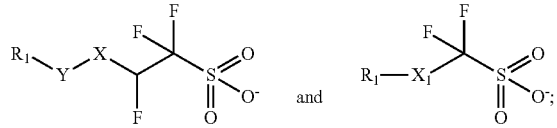

$A^-$ is an anion selected from the group consisting of

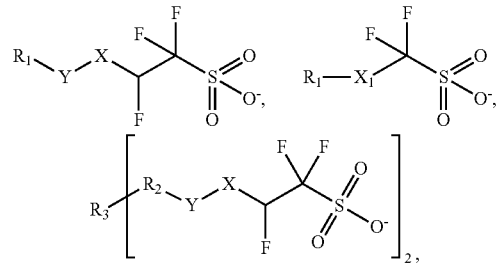

$PF_6^-$, $SbF_6^-$, $BF_4^-$, tetrakis(pentafluorophenyl)borate, fluoroalkylphosphate, pentafluorobenzenesulfonate, nitrobenzenesulfonate, di(alkoxycarbonyl)benzenesulfonate, perfluoroalkanesulfonate, difluoromethanedisulfonate, alkylsulfonate, tris(trifluoromethanesulfonyl)methide, bis(perfluoroalkanesulfonyl)imide and 1,1,2,2,3,3-hexafluoropropane-1,3-disulfonimide;

provided that at least one anion $A^-$ is and provided that the anions $A_1^-$ and $A^-$ are not -continued

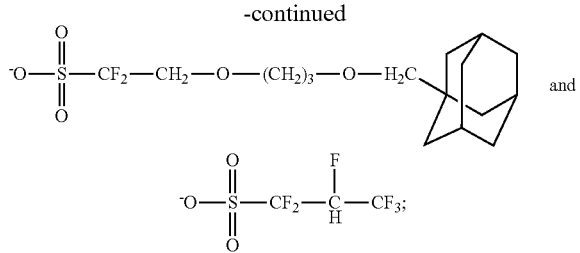 and n is 1 or 2;
X is $C_1$-$C_4$alkylene or CO;
$X_1$ is $CH_2$, CO, O, S, $CF_2O$, $SO_2$, $SO_2O$, $SO_2N$ or (CO)O;
Y is O, O(CO), O(CO)O, O(CO)$NR_{11}$, O(CO)$NR_{11}$(CO), $OSO_2$, O(CS), or O(CS)$NR_{11}$, in which for each of these the oxygen atom is directly bound to X;
or is $NR_{11}$, S, $NR_{11}$(CO)O, $NR_{11}$(CS)O, in which the N- or S-atom is directly bound to X;
$R_1$ is hydrogen, $C_1$-$C_{18}$alkyl, $C_2$-$C_{18}$alkyl which is interrupted by one or more of O, S, $NR_{14}$, CO, O(CO) or $NR_{14}$(CO), or is phenyl-$C_1$-$C_3$-alkyl or $C_1$-$C_{10}$haloalkyl, wherein said $C_1$-$C_{18}$alkyl, interrupted $C_2$-$C_{18}$alkyl, phenyl-$C_1$-$C_3$-alkyl or $C_1$-$C_{10}$haloalkyl are unsubstituted or are substituted by one or more identical or different $Z_1$;
or $R_1$ is $C_2$-$C_{12}$alkenyl or $C_2$-$C_{18}$alkenyl which is interrupted by one or more of O, S, $NR_{14}$, CO, O(CO), $NR_{14}$(CO) or $Z_3$, wherein said uninterrupted or interrupted $C_2$-$C_{12}$alkenyl is unsubstituted or substituted by one or more identical or different $Z_1$;
or $R_1$ is $C_3$-$C_{30}$cycloalkyl, $C_3$-$C_{30}$cycloalkyl-$C_1$-$C_{18}$alkyl or $C_4$-$C_{30}$cycloalkenyl, wherein said $C_3$-$C_{30}$cycloalkyl, $C_3$-$C_{30}$cycloalkyl-$C_1$-$C_{18}$alkyl or $C_4$-$C_{30}$cycloalkenyl is unsubstituted or substituted by one or more identical or different $Z_1$ and wherein said unsubstituted or substituted $C_3$-$C_{30}$cycloalkyl, $C_3$-$C_{30}$cycloalkyl-$C_1$-$C_{18}$alkyl or $C_4$-$C_{30}$cycloalkenyl optionally is interrupted by one or more identical or different O, S, $NR_{14}$, CO, O(CO) or $NR_{14}$(CO);
or $R_1$ is phenyl, naphthyl, anthracyl, phenanthryl, biphenylyl, fluorenyl or $C_3$-$C_{20}$heteroaryl wherein said phenyl, naphthyl, anthracyl, phenanthryl, biphenylyl, fluorenyl or $C_3$-$C_{20}$heteroaryl are unsubstituted or are substituted by one or more identical or different $Z_2$;
or $R_1$ is $NR_{12}R_{13}$ or a monovalent $C_{17}$-$C_{50}$hydrocarbon group of steroid structure which optionally comprises one or more heteroatoms;
$Z_3$ is phenylene, naphthylene, anthracylene, phenanthrylene, biphenylene or $C_3$-$C_{20}$heteroarylene, wherein said phenylene, naphthylene, anthracylene, phenanthrylene, biphenylene or $C_3$-$C_{20}$heteroarylene are unsubstituted or substituted by one or more identical or different $Z_1$;
$R_2$ and $R_3$ independently of each other are $C_1$-$C_{10}$haloalkylene, $C_1$-$C_{10}$haloalkylene substituted by one or more identical or different $Z_1$;
or $R_2$ and $R_3$ are $C_1$-$C_{18}$alkylene, $C_3$-$C_{30}$cycloalkylene, $C_3$-$C_{30}$cycloalkyl-$C_1$-$C_{18}$alkylene, $C_2$-$C_{12}$alkenylene or $C_4$-$C_{30}$cycloalkenylene wherein said $C_1$-$C_{18}$alkylene, $C_3$-$C_{30}$cycloalkylene, $C_3$-$C_{30}$cycloalkyl-$C_1$-$C_{18}$alkylene, $C_2$-$C_{12}$alkenylene or $C_4$-$C_{30}$cycloalkenylene is uninterrupted or interrupted by one or more identical or different O, S, $NR_{14}$, CO, O(CO) or $NR_{14}$(CO) and wherein said uninterrupted or interrupted $C_1$-$C_{18}$alkylene, $C_3$-$C_{30}$cycloalkylene, $C_3$-$C_{30}$cycloalkyl-$C_1$-$C_{18}$alkylene, $C_2$-$C_{12}$alkenylene or $C_4$-$C_{30}$cycloalkenylene is unsubstituted or substituted by one or more identical or different $Z_1$;
or $R_2$ and $R_3$ are phenylene, naphthylene, anthracylene, phenanthrylene, biphenylene or $C_3$-$C_{20}$heteroarylene, wherein said phenylene, naphthylene, anthracylene, phenanthrylene, biphenylene or $C_3$-$C_{20}$heteroarylene is unsubstituted or substituted by one or more identical or different $Z_2$;
or $R_2$ and $R_3$ independently of each other are a direct bond, provided that $R_2$ and $R_3$ are not both simultaneously a direct bond;
$R_4$ is a group

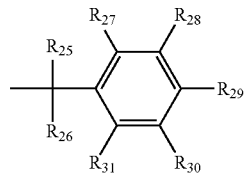

or a group

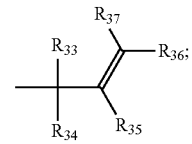

$R_5$ and $R_6$ independently of one another are unsubstituted $C_1$-$C_{20}$alkyl, $C_1$-$C_{20}$alkyl substituted by one or more identical or different $R_{2a}$, or
$C_2$-$C_{20}$alkyl interrupted by one or more non-adjacent O, S, C(O) or N($R_N$), wherein said interrupted $C_2$-$C_{20}$alkyl optionally is substituted by one or more identical or different $R_{2a}$, or
$C_2$-$C_{20}$alkenyl, $C_2$-$C_{20}$alkenyl substituted by one or more identical or different $R_{2a}$, wherein said unsubstituted or substituted $C_2$-$C_{20}$alkenyl optionally is interrupted by one or more non-adjacent O, S, C(O) or N($R_N$),
or $R_5$ and $R_6$ are $C_2$-$C_{20}$alkynyl, $C_2$-$C_{20}$alkynyl substituted by one or more identical or different $R_{2a}$, wherein said unsubstituted or substituted $C_2$-$C_{20}$-alkynyl optionally is interrupted by one or more non-adjacent O, S, C(O) or N($R_N$),
or $R_5$ and $R_6$ are $C_3$-$C_{20}$cycloalkyl, $C_3$-$C_{20}$cycloalkyl interrupted by one or more CO, and optionally substituted by one or more identical or different radicals $R_{2b}$,
or $R_5$ and $R_6$ are $C_3$-$C_{20}$heterocycloalkyl, $C_3$-$C_{20}$heterocycloalkyl interrupted by one or more CO and optionally substituted by one or more identical or different radicals $R_{2b}$,
or $R_5$ and $R_6$ are $C_6$-$C_{20}$aryl, $C_6$-$C_{20}$aryl substituted by one or more identical or different $R_{2c}$,
or $R_5$ and $R_6$ are $C_3$-$C_{20}$heteroaryl, $C_3$-$C_{20}$heteroaryl substituted by one or more identical or different $R_{2c}$;
or
$R_4$ and $R_5$ or $R_4$ and $R_6$ together form a straight-chain $C_2$-$C_6$alkylene, straight-chain $C_2$-$C_6$-alkenylene or a $(CH_2)_a$—$C_6H_4$—$(CH_2)_b$, wherein said $C_2$-$C_6$alkylene, $C_2$-$C_6$-alkenylene and the alkylene moiety of $(CH_2)_a$—$C_6H_4$—$(CH_2)_b$ optionally are substituted by one or more identical or different radicals $R_{32}$ and wherein said unsubstituted or substituted $C_2$-$C_6$alkylene, $C_2$-$C_6$-alkenylene and the alkylene moiety of $(CH_2)_a$—$C_6H_4$—$(CH_2)_b$ optionally are interrupted by one or more non-adjacent O, S, C(O) or $N(R_N)$;

or $R_5$ and $R_6$ together form a straight-chain $C_2$-$C_6$alkylene, a straight-chain $C_2$-$C_6$alkenylene, or a straight-chain $(CH_2)_c$—$C_6H_4$—$(CH_2)_d$, wherein said $C_2$-$C_6$alkylene, $C_2$-$C_6$alkenylene and the alkylene moiety of $(CH_2)_c$—$C_6H_4$—$(CH_2)_d$ optionally is substituted by one or more identical or different radicals $R_{32}$ and wherein said $C_2$-$C_6$alkylene, $C_2$-$C_6$alkenylene and the alkylene moiety of $(CH_2)_c$—$C_6H_4$—$(CH_2)_d$ optionally is fused to 1 or 2 phenyl rings; and wherein said $C_2$-$C_6$alkylene, $C_2$-$C_6$alkenylene and the alkylene moiety of $(CH_2)_c$—$C_6H_4$—$(CH_2)_d$ optionally is interrupted by one or more non-adjacent O, S, C(O) or $N(R_N)$;

a and b are an integer from 0 to 10 and the sum of a and b is 1 to 10;

c and d are an integer from 0 to 10 and the sum of c and d is 1 to 10;

$R_{2a}$ is F, Cl, Br, I, CN, $SR_{19}$, $OR_{20}$, $COR_{21}$, $COOR_{22}$, $CONR_{23}R_{24}$, $C_3$-$C_{20}$cycloalkyl, $C_3$-$C_{20}$cycloalkyl substituted by one or more identical or different $R_{2ab}$, wherein the unsubstituted or substituted $C_3$-$C_{20}$cycloalkyl optionally is interrupted by one or more CO, or $R_{2a}$ is $C_3$-$C_{20}$heterocycloalkyl, $C_3$-$C_{20}$heterocycloalkyl substituted by one or more identical or different $R_{2ab}$, wherein the unsubstituted or substituted $C_3$-$C_{20}$heterocycloalkyl optionally is interrupted by one or more CO, or $R_{2a}$ is $C_3$-$C_{20}$heteroaryl or $C_6$-$C_{10}$aryl, where said $C_3$-$C_{20}$heteroaryl or $C_6$-$C_{10}$aryl optionally are substituted by one or more identical or different $R_{2ac}$;

$R_{2ab}$ is F, Cl, Br, I, $C_1$-$C_{12}$-alkyl, $C_1$-$C_{12}$-haloalkyl, CN, $SR_{19}$, $OR_{20}$, $COR_{21}$, $COOR_{22}$ or $CONR_{23}R_{24}$;

$R_{2ac}$ is F, Cl, Br, I, $C_1$-$C_{12}$alkyl, $C_1$-$C_{12}$haloalkyl, CN, $NO_2$, $SR_{19}$, $OR_{20}$, $COR_{21}$, $COOR_{22}$, or $CONR_{23}R_{24}$;

$R_{2b}$ is F, Cl, Br, I, $C_1$-$C_{12}$alkyl, $C_1$-$C_{12}$haloalkyl, CN, $SR_{19}$, $OR_{20}$, $COR_{21}$, $COOR_{22}$, $CONR_{23}R_{24}$, $C_6$-$C_{10}$aryl or $C_3$-$C_{20}$heteroaryl where said $C_6$-$C_{10}$aryl or $C_3$-$C_{20}$heteroaryl optionally is substituted by one or more identical or different $R_{2ac}$;

$R_{2c}$ is F, Cl, Br, I, $C_1$-$C_{12}$alkyl, $C_1$-$C_{12}$haloalkyl, CN, $NO_2$, $SR_{19}$, $OR_{20}$, $COR_{21}$, $COOR_{22}$, $CONR_{23}R_{24}$, phenyl, $C_3$-$C_{10}$cycloalkyl or $C_3$-$C_{20}$heterocycloalkyl, wherein said $C_3$-$C_{10}$cycloalkyl or $C_3$-$C_{20}$heterocycloalkyl optionally are interrupted by one or more CO;

$R_7$, $R_8$, $R_9$ and $R_{10}$ independently of one another are $C_1$-$C_{20}$alkyl, $C_2$-$C_{20}$alkyl interrupted by one or more non-adjacent O, S, C(O) or $N(R_N)$, substituted by one or more identical or different $R_{2a}$, wherein said $C_1$-$C_{20}$alkyl or interrupted $C_2$-$C_{20}$alkyl optionally is substituted by one or more identical or different $R_{2a}$;

or $R_7$, $R_8$, $R_9$ and $R_{10}$ are $C_2$-$C_{20}$alkenyl, $C_2$-$C_{20}$alkenyl interrupted by one or more non-adjacent O, S, C(O) or $N(R_N)$, wherein said $C_2$-$C_{20}$alkenyl or interrupted $C_2$-$C_{20}$alkenyl optionally is substituted by one or more identical or different $R_{2a}$;

or $R_7$, $R_8$, $R_9$ and $R_{10}$ are $C_2$-$C_{20}$alkynyl, $C_2$-$C_{20}$alkynyl interrupted by one or more non-adjacent O, S, C(O) or $N(R_N)$, wherein said $C_2$-$C_{20}$alkynyl or interrupted $C_2$-$C_{20}$alkynyl optionally is substituted by one or more identical or different $R_{2a}$;

or $R_7$, $R_8$, $R_9$ and $R_{10}$ are $C_3$-$C_{20}$cycloalkyl, $C_3$-$C_{20}$cycloalkyl interrupted by one or more CO, wherein said $C_3$-$C_{20}$cycloalkyl or interrupted $C_3$-$C_{20}$cycloalkyl optionally is substituted by one or more identical or different $R_{2b}$;

or $R_7$, $R_8$, $R_9$ and $R_{10}$ are $C_3$-$C_{20}$heterocycloalkyl, $C_3$-$C_{20}$heterocycloalkyl interrupted by one or more CO, wherein said $C_3$-$C_{20}$heterocycloalkyl or interrupted $C_3$-$C_{20}$heterocycloalkyl optionally is substituted by one or more identical or different $R_{2b}$;

or $R_7$, $R_8$, $R_9$ and $R_{10}$ are $C_6$-$C_{20}$aryl or $C_3$-$C_{20}$heteroaryl, wherein said $C_6$-$C_{20}$aryl and $C_3$-$C_{20}$heteroaryl optionally is substituted by one or more identical or different $R_{2c}$;

or $R_7$ and $R_8$ and/or $R_9$ and $R_{10}$ together form a straight-chain $C_2$-$C_6$alkylene, a straight-chain $C_2$-$C_6$alkenylene or a straight-chain $(CH_2)_c$—$C_6H_4$—$(CH_2)_d$, wherein said $C_2$-$C_6$alkylene, $C_2$-$C_6$alkenylene and the alkylene moiety of —$(CH_2)_c$—$C_6H_4$—$(CH_2)_d$ optionally is substituted by one or more identical or different $R_{32}$ and wherein said $C_2$-$C_6$alkylene, $C_2$-$C_6$alkenylene and the alkylene moiety of $(CH_2)_c$—$C_6H_4$—$(CH_2)_d$ optionally is fused to 1 or 2 phenyl rings, and wherein said $C_2$-$C_6$alkylene, $C_2$-$C_6$alkenylene and the alkylene moiety of $(CH_2)_c$—$C_6H_4$—$(CH_2)_d$ optionally is interrupted by one or more non-adjacent O, S, C(O) or $N(R_N)$;

M is $C_1$-$C_{20}$alkylene, $C_2$-$C_{20}$alkenylene, $C_2$-$C_{20}$alkynylene, wherein said $C_1$-$C_{20}$alkylene, $C_2$-$C_{20}$alkenylene or $C_2$-$C_{20}$alkynylene optionally is substituted by one or more identical or different $R_{Ma}$, and wherein said unsubstituted or substituted $C_1$-$C_{20}$alkylene, $C_2$-$C_{20}$alkenylene or $C_2$-$C_{20}$alkynylene optionally is interrupted by one or more identical or different non-adjacent $R_{Mi}$;

or M is $C_3$-$C_{20}$cycloalkylene or $C_3$-$C_{20}$heterocycloalkylene, wherein said $C_3$-$C_{20}$cycloalkylene or $C_3$-$C_{20}$heterocycloalkylene optionally is interrupted by one or more CO, and wherein said uninterrupted or interrupted $C_3$-$C_{20}$cycloalkylene or $C_3$-$C_{20}$heterocycloalkylene optionally is substituted by one or more identical or different $R_{Mb}$;

or M is $C_6$-$C_{20}$arylene or $C_3$-$C_{20}$heteroarylene, wherein said $C_6$-$C_{20}$arylene is selected from the group consisting of phenylen, napthylene, anthracenediyl, and phenanthrenediyl, and wherein said $C_6$-$C_{20}$arylene or $C_3$-$C_{20}$heteroarylene optionally is substituted by one or more identical or different $R_{Mc}$;

$R_{Mi}$ is O, S, C(O), OC(O) or $N(R_N)$, or $R_{Mi}$ is $C_3$-$C_{20}$cycloalkylene, O—$C_3$-$C_{20}$cycloalkylene, O—$C_3$-$C_{20}$cycloalkylene-O or $C_3$-$C_{20}$heterocycloalkylene, wherein said $C_3$-$C_{20}$cycloalkylene, O—$C_3$-$C_{20}$cycloalkylene, O—$C_3$-$C_{20}$cycloalkylene-O or $C_3$-$C_{20}$heterocycloalkylene optionally is interrupted by one or more CO groups and wherein said uninterrupted or interrupted $C_3$-$C_{20}$cycloalkylene, O—$C_3$-$C_{20}$cycloalkylene, O—$C_3$-$C_{20}$cycloalkylene-O or $C_3$-$C_{20}$heterocycloalkylene optionally is substituted by one or more identical or different $R_{Mib}$;

or $R_{Mi}$ is $C_6$-$C_{20}$arylene, O—$C_6$-$C_{20}$arylene, O—$C_6$-$C_{20}$arylene-O, S—$C_6$-$C_{20}$arylene, S—$C_6$-$C_{20}$arylene-S or $C_3$-$C_{20}$heteroarylene, wherein said is $C_6$-$C_{20}$arylene, O—$C_6$-$C_{20}$arylene, O—$C_6$-$C_{20}$arylene-O, S—$C_6$-$C_{20}$arylene, S—$C_6$-$C_{20}$arylene-S or $C_3$-$C_{20}$heteroarylene optionally is substituted by one or more $R_{Mib}$;

$R_{Ma}$ is F, Cl, Br, I, CN, $SR_{19}$, $OR_{20}$, $COR_{21}$, $COOR_{22}$ or $CONR_{23}R_{24}$, $C_6$-$C_{10}$aryl or $C_3$-$C_{20}$heteroaryl wherein said $C_6$-$C_{10}$aryl or $C_3$-$C_{20}$heteroaryl optionally is substituted by one or more identical or different radicals selected from $C_1$-$C_{12}$alkyl, $C_1$-$C_{12}$haloalkyl, F, Cl, Br, I, CN, $NO_2$, $SR_{19}$, $OR_{20}$, $COR_{21}$, $COOR_{22}$ or $CONR_{23}R_{24}$;

$R_{Mib}$ is F, Cl, Br, I, $C_1$-$C_{12}$alkyl, $C_1$-$C_{12}$haloalkyl, CN, $NO_2$, $SR_{19}$, $OR_{20}$, $COR_{21}$, $COOR_{22}$ or $CONR_{23}R_{24}$ or phenyl;

$R_{Mb}$ is F, Cl, Br, I, $C_1$-$C_{12}$alkyl, $C_1$-$C_{12}$haloalkyl, CN, $SR_{19}$, $OR_{20}$, $COR_{21}$, $COOR_{22}$ or $CONR_{23}R_{24}$, $C_6$-$C_{10}$aryl or $C_3$-$C_{20}$heteroaryl wherein said $C_6$-$C_{10}$aryl or $C_3$-$C_{20}$heteroaryl optionally is substituted by one or more identical or different radicals selected from the group consisting of $C_1$-$C_{12}$alkyl, $C_1$-$C_{12}$haloalkyl, F, Cl, Br, I, CN, $NO_2$, $SR_{19}$, $OR_{20}$, $COR_{21}$, $COOR_{22}$ and $CONR_{23}R_{24}$;

$R_{Mc}$ is F, Cl, Br, I, $C_1$-$C_{12}$alkyl, $C_1$-$C_{12}$haloalkyl, CN, $NO_2$, $SR_{19}$, $OR_{20}$, $COR_{21}$, $COOR_{22}$ or $CONR_{23}R_{24}$, phenyl, $C_3$-$C_{10}$cycloalkyl or $C_3$-$C_{20}$heterocycloalkyl, wherein said $C_3$-$C_{10}$cycloalkyl or $C_3$-$C_{20}$heterocycloalkyl optionally is interrupted by one or more CO;

$R_{11}$ is hydrogen, $C_1$-$C_{18}$alkyl, $C_1$-$C_{10}$haloalkyl, $C_2$-$C_{12}$alkenyl, phenyl-$C_1$-$C_3$-alkyl;

or $R_{11}$ is $C_2$-$C_{18}$alkyl which is interrupted by one or more of O, S, $NR_{11a}$, CO, O(CO) or $NR_{11a}$(CO);

or $R_{11}$ is $C_3$-$C_{30}$cycloalkyl, $C_3$-$C_{30}$cycloalkyl-$C_1$-$C_{18}$alkyl or $C_4$-$C_{30}$cycloalkenyl, wherein said $C_3$-$C_{30}$cycloalkyl, $C_3$-$C_{30}$cycloalkyl-$C_1$-$C_{18}$alkyl or $C_4$-$C_{30}$cycloalkenyl optionally is interrupted by one or more identical or different O, S, $NR_{11a}$, CO, O(CO) or $NR_{11a}$(CO);

or $R_{11}$ is phenyl, naphthyl, anthracyl, phenanthryl, biphenyl, heteroaryl, $C_1$-$C_{18}$alkanoyl, benzoyl, $C_2$-$C_{18}$alkoxycarbonyl, phenoxycarbonyl, $C_1$-$C_{18}$alkylsulfonyl or phenylsulfonyl;

wherein the $C_3$-$C_{30}$cycloalkyl, $C_3$-$C_{30}$cycloalkyl-$C_1$-$C_{18}$alkyl, $C_1$-$C_{18}$alkyl, $C_1$-$C_{10}$haloalkyl, $C_2$-$C_{12}$alkenyl, $C_4$-$C_{30}$cycloalkenyl, phenyl-$C_1$-$C_3$-alkyl, interrupted $C_2$-$C_{18}$alkyl, interrupted $C_3$-$C_{30}$cycloalkyl, interrupted $C_3$-$C_{30}$cycloalkyl-$C_1$-$C_{18}$alkyl, interrupted $C_4$-$C_{30}$cycloalkenyl, phenyl, naphthyl, anthracyl, phenanthryl, biphenyl, heteroaryl, $C_1$-$C_{18}$alkanoyl, benzoyl, $C_2$-$C_{18}$alkoxycarbonyl, phenoxycarbonyl, $C_1$-$C_{18}$alkylsulfonyl or phenylsulfonyl are unsubstituted or substituted one or more identical or different $Z_1$;

or $R_1$ and $R_{11}$, together with the nitrogen atom to which $R_{11}$ is attached, form a 5-, 6- or 7-membered ring which optionally is interrupted by one or more O, $NR_{11a}$ or CO;

$R_{12}$ and $R_{13}$ independently of each other are hydrogen, $C_1$-$C_{10}$haloalkyl, $C_2$-$C_{12}$alkenyl, phenyl-$C_1$-$C_3$-alkyl, $C_1$-$C_{18}$alkyl or $C_2$-$C_{18}$alkyl which is interrupted by one or more identical or different O, S, $NR_{11a}$ CO, O(CO) or $NR_{11a}$(CO) and wherein said $C_1$-$C_{10}$haloalkyl, $C_2$-$C_{12}$alkenyl, phenyl-$C_1$-$C_3$-alkyl, $C_1$-$C_{18}$alkyl or interrupted $C_2$-$C_{18}$alkyl is unsubstituted or substituted by one or more identical or different $Z_1$;

or $R_{12}$ and $R_{13}$ are $C_3$-$C_{30}$cycloalkyl, $C_3$-$C_{30}$cycloalkyl-$C_1$-$C_{18}$alkyl or $C_4$-$C_{30}$cycloalkenyl, wherein said $C_3$-$C_{30}$cycloalkyl, $C_3$-$C_{30}$cycloalkyl-$C_1$-$C_{18}$alkyl or $C_4$-$C_{30}$cycloalkenyl optionally is interrupted by one or more identical or different O, S, $NR_{11a}$, CO, O(CO) or $NR_{11a}$(CO) and wherein said uninterrupted or interrupted $C_3$-$C_{30}$cycloalkyl, $C_3$-$C_{30}$cycloalkyl-$C_1$-$C_8$alkyl or $C_4$-$C_{30}$cycloalkenyl are unsubstituted or substituted by one or more identical or different $Z_1$;

or $R_{12}$ and $R_{13}$ independently of each other are $(CO)R_{21}$, $CO)OR_{21}$ or Ar which is unsubstituted or substituted by one or more identical or different $Z_1$;

or $R_{12}$ and $R_{13}$, together with the nitrogen atom to which they are attached, form a 5-, 6- or 7-membered ring which optionally is interrupted by one or more O, $NR_{11a}$ or CO;

$R_{11a}$ is hydrogen, $C_1$-$C_{10}$haloalkyl, $C_2$-$C_{12}$alkenyl, phenyl-$C_1$-$C_3$-alkyl, $C_1$-$C_{18}$alkyl or $C_2$-$C_{18}$alkyl which is interrupted by one or more of O, S, CO or O(CO), wherein said $C_2$-$C_{12}$alkenyl, phenyl-$C_1$-$C_3$-alkyl, $C_1$-$C_{18}$alkyl or interrupted $C_2$-$C_{18}$alkyl is unsubstituted or substituted by one or more identical or different $Z_1$;

or $R_{11a}$ is $C_3$-$C_{30}$cycloalkyl, $C_3$-$C_{30}$cycloalkyl-$C_1$-$C_{18}$alkyl or $C_4$-$C_{30}$cycloalkenyl wherein said $C_3$-$C_{30}$cycloalkyl, $C_3$-$C_{30}$cycloalkyl-$C_1$-$C_{18}$alkyl or $C_4$-$C_{30}$cycloalkenyl optionally is interrupted by one or more identical or different O, S, CO or O(CO) and wherein said uninterrupted or interrupted $C_3$-$C_{30}$cycloalkyl, $C_3$-$C_{30}$cycloalkyl-$C_1$-$C_{18}$alkyl or $C_4$-$C_{30}$cycloalkenyl is unsubstituted or substituted by one or more identical or different $Z_1$;

or $R_{11a}$ is phenyl, naphthyl, anthracyl, phenanthryl, biphenylyl, $C_3$-$C_{20}$heteroaryl, $C_1$-$C_{18}$alkanoyl, benzoyl, $C_2$-$C_{18}$alkoxycarbonyl, phenoxycarbonyl, $C_1$-$C_{18}$alkylsulfonyl or phenylsulfonyl, wherein said phenyl, naphthyl, anthracyl, phenanthryl, biphenylyl, $C_3$-$C_{20}$heteroaryl, $C_1$-$C_{18}$alkanoyl, benzoyl, $C_2$-$C_{18}$alkoxycarbonyl, phenoxycarbonyl, $C_1$-$C_{18}$alkylsulfonyl or phenylsulfonyl is unsubstituted or substituted one or more identical or different $Z_2$;

$R_{14}$ is hydrogen, Ar, $C_1$-$C_{10}$haloalkyl, $C_2$-$C_{12}$alkenyl, phenyl-$C_1$-$C_3$-alkyl, $C_1$-$C_{18}$alkyl or $C_2$-$C_{18}$alkyl which is interrupted by one or more identical or different O, S, $NR_{11a}$, CO, O(CO) or $NR_{11a}$(CO), wherein said Ar, $C_1$-$C_{10}$haloalkyl, $C_2$-$C_{12}$alkenyl, phenyl-$C_1$-$C_3$-alkyl, $C_1$-$C_{18}$alkyl or interrupted $C_2$-$C_{18}$alkyl is unsubstituted or substituted by one or more identical or different $Z_1$;

or $R_{14}$ is $C_3$-$C_{30}$cycloalkyl, $C_3$-$C_{30}$cycloalkyl-$C_1$-$C_{18}$alkyl or $C_4$-$C_{30}$cycloalkenyl wherein said $C_3$-$C_{30}$cycloalkyl, $C_3$-$C_{30}$cycloalkyl-$C_1$-$C_{18}$alkyl or $C_4$-$C_{30}$cycloalkenyl optionally is interrupted by one or more identical or different O, S, $NR_{11a}$, CO, O(CO) or $NR_{11a}$(CO) and wherein said uninterrupted or interrupted $C_3$-$C_{30}$cycloalkyl, $C_3$-$C_{30}$cycloalkyl-$C_1$-$C_{18}$alkyl or $C_4$-$C_{30}$cycloalkenyl is unsubstituted or substituted by one or more identical or different $Z_1$;

Ar is phenyl, biphenylyl, fluorenyl, naphthyl, anthracyl, phenanthryl or heteroaryl, wherein said phenyl, biphenylyl, fluorenyl, naphthyl, anthracyl, phenanthryl or heteroaryl are unsubstituted or substituted one or more identical or different $Z_2$;

$Z_1$ is Ar, OH, $C_1$-$C_{18}$alkyl, $C_1$-$C_{10}$haloalkyl, phenyl-$C_1$-$C_3$-alkyl, $C_3$-$C_{30}$cycloalkyl, halogen, $NO_2$, CN, $C_1$-$C_{18}$alkoxy, phenoxy, phenoxycarbonyl, phenylthio, phenylthiocarbonyl, $NR_{12}R_{13}$, $C_1$-$C_{12}$alkylthio, $C_2$-$C_{18}$alkoxycarbonyl, $C_2$-$C_{10}$haloalkanoyl, halobenzoyl, $C_1$-$C_{18}$alkylsulfonyl, phenylsulfonyl, (4-methylphenyl)sulfonyl, $C_1$-$C_{18}$alkylsulfonyloxy, phenylsulfonyloxy, (4-methylphenyl)sulfonyloxy, $C_1$-$C_{18}$alkanoyl, $C_1$-$C_{18}$alkanoyloxy, benzoyl and/or by benzoyloxy;

$Z_2$ is $C_1$-$C_{18}$alkyl, $C_2$-$C_{18}$alkyl which is interrupted by one or more of O, S, $NR_{11a}$, CO, O(CO) or $NR_{11a}$(CO);

or $Z_2$ is $C_3$-$C_{30}$cycloalkyl, $C_3$-$C_{30}$cycloalkyl-$C_1$-$C_{18}$alkyl or $C_4$-$C_{30}$cycloalkenyl, wherein said $C_3$-$C_{30}$cycloalkyl, $C_3$-$C_{30}$cycloalkyl-$C_1$-$C_{18}$alkyl or $C_4$-$C_{30}$cycloalkenyl optionally is interrupted by one or more identical or different O, S, $NR_{11a}$, CO, O(CO) or $NR_{11a}$(CO);

or $Z_2$ is $C_1$-$C_{10}$haloalkyl, $C_2$-$C_{12}$alkenyl, phenyl-$C_1$-$C_3$-alkyl, halogen, $NO_2$, CN, (CO)$R_{21}$, (CO)$OR_{22}$, (CO)$NR_{12}R_{13}$, O(CO)$R_{21}$, O(CO)$OR_{22}$, O(CO)$NR_{12}R_{13}$, $NR_{11a}$(CO)$R_{21}$, $NR_{11a}$(CO)$OR_{21}$, $NR_{11a}$(CO)$NR_{12}R_{13}$, $OR_{20}$, $NR_{12}R_{13}$, $SR_{11a}$, phenyl, biphenylyl, fluorenyl, naphthyl, anthracyl, phenanthryl and/or heteroaryl;

$R_{19}$ and $R_{20}$ independently of one another are hydrogen, $C_1$-$C_{20}$alkyl, $C_2$-$C_{12}$alkenyl, $C_3$-$C_{10}$cycloalkyl or $C_3$-$C_{20}$heterocycloalkyl, wherein said $C_3$-$C_{10}$cycloalkyl or $C_3$-$C_{20}$heterocycloalkyl optionally are interrupted by one or more CO;

or $R_{19}$ and $R_{20}$ are $C_2$-$C_{20}$alkyl which is interrupted by one or more non-adjacent O, S, C(O) or $N(R_N)$;

or $R_{19}$ and $R_{20}$ are $C_1$-$C_8$-alkyl substituted by one or more identical or different $R_{19a}$;

or $R_{19}$ and $R_{20}$ are —$(CH_2CH_2O)_mH$, —$(CH_2CH_2O)_m(CO)$—$(C_1$-$C_8$-alkyl), $C_2$-$C_8$-alkanoyl, $C_2$-$C_8$-haloalkanoyl, $C_3$-$C_6$-alkenoyl, benzoyl or benzoyl which is substituted by one or more identical or different F, Cl, Br, I, $C_1$-$C_6$-alkyl, OH or $C_1$-$C_4$-alkoxy;

or $R_{19}$ and $R_{20}$ are phenyl, naphthyl, both of which optionally are substituted by one or more identical or different $R_{19c}$;

or $R_{19}$ and $R_{20}$ are phenyl or naphthyl which forms a 5- or 6-membered ring via the phenyl ring to which $SR_{19}$ or $OR_{20}$, respectively, is attached via a single bond, $C_1$-$C_4$alkylene, O, S, CO or $NR_{23}$;

m is 1-20;

$R_{19a}$ is F, Cl, Br, I, OH, SH, CN, $C_3$-$C_{10}$cycloalkyl, $C_3$-$C_{20}$heterocycloalkyl, phenyl, $C_3$-$C_6$alkenoxy, —$OCH_2CH_2CN$, —$OCH_2CH_2(CO)O(C_1$-$C_8$alkyl), —$O(CO)$—$(C_1$-$C_8$alkyl), —$O(CO)$-phenyl, —(CO)OH or —(CO)$O(C_1$-$C_8$alkyl);

$R_{19c}$ is F, Cl, Br, I, $C_1$-$C_{12}$alkyl, $C_1$-$C_{12}$haloalkyl, $C_1$-$C_{12}$alkoxy, phenyl-$C_1$-$C_3$alkyloxy, phenoxy, $C_1$-$C_{12}$alkylsulfanyl, phenylsulfanyl, —(CO)$O(C_1$-$C_8$alkyl), (CO)$N(C_1$-$C_8$alkyl)$_2$ or phenyl;

$R_{21}$ is hydrogen, $C_1$-$C_{20}$alkyl, $C_2$-$C_{12}$alkenyl, $C_1$-$C_{20}$-alkyl which is interrupted by one or more non-adjacent O, S, CO or $N(R_N)$;

or $R_{21}$ is $C_1$-$C_8$alkyl substituted by one or more identical or different $R_{21a}$, or $R_{21}$ is —$(CH_2CH_2O)_mH$, —$(CH_2CH_2O)_m(CO)$—$(C_1$-$C_8$-alkyl), $C_3$-$C_{10}$cycloalkyl or $C_3$-$C_{20}$heterocycloalkyl, wherein said $C_3$-$C_{10}$cycloalkyl or $C_3$-$C_{20}$heterocycloalkyl optionally is interrupted by one or more CO;

or $R_{21}$ is $C_6$-$C_{20}$aryl or $C_3$-$C_{20}$heteroaryl, both of which optionally are substituted by one or more radicals identical or different $R_{19c}$;

$R_{21a}$ is F, Cl, Br, I, OH, SH, CN, phenyl, $C_3$-$C_6$alkenoxy, —$OCH_2CH_2CN$, —$OCH_2CH_2(CO)O(C_1$-$C_8$alkyl), —$O(CO)$—$(C_1$-$C_8$alkyl), —$O(CO)$-phenyl, —(CO)OH or —(CO)$O(C_1$-$C_8$alkyl);

$R_{22}$ is hydrogen, $C_1$-$C_{20}$alkyl, $C_2$-$C_{12}$alkenyl, $C_2$-$C_{20}$alkyl which is interrupted by one or more non-adjacent O, S, C(O) or $N(R_N)$, or $R_{22}$ is $C_1$-$C_8$alkyl substituted by one or more identical or different $R_{22a}$, or $R_{22}$ is —$(CH_2CH_2O)_mH$, —$(CH_2CH_2O)_m(CO)$—$(C_1$-$C_8$alkyl), $C_3$-$C_{10}$cycloalkyl, $C_3$-$C_{20}$heteroycloalkyl, wherein said $C_3$-$C_{10}$cycloalkyl, $C_3$-$C_{20}$heterocycloalkyl optionally are interrupted by one or more CO;

or $R_{22}$ is phenyl or naphthyl, both of which optionally are substituted by one or more identical or different $R_{19c}$;

$R_{22a}$ is F, Cl, Br, I, OH, SH, CN, $C_3$-$C_6$alkenoxy, —$OCH_2CH_2CN$, —$OCH_2CH_2(CO)O(C_1$-$C_8$alkyl), —$O(CO)$—$(C_1$-$C_8$alkyl), —$O(CO)$-phenyl, —(CO)OH, —(CO)$O(C_1$-$C_8$-alkyl), phenyl or naphthyl, wherein said phenyl or naphthyl optionally are substituted by one or more identical or different $R_{19c}$;

$R_{23}$ and $R_{24}$ independently of one another are hydrogen, $OR_{20}$, $C_1$-$C_{20}$alkyl, $C_2$-$C_{12}$alkenyl, $C_2$-$C_{20}$alkyl which is interrupted by one or more non-adjacent O, S, C(O) or $N(R_N)$;

or $R_{23}$ and $R_{24}$ are $C_1$-$C_8$-alkyl substituted by one or more identical or different $R_{23a}$;

or $R_{23}$ and $R_{24}$ are —$(CH_2CH_2O)_mH$, —$(CH_2CH_2O)_m(CO)$—$(C_1$-$C_8$alkyl), $C_2$-$C_8$alkanoyl, $C_2$-$C_8$-haloalkanoyl, $C_3$-$C_6$-alkenoyl, benzoyl, benzoyl which is substituted by one or more identical or different F, Cl, Br, I, $C_1$-$C_6$alkyl, OH or $C_1$-$C_4$alkoxy;

or $R_{23}$ and $R_{24}$ are $C_3$-$C_{10}$cycloalkyl or $C_3$-$C_{20}$heterocycloalkyl, wherein said $C_3$-$C_{10}$cycloalkyl or $C_3$-$C_{20}$heterocycloalkyl optionally are interrupted by one or more CO;

or $R_{23}$ and $R_{24}$ are phenyl or naphthyl both of which optionally are substituted by one or more identical or different $R_{19c}$;

$R_{23a}$ is F, Cl, Br, I, OH, SH, CN, phenyl, $C_3$-$C_6$alkenoxy, —$OCH_2CH_2CN$, —$OCH_2CH_2(CO)O(C_1$-$C_8$alkyl), —$O(CO)$—$(C_1$-$C_8$alkyl), —$O(CO)$-phenyl, —(CO)OH or —(CO)$O(C_1$-$C_8$alkyl);

or $R_{23}$ and $R_{24}$ together form a $C_2$-$C_5$alkylene group, which optionally is interrupted by one or more non-adjacent O, S, C(O) or $N(R_N)$;

$R_{25}$ and $R_{26}$ independently of one another are hydrogen, F, Cl, Br, I, CN, $NO_2$, $SR_{19}$, $OR_{20}$, $COR_{21}$, $COOR_{22}$, $CONR_{23}R_{24}$, $C_1$-$C_{20}$alkyl, $C_2$-$C_{20}$alkyl which is interrupted by one or more non-adjacent O, S, C(O) or $N(R_N)$ and wherein said uninterrupted $C_1$-$C_{20}$alkyl or interrupted $C_2$-$C_{20}$alkyl optionally is substituted by one or more identical or different $R_{2a}$;

or $R_{25}$ and $R_{26}$ are $C_3$-$C_{20}$cycloalkyl or $C_3$-$C_{20}$heterocycloalkyl, wherein said $C_3$-$C_{20}$cycloalkyl or $C_3$-$C_{20}$heterocycloalkyl optionally is interrupted by one or more CO and wherein said uninterrupted or interrupted $C_3$-$C_{20}$cycloalkyl or $C_3$-$C_{20}$heterocycloalkyl optionally is substituted by one or more identical or different $R_{2b}$;

or $R_{25}$ and $R_{26}$ are $C_6$-$C_{20}$aryl or $C_3$-$C_{20}$heteroaryl, wherein said $C_6$-$C_{20}$aryl or $C_3$-$C_{20}$heteroaryl optionally is substituted by one or more identical or different $R_{2c}$;

$R_{27}$, $R_{28}$, $R_{29}$, $R_{30}$ and $R_{31}$ independently of one another are hydrogen, F, Cl, Br, I, CN, $NO_2$, $SR_{19}$, $OR_{20}$, $COR_{21}$, $COOR_{22}$, $CONR_{23}R_{24}$, $C_1$-$C_{20}$alkyl, $C_2$-$C_{20}$alkyl which is interrupted by one or more non-adjacent O, S, C(O) or $N(R_N)$, wherein said $C_1$-$C_{20}$alkyl or interrupted $C_2$-$C_{20}$alkyl optionally is substituted one or more identical or different $R_{2a}$;

or $R_{27}$, $R_{28}$, $R_{29}$, $R_{30}$ and $R_{31}$ are $C_2$-$C_{20}$alkenyl or $C_2$-$C_{20}$alkynyl, wherein said $C_2$-$C_{20}$alkenyl or $C_2$-$C_{20}$alkynyl optionally are substituted one or more identical or different $R_{2a}$ and wherein said unsubstituted or substituted $C_2$-$C_{20}$alkenyl or $C_2$-$C_{20}$alkynyl optionally is interrupted by one or more non-adjacent O, S, C(O) or N($R_N$);

or $R_{27}$, $R_{28}$, $R_{29}$, $R_{30}$ and $R_{31}$ are $C_3$-$C_{20}$cycloalkyl or $C_3$-$C_{20}$heterocycloalkyl, wherein said $C_3$-$C_{20}$cycloalkyl or $C_3$-$C_{20}$heterocycloalkyl optionally is interrupted by one or more CO and wherein said $C_3$-$C_{20}$cycloalkyl or $C_3$-$C_{20}$heterocycloalkyl optionally is substituted by one or more identical or different $R_{2b}$;

or $R_{27}$, $R_{28}$, $R_{29}$, $R_{30}$ and $R_{31}$ are $C_6$-$C_{20}$aryl or $C_3$-$C_{20}$heteroaryl, wherein said $C_6$-$C_{20}$aryl or $C_3$-$C_{20}$heteroaryl optionally is substituted by one or more identical or different $R_{2c}$;

or two radicals $R_{27}$ and $R_{28}$, $R_{28}$ and $R_{29}$, $R_{29}$ and $R_{30}$ and/or $R_{30}$ and $R_{31}$ together form a straight-chain $C_2$-$C_6$alkylene or a straight-chain $C_2$-$C_6$alkenylene, wherein said $C_2$-$C_6$alkylene or $C_2$-$C_6$alkenylene optionally is substituted by one or more identical or different $R_{32}$ and wherein said unsubstituted or substituted $C_2$-$C_6$alkenylene optionally is fused to 1 or 2 $C_6$-$C_{10}$aryl rings and wherein said unsubstituted or substituted, unfused or fused $C_2$-$C_6$alkenylene optionally is interrupted by one or more non-adjacent O, S, C(O) or N($R_N$);

$R_{32}$ is F, Cl, Br, I, CN, $NO_2$, $SR_{19}$, $OR_{20}$, $COR_{21}$, $COOR_{22}$, $CONR_{23}R_{24}$, $C_1$-$C_{20}$alkyl, $C_2$-$C_{20}$alkenyl or $C_2$-$C_{20}$alkynyl;

or $R_{32}$ is $C_2$-$C_{20}$alkyl, $C_2$-$C_{20}$alkenyl or $C_2$-$C_{20}$-alkynyl which is interrupted by one or more non-adjacent O, S, C(O) or N($R_N$), wherein said uninterrupted $C_1$-$C_{20}$alkyl, $C_2$-$C_{20}$alkenyl, $C_2$-$C_{20}$alkynyl or said interrupted $C_2$-$C_{20}$alkyl, $C_2$-$C_{20}$alkenyl or $C_2$-$C_{20}$-alkynyl optionally is substituted one or more identical or different $R_{32a}$, or $R_{32}$ is $C_3$-$C_{20}$cycloalkyl or $C_3$-$C_{20}$heterocycloalkyl, wherein said $C_3$-$C_{20}$cycloalkyl or $C_3$-$C_{20}$heterocycloalkyl optionally is interrupted by one or more CO and wherein said interrupted or uninterrupted $C_3$-$C_{20}$cycloalkyl or $C_3$-$C_{20}$heterocycloalkyl optionally is substituted by one or more identical or different $R_{32b}$;

or $R_{32}$ is $C_6$-$C_{20}$aryl or $C_3$-$C_{20}$heteroaryl, both of which optionally are substituted by one or more identical or different $R_{32c}$;

$R_{32a}$ is F, Cl, Br, I, CN, $SR_{19}$, $OR_{20}$, $COR_{21}$, $COOR_{22}$, $CONR_{23}R_{24}$, $C_3$-$C_{20}$cycloalkyl or $C_3$-$C_{20}$heterocycloalkyl wherein $C_3$-$C_{20}$cycloalkyl or $C_3$-$C_{20}$heterocycloalkyl optionally is interrupted by one or more CO and wherein said uninterrupted or interrupted $C_3$-$C_{20}$cycloalkyl or $C_3$-$C_{20}$heterocycloalkyl optionally is substituted by one or more identical or different $R_{2ab}$;

or $R_{32a}$ is phenyl or phenyl which is substituted by one or more identical or different $R_{2ac}$;

$R_{32b}$ is F, Cl, Br, I, $C_1$-$C_{12}$alkyl, $C_1$-$C_{12}$-haloalkyl, CN, $SR_{19}$, $OR_{20}$, $COR_{21}$, $COOR_{22}$, $CONR_{23}R_{24}$, phenyl or phenyl which is substituted by one or more identical or different $R_{2ac}$;

$R_{32c}$ is F, Cl, Br, I, $C_1$-$C_{12}$alkyl, $C_1$-$C_{12}$ haloalkyl, CN, $NO_2$, $SR_{19}$, $OR_{20}$, $COR_{21}$, $COOR_{22}$, $CONR_{23}R_{24}$, phenyl, $C_3$-$C_{10}$cycloalkyl or $C_3$-$C_{20}$heterocycloalkyl, wherein said $C_3$-$C_{10}$cycloalkyl or $C_3$-$C_{20}$heterocycloalkyl optionally is interrupted by one or more CO;

$R_N$ is hydrogen, $C_1$-$C_{20}$alkyl, $C_1$-$C_{10}$alkanoyl, $C_6$-$C_{10}$aroyl, $C_1$-$C_{20}$alkylsulfonyl, $C_2$-$C_{20}$alkenylsulfonyl, $C_6$-$C_{10}$arylsulfonyl, $C_6$-$C_{10}$aryl, $C_3$-$C_{20}$heteroaryl, $C_3$-$C_{10}$cycloalkyl or $C_3$-$C_{20}$heterocycloalkyl wherein said $C_3$-$C_{10}$cycloalkyl or $C_3$-$C_{20}$heterocycloalkyl optionally are interrupted by one or more CO;

$R_{33}$ and $R_{34}$ independently of one another are hydrogen, F, Cl, Br, I, CN, $NO_2$, $SR_{19}$, $OR_{20}$, $COR_{21}$, $COOR_{22}$, $CONR_{23}R_{24}$, $C_1$-$C_{20}$alkyl, $C_2$-$C_{20}$alkyl which is interrupted by one or more non-adjacent O, S, C(O) or N($R_N$), wherein said $C_1$-$C_{20}$alkyl or interrupted $C_2$-$C_{20}$alkyl optionally is substituted by one or more $R_{2a}$;

or $R_{33}$ and $R_{34}$ are $C_3$-$C_{20}$cycloalkyl or $C_3$-$C_{20}$heterocycloalkyl, where said $C_3$-$C_{20}$cycloalkyl or $C_3$-$C_{20}$heterocycloalkyl optionally is interrupted by one or more CO and wherein said $C_3$-$C_{20}$cycloalkyl or $C_3$-$C_{20}$heterocycloalkyl optionally is substituted by one or more identical or different $R_{2b}$;

or $R_{33}$ and $R_{34}$ are $C_6$-$C_{20}$aryl or $C_3$-$C_{20}$heteroaryl, wherein $C_6$-$C_{20}$aryl or $C_3$-$C_{20}$heteroaryl optionally is substituted by one or more identical or different $R_{2c}$;

$R_{35}$, $R_{36}$ and $R_{37}$ independently of one another are hydrogen, F, Cl, Br, I, CN, $NO_2$, $SR_{19}$, $OR_{20}$, $COR_{21}$, $COOR_{22}$, $CONR_{23}R_{24}$, $C_1$-$C_{20}$alkyl, $C_2$-$C_{20}$alkyl which is interrupted by one or more non-adjacent O, S, C(O) or N($R_N$), wherein said $C_1$-$C_{20}$alkyl or interrupted $C_2$-$C_{20}$alkyl optionally is substituted by one or more $R_{2a}$;

or $R_{35}$, $R_{36}$ and $R_{37}$ are $C_2$-$C_{20}$alkenyl or $C_2$-$C_{20}$alkynyl, wherein said $C_2$-$C_{20}$alkenyl or $C_2$-$C_{20}$-alkynyl optionally is substituted by one or more identical or different $R_{2a}$ and wherein said unsubstituted or substituted $C_2$-$C_{20}$alkenyl or $C_2$-$C_{20}$alkynyl optionally is interrupted by one or more non-adjacent O, S, C(O) or N($R_N$);

or $R_{35}$, $R_{36}$ and $R_{37}$ are $C_3$-$C_{20}$cycloalkyl or $C_3$-$C_{20}$heterocycloalkyl, wherein said $C_3$-$C_{20}$cycloalkyl or $C_3$-$C_{20}$heterocycloalkyl optionally is substituted by one or more identical or different $R_{2b}$;

or $R_{35}$, $R_{36}$ and $R_{37}$ are $C_6$-$C_{20}$aryl or $C_3$-$C_{20}$heteroaryl, wherein optionally is substituted by one or more identical or different $R_{2c}$;

or $R_{35}$ and $R_{36}$ together form straight-chain $C_2$-$C_6$alkylene or a straight-chain $C_2$-$C_6$alkenylene, wherein said $C_2$-$C_6$alkylene or $C_2$-$C_6$alkenylene optionally is substituted by one or more identical or different $R_{32}$ and wherein said $C_2$-$C_6$alkylene or $C_2$-$C_6$alkenylene optionally is interrupted by one or more non-adjacent O, S, C(O) or N($R_N$);

or two radicals $R_{33}$ and $R_{35}$, $R_{33}$ and $R_{37}$, $R_{34}$ and $R_{35}$ and/or $R_{34}$ and $R_{37}$ together form straight-chain $C_2$-$C_6$alkylene or $C_2$-$C_6$alkenylene, wherein said $C_2$-$C_6$alkylene or $C_2$-$C_6$alkenylene optionally is substituted by one or more identical or different $R_{32}$ and wherein said unsubstituted or substituted $C_2$-$C_6$alkylene optionally is interrupted by one or more non-adjacent groups O, S, C(O), C(O)O, C(O)N($R_N$) or N($R_N$).

2. The compound of claim 1 having formula I or Ia, wherein
$A_1^-$ is

[chemical structure: $R_1$-Y-X-C(F)(F)-S(=O)(=O)-O^-, with additional F]

$A^-$

[chemical structure: $R_1$-Y-X-CF(H?)-S(=O)(=O)-O^-, with F's]

provided that the anions $A_1^-$ and $A^-$ are not

[chemical structure: $^-O-S(=O)(=O)-CF_2-CF_2-O-CF_2-CF_3$]

[chemical structure: $^-O-S(=O)(=O)-CF_2-C(=O)-O-$adamantanone]

[chemical structure: $^-O-S(=O)(=O)-CF_2-C(=O)-H_2C-$adamantyl]

[chemical structure: $^-O-S(=O)(=O)-CF_2-CH_2-O-(CH_2)_3-O-H_2C-$adamantyl] and

[chemical structure: $^-O-S(=O)(=O)-CF_2-CFH-CF_3$];

n is 2;
X is methylene or CO;
Y is O, O(CO) or $OSO_2$, in which for each of these the oxygen atom is directly bound to X;
$R_1$ is hydrogen, $C_1$-$C_8$alkyl, or phenyl-$C_1$-$C_3$-alkyl, or $R_1$ is phenyl which is unsubstituted or are substituted by one or more identical or different $Z_2$;
$R_4$ is

[chemical structure (A): benzene ring with $R_{25}$, $R_{26}$ on CH group, and $R_{27}$, $R_{28}$, $R_{29}$, $R_{30}$, $R_{31}$ substituents]

$R_5$ is unsubstituted $C_1$-$C_{20}$alkyl, $C_1$-$C_{20}$alkyl substituted by one or more identical or different $R_{2a}$, $C_3$-$C_{20}$cycloalkyl, $C_6$-$C_{20}$aryl or $C_6$-$C_{20}$aryl substituted by one or more identical or different $R_{2c}$;
$R_6$ is unsubstituted $C_1$-$C_{20}$alkyl, $C_1$-$C_{20}$alkyl substituted by one or more identical or different $R_{2a}$, $C_6$-$C_{20}$aryl, $C_6$-$C_{20}$aryl substituted by one or more identical or different $R_{2c}$; or
$R_5$ and $R_6$ together form a straight-chain $C_2$-$C_6$alkylene;
$R_{2a}$ is $OR_{20}$, $C_3$-$C_{20}$heterocycloalkyl or $C_6$-$C_{10}$aryl;
$R_{2c}$ is $OR_{20}$;
$R_7$, $R_8$, $R_9$ and $R_{10}$ independently of one another are $C_1$-$C_{20}$alkyl;
M is $C_1$-$C_{20}$alkylene;
$Z_2$ is $C_1$-$C_{18}$alkyl;
$R_{20}$ is hydrogen;
$R_{25}$ and $R_{26}$ are hydrogen; and
$R_{27}$, $R_{28}$, $R_{29}$, $R_{30}$ and $R_{31}$ are hydrogen; or
two radicals $R_{30}$ and $R_{31}$ together form a straight-chain $C_2$-$C_6$alkenylene.

3. A heat-curable composition comprising
(a) at least one compound which is capable of undergoing cationic polymerization; and
(b) at least one compound of formula I, Ia or Ib according to claim 1.

4. The heat-curable composition according to claim 3, wherein the compound which is capable of undergoing cationic polymerization has at least one group selected from the group consisting of an epoxy group, oxetane group and vinyl ether group.

5. The heat-curable composition according to claim 3, where the compound which is capable of undergoing cationic polymerization is an epoxy resin.

6. The heat-curable composition according to claim 3, further comprising at least one component selected from the group consisting of solvent, reactive diluents, photoinitiators, photoacid generators, pigments, dispersants, ethylenically unsaturated compounds, binder being different from compounds (a) and different from ethylenically unsaturated compounds, sensitizer, thermal curing promoters being different from compounds of formula I, Ia and Ib, further additives and mixtures thereof.

7. A method for curing a cationic polymerizable composition, the method comprising
applying a composition to a substrate, and
exposing said composition to a treatment with heat,
wherein said composition comprises
(a) at least one compound which is capable of undergoing cationic polymerization; and
(b) at least one sulfonium compound selected from compounds of the formula I, Ia and Ib according to claim 1.

8. A thermal acid generator compound comprising a compound of formula I, Ia or Ib according to claim 1.

9. A layer or a component of a flat panel display comprising the composition according to claim 3.

10. The layer or component according to claim 9, wherein the flat panel display is a liquid crystal display, OLED display or plasma display panel.

11. The layer or component according to claim 9, wherein the layer is an overcoat layer of a color filter or an insulating layer or a dielectric layer.

12. A pigmented paint, a nonpigmented paint, a printing ink, a printing plate, an adhesive, a dental composition or a gel coat comprising the composition according to claim 3.

13. The method according to claim 7, wherein the substrate is a layer or a component of a flat panel display.

14. The method according to claim 7, wherein the substrate is an overcoat layer of a color filter or an insulating layer or a dielectric layer.

15. A coated substrate which is coated on at least one surface with the composition according to claim 3.

16. The composition according to claim 3 further comprising one or more additives selected from the group consisting of hardeners, crosslinkers, reinforcing materials, dyes, flow control assistants, UV stabilizers, heat stabilizers, weatherability improvers, rheology modifiers, flame retardants, antioxidants, discoloration inhibitors, biocides, antistatic agents, plasticizers, lubricants, slip additives, wetting agents, film-forming assistants, adhesion promoters, corrosion inhibitors, antifreeze agents, defoamers, mold release agents, and photolatent acids.

17. The compound of claim 1 having formula I.

18. The compound of claim 1 having formula Ia.

19. The compound of claim 1 having formula Ib.

20. The compound of claim 1, which is selected from the group consisting of

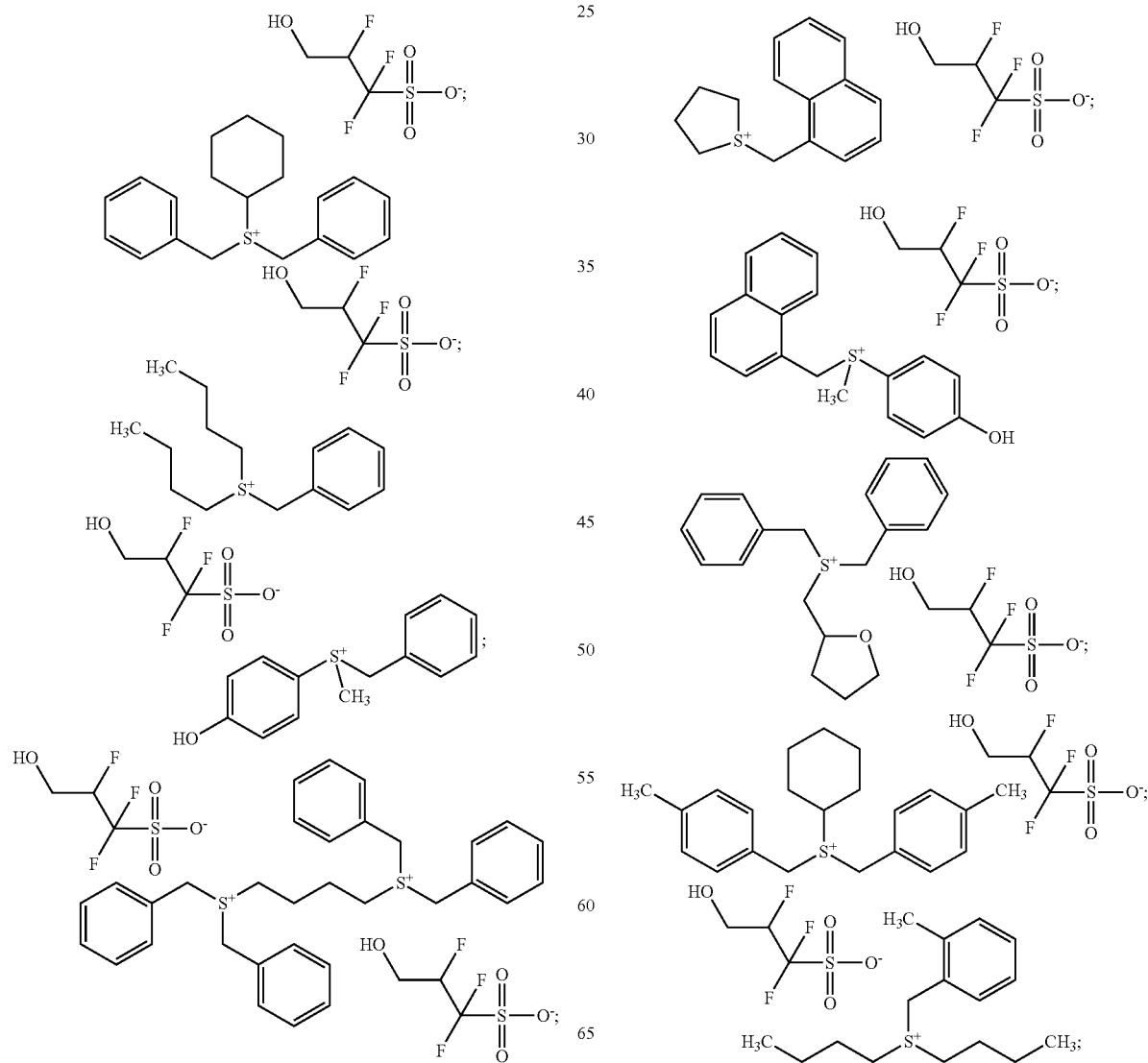

81
-continued
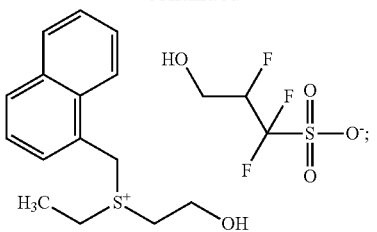
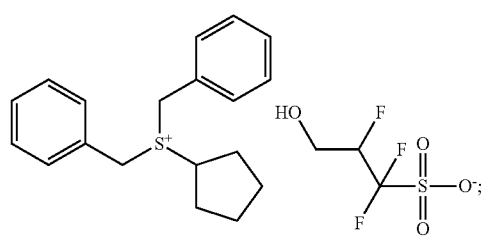
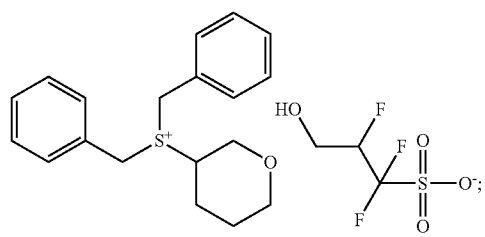
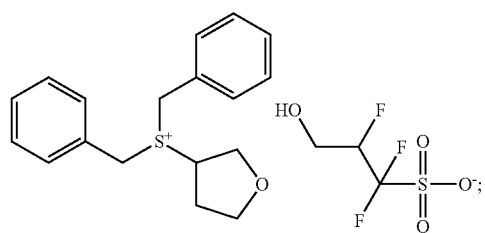
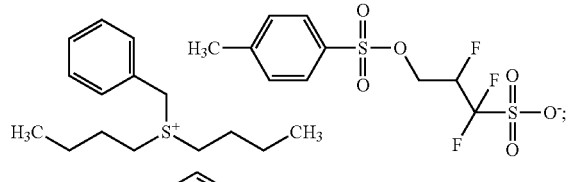
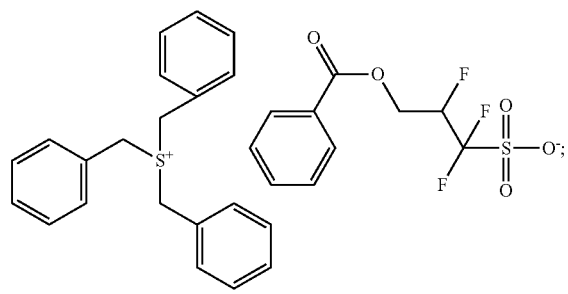
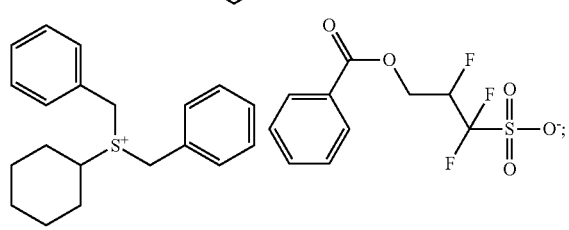
82
-continued
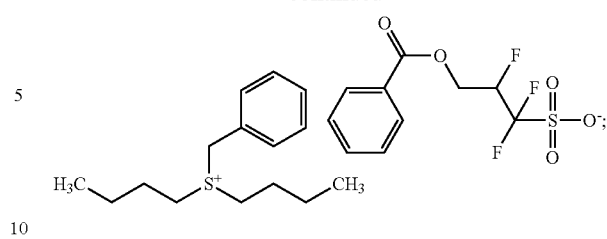
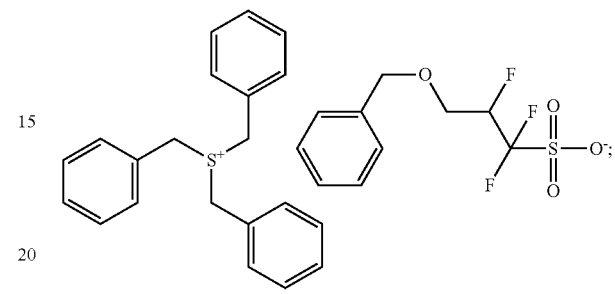
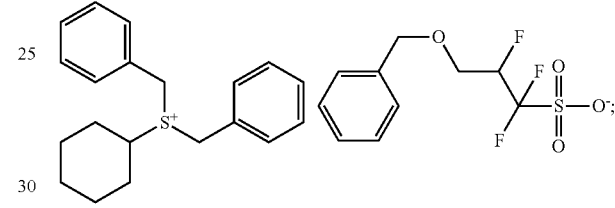
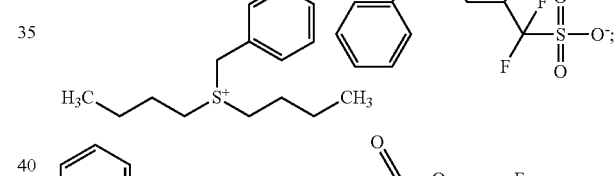
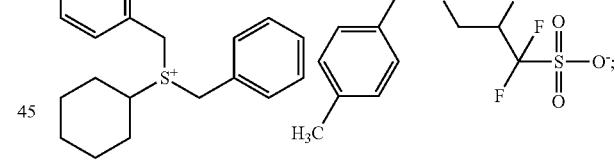
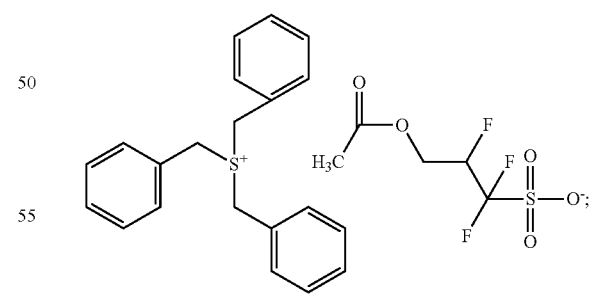
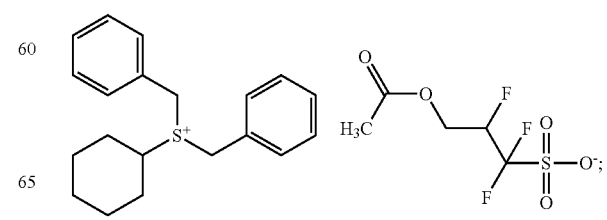

83
-continued
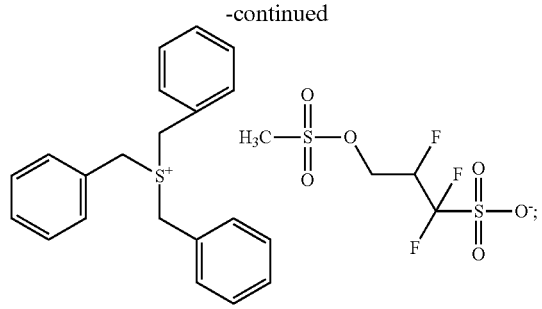
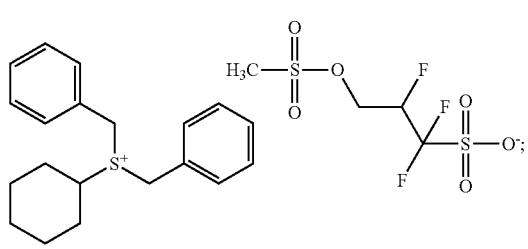
84
-continued
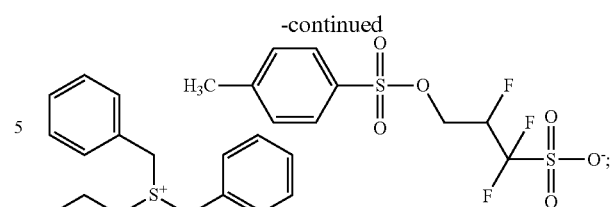
and
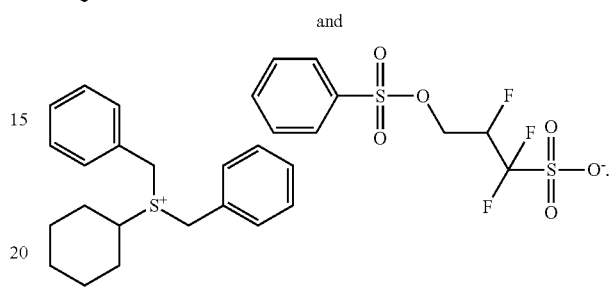
* * * * *